US006596319B2

(12) United States Patent
Rang et al.

(10) Patent No.: US 6,596,319 B2
(45) Date of Patent: Jul. 22, 2003

(54) IMMUNOMODULATING COMPOSITIONS FOR TREATMENT OF IMMUNE SYSTEM DISORDERS

(75) Inventors: Romeo G. Rang, Bucharest (RO); Paul B. Percheson, Uxbridge (CA)

(73) Assignee: Lorus Therapeutics Inc., Scarborough (CA)

( * ) Notice: Subject to any disclaimer, the term of this patent is extended or adjusted under 35 U.S.C. 154(b) by 0 days.

(21) Appl. No.: 09/764,010

(22) Filed: Jan. 17, 2001

(65) Prior Publication Data

US 2001/0009680 A1 Jul. 26, 2001

(51) Int. Cl.$^7$ ............................................. A61K 35/413

(52) U.S. Cl. ....................................... 424/551; 424/551

(58) Field of Search ........................................ 424/551

(56) References Cited

U.S. PATENT DOCUMENTS

| | | | |
|---|---|---|---|
| 4,372,949 A | 2/1983 | Kodama et al. | 514/78 |
| 4,562,179 A | 12/1985 | Teraji et al. | 52/172 |
| 4,585,762 A | 4/1986 | Teraji et al. | 514/129 |
| 4,767,610 A | 8/1988 | Long | 424/9.4 |
| 4,837,023 A | 6/1989 | Eibl | 424/439 |
| 4,879,226 A | 11/1989 | Wallace et al. | 435/68.1 |
| 4,916,249 A | 4/1990 | Brachwitz et al. | 558/169 |
| 4,935,520 A | 6/1990 | Nojima et al. | 546/22 |
| 4,965,391 A | 10/1990 | Counsell et al. | 558/169 |
| 5,049,552 A | 9/1991 | Eibl | 514/77 |
| 5,081,245 A | 1/1992 | Nomura et al. | 514/316 |
| 5,087,721 A | 2/1992 | Counsell et al. | 558/166 |
| 5,103,007 A | 4/1992 | Nomura et al. | 544/316 |
| 5,118,674 A | 6/1992 | Braquet et al. | 514/77 |
| 5,138,067 A | 8/1992 | Kamata et al. | 548/204 |
| 5,310,958 A | 5/1994 | Mizushima | 554/41 |
| 5,369,097 A | 11/1994 | Salari et al. | 514/77 |

FOREIGN PATENT DOCUMENTS

| | | |
|---|---|---|
| EP | 0 285 285 | 10/1988 |
| GB | 337797 | 11/1930 |
| WO | WO 98/06977 | 8/1989 |
| WO | WO 90/12583 | 11/1990 |
| WO | WO 95/07089 | 3/1995 |

OTHER PUBLICATIONS

Bandurski, et al., "The chromatographic identification of some biologically important phosphate esters," *J. Biol. Chem.*, vol. 193, pp. 405–110 (1951).

Braun, et al., "The in vitro development of cytotoxicity in response to granulocyte/macrophage–colony–stimulating factor or interferon γ in the peripheral blood monocytes of patients with solid tumors: Modulation by arachidonic acid metabolic inhibitors," *Cancer Immunology Immunotherapy*, vol. 32, pp. 55–61 (1990).

Braun, et al., "Sensitivity of Tumoricidal Function in Macrophages from Different Anatomical Sites of Cancer Patients to Modulation of Arachidonic Acid Metabolism," *Cancer Research*, vol. 53, pp. 3362–3368 (1993).

Greve, et al., "Bile Acids Inhibit Endotoxin–Induced Release of Tumor Necrosis Factor by Monocytes: An in Vitro Study," *Hepatology*, vol. 10, No. 4, pp. 454–458 (1989).

Larsen, et al., "Improved thin–layer chromatographic assay for monitoring lecithin/sphingomyelin ratios in amniotic fluid," *Journal of Chromatography*, vol. 226, pp. 484–487 (1981).

Miller, et al., "Reporting Results of Cancer Treatment," *Cancer*, vol. 47, pp. 207–214 (1981).

Rigler, et al., "Rapid quantification on Chromarods of cholesterol, total bile salts and phospholipids from the same microliter sample of human gallbladder bile," *Journal of Chromatography*, vol. 227, pp. 321–327 (1983).

Shinoda, et al., "Purification of a Leukocytosis Promotion–inhibiting Factor from Bovine Bile," *Chem. Pharm. Bull.*, vol. 30, No. 12, pp. 4429–4434 (1982).

Sundaram, et al., "Thin–layer chromatographic separation of chenodeoxy–cholic and deoxycholic acids," *Clin. Chim. Acta*, vol. 34, pp. 425–429 (1971).

Tamari, et al., "Etudes sur les Phosphonolipides de la Bile de Boeuf," *Agr. Biol. Chem.*, vol. 40, No. 10, pp. 2057–2062 (1976).

Thirlwell, et al., "Phase I–II Trial of an unconventional agent, virulizin, in patients with advanced cancer," *J. Cancer Res. Clin. Oncol.*, A1.240.01, pp. 51 (1990).

Warner, et al., "Phase II trial of Virulizin in patients with pancreatic cancer," *Clin. Invest. Med.*, vol. 17, No. 1, pp. 37–41.

Balch and Houghton, "Diagnosis of Metastic Melanoma at Distant Sites," in "Cutaneous Melanoma," 2d ed. (J.P. Lippincott Company, Philadelphia, PA, 1992).

Smith, et al., *Anal. Biochem* . . . , 150: pp. 76–85 (1985).

(List continued on next page.)

*Primary Examiner*—Jean C. Witz
(74) *Attorney, Agent, or Firm*—Gary M. Nath; Todd L. Juneau; Joshua B. Goldberg

(57) ABSTRACT

The present invention relates to a composition for use as an immunomodulator comprising small molecular weight components of less than 3000 daltons, and having the following properties: a) is extractable from bile of animals; b) is capable of stimulating monocytes and macrophages in vitro and in vivo; c) is capable of modulating tumor necrosis factor production; d) contains no measurable IL-1α, IL-1β, TNF, IL-6, IL-8, IL-4, GM-CSF or IFN-γ; e) has an antiproliferative effect in a malignant mouse hybridoma cell line; f) shows no cytotoxicity to human peripheral blood mononuclear cells or lymphocytes; and g) is not an endotoxin. The invention also relates to a method of preparing the composition, its use as an immunomodulator, and its use in the treatment of diseases and conditions having an immunological component.

8 Claims, 12 Drawing Sheets

OTHER PUBLICATIONS

Warner, et al., "Phase II Study of virulizin in Patients With Pancreatic Cancer," Clinical and Investigative Medicine Supplement, vol. 15, No. 4, pp. A89, Abstract 546 (Aug. 1992).

De La Garza, et al., "Phase II Trial of New Agent Virulizin (VZ) in Patients with Advanced Malignant Melanoma," Baylor College of Medicine Research Symposium, Houston, TX, Apr. 15, 1993. (See Footnote No. 1).

De La Garza, et al., "Phase II Trials of a New Agent, Virulizin (VZ) in Patients with Metastatic Melanoma and GI–Cancer," $2^{nd}$ Int'l Congress on Biological Response Modifiers, San Diego, CA, Jan. 29–31, 1993. (See Footnote No. 1).

Kabuta, et al., "The Prevention and Therapy by Simian Liver Extract and Bovine Gallbladder Bile Against Herpes Simplex Virus Infected Mice," J. Kuruma Med. Assoc., 48(6), 443–448 (1985). (See Footnote No. 1).

Munder, et al., "Alkyllylsophospholipids in Cancer Therapy," *Augmenting Agents in Cancer Therapy*, pp. 441–458, Hersh et al., eds. (Raven Press, NY, 1981). (See Footnote No. 1).

Ren, et al., "The effects of swine acids–sodium salt on the inhibition of proliferation and induction of differentiation in human promyelocytic leukemia cell line HL–60," *Chinese J. of Pharm. and Toxic.*, 3(3), 236–240 (1989). (See Footnote No. 1).

HYDROPHILIC COLUMN

Date: 14 Sept. 1993

COLUMN: HYDROXYETHYL
BUFFER: 50mM Formic
FLOW RATE: 1ml/min
O.D.: 254 nm
CHART SPEED: 0.5 cm/min

| Time (min) | Substance | Peak Height (inch) |
|---|---|---|
| | Virulizin B0213 | |
| 6.32 | whole | 8.00 |
| 8.22 | | 2.60 |
| 9.07 | | 10.00 |
| 10.30 | | 0.70 |
| 13.25 | | 0.90 |
| 6.58 | supernatant | 10.00 |
| 8.29 | | 1.00 |
| 10.00 | | 0.55 |
| 13.40 | | 0.60 |
| 6.38 | precipitate | 3.50 |
| 8.23 | | 0.25 |

FIG. 12A

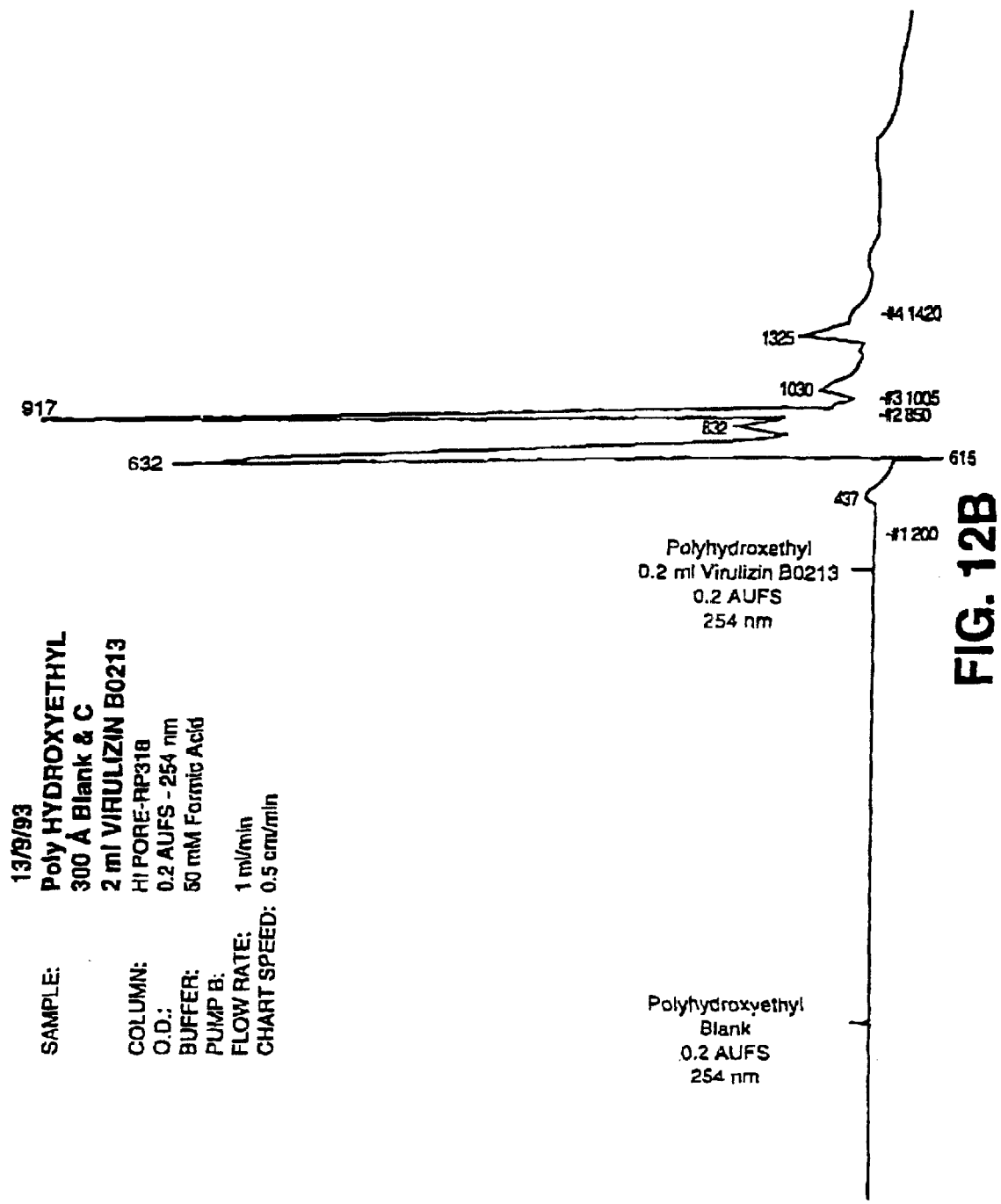

IMMUNOMODULATING COMPOSITIONS FOR TREATMENT OF IMMUNE SYSTEM DISORDERS

FIELD OF THE INVENTION

The present invention relates to immunomodulating compositions, pharmaceutical compositions comprising the same, and the use of such compositions in the treatment of mammals. In particular, the compositions are directed to the treatment of diseases associated with immune system disorders.

BACKGROUND OF THE INVENTION

Therapies are continuously being developed for the prophylaxis and treatment of cancer and autoimmune, infectious and inflammatory diseases, all of which may be a direct result of an inadequate immune system response. Some of these therapies attempt to use the immune system therapeutically.

One approach is based on the antigen-specific elements of the immune system, namely antibodies and T-cells. For example, research has been aimed at developing vaccines against foreign agents, or against certain endogenous chemical messengers, such as interleukins, to control or induce certain antibody reactions. A second approach is based on the isolation, cloning, expression and production of peptides and proteins from the nonantigen-specific parts of the immune system. For example, proteins, such as cytokines, which comprise the interleukins produced by white blood cells, and interferons, which stimulate lymphocytes and scavenger cells that digest foreign antigens, offer possibilities for therapies.

The treatment of cancer, for example, could be greatly enhanced if the early immune response to a tumor could be augmented so that the tumor does not reach a critical size. Strategies that have been suggested to augment the immune response to a tumor include: vaccines specific for tumor-associated antigens; the use of monoclonal antibodies against antigens on the surface of tumor cells, such as against the IL-2 receptor; the use of bispecific molecules containing antitumor antibodies and superantigens.

Relatively recently, the role of the physiologically active polypeptide, known as tumor necrosis factor (TNF), has been studied. In particular, TNF has been shown to induce necrosis of tumors, with no effect upon the normal tissues of the living body. The amino acid sequence of TNF, as well as the base sequence of the DNA coding for TNF, have been disclosed in U.S. Pat. No. 4,879,226.

Because TNF has been shown to have a role in inducing necrosis of tumors, any agent that can stimulate the production or bioavailability of TNF in vivo has potential utility as a treatment for various tumorous conditions. Additionally, any agent that can stimulate human monocytes and macrophages to produce TNF in vitro, is useful as a means for providing a source of TNF for therapeutic administration, as well as for analytical and diagnostic purposes.

Other diseases also have or involve an impaired immune system response. For example, autoimmune diseases are disorders in which the immune system produces an antibody against substances that are not foreign to the body, resulting in inflammation and consequent tissue damage. For example, rheumatoid arthritis (RA) is an autoimmune disease in which the body's immune system mistakenly recognizes normal cells of the lining of joints, called synovium, as foreign. The autoimmune attack may destroy the lining completely. In the most severe cases, the joints cease to function and are replaced surgically with artificial joints. TNF is a mediator of the damage in RA. Progression from mild symptoms to severe disfigurement can be very rapid. As yet, no treatment is available for RA patients. Other essentially untreatable autoimmune diseases include lupus erythematosus, multiple sclerosis, and amyotrophic lateral sclerosis.

Infectious diseases, such as those caused by bacteria, virus, and other opportunistic pathogens, can only succeed by avoiding or defeating the body's immune system. The immune system mounts or elicits either or both non-specific immune responses and specific immune response factors to fight such pathogens.

Non-specific immune responses are focused on cytokine production, principally by macrophages, and serve as a prelude to specific antibody responses. The inflammatory cytokines include TNF-$\alpha$ and mediate an acute response directed to the injury or infection sites, which is manifested by an increased blood supply. The pathogenic bacteria or viruses are engulfed by neutrophils and macrophages in an attempt to contain the infection to a small tissue space. Macrophages, therefore, play a key role in the defense against infectious diseases as follows:

(1) processing and presentation of antigens to lymphocytes so that antibody-mediated and cell-mediated immune responses can occur;

(2) secretion of cytokines central to immune response; and (3) destruction of antibody-coated bacteria, tumor cells or host cells.

Macrophages can ingest and kill a wide variety of pathogens, such as bacteria, fungi, and protozoa (parasites). This ability is augmented when the macrophages are "activated." Secreted products of activated macrophages are more diverse than those from any other immune cell. These regulate both pro- and anti-inflammatory effects and regulate other cell types. These products include TNF-$\alpha$, IL-1$\beta$, IL-6, hydrolytic enzymes, and products of oxidative metabolism Bacteria that are eliminated primarily through this cell-mediated immune process include tuberculosis and other related mycobacterial infections, such as atypical mycobacterial infections seen in up to 50% of AIDS patients, and anthrax, a potential bacteriological warfare agent. Fungal infections are common problems in immuno-suppressed patients, such as those afflicted with AIDS or organ transplant patients. Protozoa include organisms such as malaria.

Inflammatory diseases include endometriosis and inflammatory bowel disease, which also is mediated by immune processes. Endometriosis is an obscure disease of unknown cause and histogenesis that affects menstruating women. The disease is characterized by inappropriate implantation, growth, and function of endometrial cells. Endometrial cells and fragments, which are normally discharged during the menstrual cycle, are transported through the fallopian tubes into the peritoneal cavity where, in some women, they implant, proliferate, and develop into endometriotic lesions. However, because it appears the endometrial cells are present in the peritoneal cavity of all menstruating females, it is presently unclear why endometriosis develops in some, but not all, women. Endometriosis can result in painfully inflamed tissue, abnormal bleeding, widespread scaring, painful urination or defecation, and damage to a woman's reproductive organs, even leading to infertility. No known treatment for endometriosis exists, short of pregnancy, which provides temporary relief, or surgery to remove the source of endometrial cells, which also causes sterility.

Recently, numerous reports have suggested that endometriosis is associated with changes in the immune system. Early reports indicate that immunosuppressive treatments are associated with an increase in endometriosis in rhesus monkeys. Since that time, alterations in both cell-mediated and humoral immunity have been observed in humans with endometriosis.

During the past several years, studies have focused on the role of macrophages in endometriosis. The underlying hypothesis for these studies was that the monocyte/macrophage system regulates endometrial cell growth and prevents proliferation of misplaced endometrial cells in normal, healthy women. In women with endometriosis, the misplaced endometrial cells are allowed to implant, giving origin to endometriosis. Development of endometriosis then is a stimulus to auto-antibody production against endometrial cells and cell-derived antigens. These auto-antibodies, together with products from activated macrophages, may then interfere with fertility and reproductive performance of affected women.

The cumulative results from these studies have revealed the following pertinent facts:

(1) the peritoneal disposal system (consisting primarily of macrophages) that is thought to be responsible for the destruction of ectopic endometrial cells within the peritoneal cavity may be defective in women with extensive endometriosis;

(2) the defective peritoneal macrophage activity in women with extensive endometriosis is related, at least in part, to a prostaglandin-mediated event. Thus, significant stimulation of peritoneal macrophages from women with extensive endometriosis in response to macrophage activators, such as gamma interferon and endotoxin, could only be achieved when a prostaglandin synthesis inhibitor was included in the activation culture;

(3) products of circulating monocytes of endometriosis patients may be directly involved in regulating the growth of endometrial cells. In an unique co-culture system, enhancement of autologous endometrial cell proliferation was seen with monocytes from the majority of endometriosis patients, while suppression of proliferation was seen with monocytes from the most fertile control patients; and (4) the proliferation of endometrial cells from endometriosis patients can be modulated by macrophage-derived cytokines. The results obtained to date suggest that the proliferative response of endometrium from patients with limited disease can be enhanced by Interleukin-1-β (IL-1β) and TNF-α. In contrast, the proliferative response of endometrium from patients with extensive disease is suppressed by IL-1β and TNF-α.

Accordingly, the results of these studies suggest that the function of monocytes and macrophages from endometriosis patients play a significant role in the pathophysiology of the disease. Moreover, it appears that some of these macrophage functions are differently affected by the severity of the disease. In women with limited disease, macrophages appear to be hyperactivated in the peritoneal cavity, and perhaps, in the circulation and their endometrial cells appear to be able to respond to different macrophage-derived growth factors. In contrast, extensive endometriosis is characterized by suppression of macrophage activation within the peritoneal cavity due, in part, to hypersecretion of immunoregulatory prostaglandins. Macrophage products also appear to regulate the proliferation of endometrium in women with extensive endometriosis; however, qualitative differences in the response of endometrium to different cytokines suggests that the consequences of defective macrophage activation in these women may contribute to or, perhaps, control the disease.

Inflammatory bowel disease (IBD) is a general term for a group of chronic inflammatory disorders of unknown etiology involving the gastrointestinal tract. These disorders include nonspecific ulcerative colitis and Crohn's disease. Extraintestinal manifestations that may accompany these disorders (e.g., arthritis, pericholangitis) may represent autoimmune phenomena and therapeutic agents used to treat IBD, such as corticosteroids and azathioprine, may exert their effects via immunosuppressive mechanisms. Patients with inflammatory bowel disease may have humoral antibodies to colon cells, bacterial antigens such as *Escherichia coli*, lipopolysaccharide, and foreign proteins, such as cow milk protein. In general, the presence and titer of these antibodies does not correlate with disease activity; however, it is likely that these antigens gain access to immunocompetent cells secondary to epithelial damage. In addition, IBD has been described in association with agammaglobulinemia as well as IgA deficiency. Associated abnormalities of cell-mediated immunity include cutaneous anergy, diminished responsiveness to various mitogenic stimuli, and decreases in the number of peripheral T-cells.

Bile, which is secreted by the liver and stored in the gall bladder, has been investigated for various purposes, including the use of bile extracts to enhance bioavailability of drugs that are readily metabolized by normal liver function (see WO 90/12583) and to inhibit leucocytosis promotion in a mammal (see Shinoda et al., *Chem. Pharm. Bull.*, 30, 4429–4434 (1982)). However, bile has never been considered to be a source of therapeutically useful compositions with respect to neoplastic, inflammatory or infectious diseases. Interestingly, in accordance with British Pat. No. 337,797, it was suggested to use the gall bladder, itself, as a potential source of anti-cancer agents, but only after the bile had been removed from the gall bladder, and the gall bladder thoroughly washed.

SUMMARY OF THE INVENTION

It has now been discovered that bile is an important source of a composition that can activate immune system cells, such as macrophages and monocytes, and is effective in treating various cancers, especially pancreatic cancer and malignant melanoma. In particular, it has been discovered that the composition of the present invention can stimulate TNF production both in vitro and in vivo from, for example, macrophages. This property may be useful in the treatment of infectious diseases.

It has also been discovered that the immunomodulating effect (especially the ability to down-regulate or suppress TNF-α production) of the present invention may also be useful in the treatment of other immune system-involved disorders, such as autoimmune diseases and inflammatory diseases and disorders.

The bile composition of the present invention is also believed to be useful as an adjuvant additive for vaccines directed to childhood diseases, and as a protection against rejection phenomena involved in xenograph procedures, for example.

The bile composition of the present invention is obtained by extraction of bile with a water-soluble or miscible solvent. The extract so obtained may be further processed to remove unnecessary or undesirable components therefrom.

The product obtained by the process of extracting bile disclosed in further detail hereinbelow has been found to have TNF-stimulating activity (or TNF-inhibitory activity-depending on the species source) and is believed to have activity against cancer, infections, autoimmune disorders, and inflammatory disorders. In particular, it is believed that the bile extract of the present invention is especially active against pancreatic and other cancers.

Obviously, the entire composition so obtained may not be necessary to obtain such activity. Accordingly, it is possible to further separate, fractionate, or otherwise process the product thus obtained, and still retain the desired ability to stimulate TNF production, for example, to act against the immune system disorders that underlie various diseases. Moreover, it is envisioned that it is possible to obtain synthetically a product with the same or similar ability to stimulate TNF production and act against immune system disorders. Thus, it is envisioned that the components of the product may be identified and analyzed as to their respective contributions to the desired characteristics of TNF stimulation and ability to act against immune system disorders, among other biological effects. Moreover, it is further envisioned that such identification and analysis will be used to manufacture a synthetic form of the product.

In one aspect, the present invention relates to a composition for use as an immunomodulator comprising small molecular weight components of less than 3000 daltons, and having one or more of the following properties:

a) is extractable from bile of animals;

b) is capable of stimulating monocytes and macrophages in vitro and in vivo;

c) is capable of modulating tumor necrosis factor production;

d) contains no measurable level of IL-1α, IL-1β, TNF, IL-6, IL-8, IL-4, GM-CSF or IFN-γ;

e) has an anti-proliferative effect in a malignant cell line;

f) shows no cytotoxicity to human peripheral blood mononuclear cells or lymphocytes; and g) is not an endotoxin.

In accordance with a preferred embodiment, the composition is extracted from the bile of bovines and is capable of stimulating the release of TNF.

The composition of the invention may be prepared by (a) mixing bile from an animal, preferably a bovine, with a solvent that is soluble or miscible with water, preferably an alcohol, and preferably with an equal volume of an alcohol, to produce a bile/alcohol solution; (b) separating the solution which preferably is an alcohol-soluble fraction, and isolating therefrom a solution substantially free of alcohol, as by removing most of the alcohol, such as by the use of heat; (c) removing bile pigments from the solution to obtain a clear, yellowish liquid; (d) optionally treating the clear, yellowish liquid to substantially remove any residual alcohol; (e) removing fatty organic materials, as by extracting the clear, yellowish liquid with ether and isolating the aqueous phase; and (f) optionally removing residual ether from the aqueous phase.

The composition may be used without further modification by simply packaging it in vials and sterilizing. The composition may also be used in a concentrated form. A preferred concentrated form is prepared as follows. Prior to step (e) the clear, yellowish liquid may optionally be concentrated to about one-eighth of the volume of the bile/alcohol solution and after step (f) the aqueous phase may be concentrated so that it is one-tenth of the volume of the bile/ethanol solution.

The invention also relates to a pharmaceutical composition comprising the immunomodulating composition of the invention.

The invention further relates to a method of treating a patient comprising administering to said patient an effective amount of a composition of the invention. The invention still further relates to the use of a composition of the invention in the prophylaxis and treatment of diseases and conditions requiring modulation of the immune response; preferably infectious diseases, inflammatory diseases, autoimmune diseases, vaccination, rejection phenomena associated with xenographs, and neoplasias.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

Further details of the invention are described below with the help of the examples illustrated in the accompanying drawings in which:

FIG. 12 shows the conditions and times of elution of the composition of the invention on hydrophilic HPLC (a) and the elution profile for a supernatant of the composition of the invention (b);

DETAILED DESCRIPTION OF THE INVENTION

Figure 1:
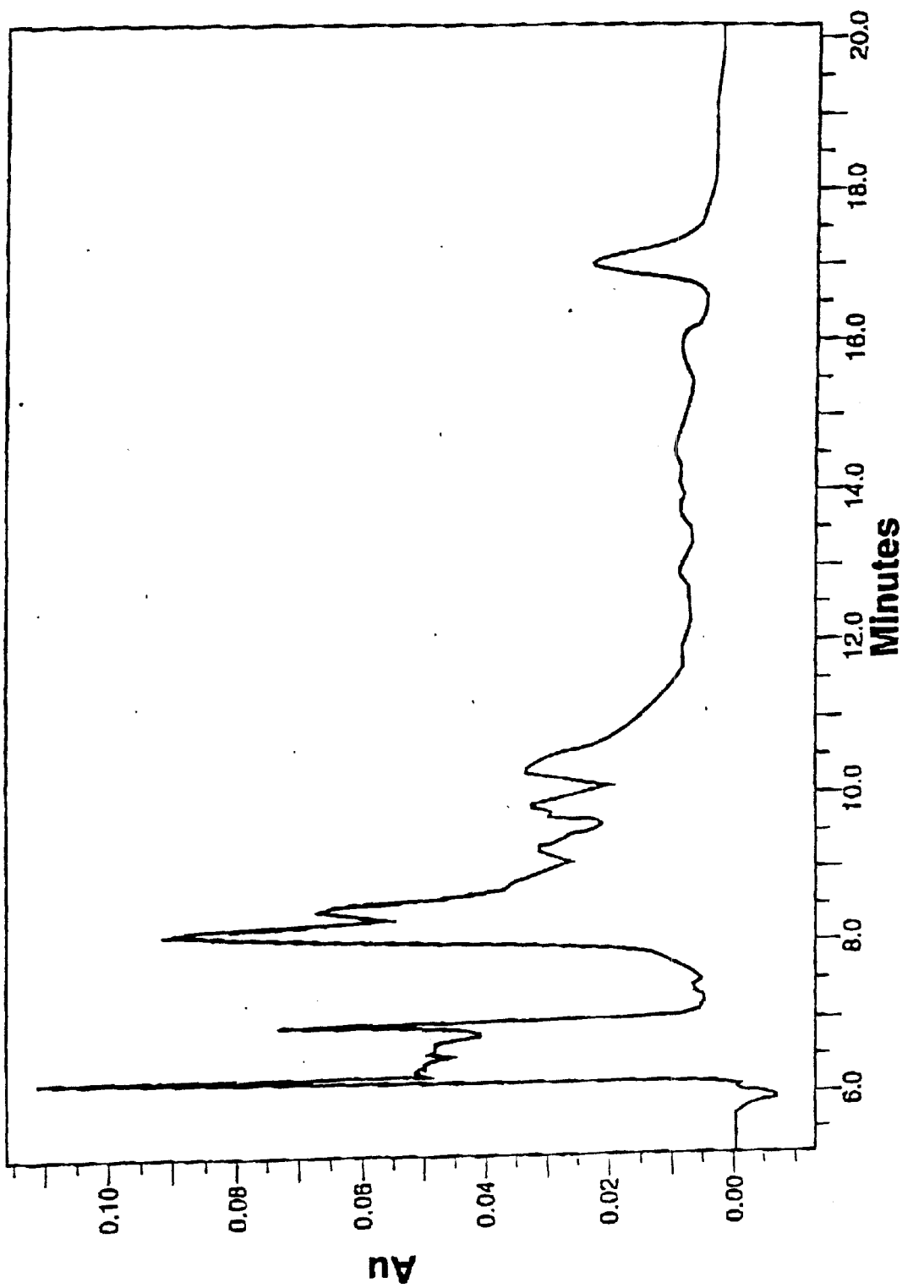
FIG. 1 is a Reverse Phase-High Performance Liquid Chromatography (RP-HPLC) profile for a concentrated composition of the invention.

The central hypothesis guiding these studies is that the therapeutic efficacy of a powerful biological stimulator can depend on its ability to elicit suitable modulation of the immune system, such as by activating macrophages and/or monocytes to produce certain cytokines or promote activity to seek and remove or destroy disease-causing or induced cells, such as foreign or misplaced cells. For example, tumoricidal function in environments that contain malignant disease would be a helpful therapy for fighting cancer. Such function could be generated by direct stimulation of resident immune cells in tumor microenvironments. Alternatively, this function could be generated by stimulation of circulating immune cells if those cells were then able to home on sites of malignant disease and to function in that environment. Other diseases and conditions that have an underlying immune system aspect would also be defeated or ameliorated by treatment with a suitable immunomodulating agent. Such diseases or conditions include endometriosis (which is a disease condition where normal endometrial cells are proliferating at inappropriate sites), various infectious diseases, and others, as more fully described hereinbelow.

As hereinbefore mentioned, the present invention relates to a composition for use as an immunomodulator comprising small molecular weight components of less than 3000 daltons, and having at least one of the following properties:

a) is extractable from bile of animals;

b) is capable of stimulating or activating monocytes and macrophages in vitro and in vivo;

c) is capable of modulating tumor necrosis factor production;

d) contains no measurable level of IL-1α, IL-1β, TNF, IL-6, IL-8, IL-4, GN-CSF or IFN-γ;

e) has an anti-proliferative effect in a malignant cell line;

f) shows no cytotoxicity to human peripheral blood mononuclear cells or lymphocytes; and g) is not an endotoxin.

More particularly, investigations have shown that at least some of the compositions of the invention will stimulate normal monocytes to effect cytotoxicity toward Chang hepatoma cells, which test is used to measure monocyte and macrophage activation. Monocytes and/or macrophages from cancer patients (including cervical, ovarian, ear/nose/throat, lung, and endometrial carcinomas, Kaposils sarcoma, and chronic myelogenous leukemia) also have been shown to be stimulated by the composition to attack and destroy their own particular tumor cells. Moreover, macrophages from patients afflicted with endometriosis have been shown to be activated by the composition as well (see Example 26).

The composition of the invention can modulate tumor necrosis factor (TNF) production. A preferred composition of the invention isolated from bile from bovines, promotes the release of TNF from human peripheral blood mononuclear cells and from the pre-monocyte cell line U-937 in what appears to be physiological quantities. Because TNF is known to initiate a cascade of inflammatory and antitumor cytokine effects, the preferred composition could exert its antineoplastic effect by stimulating human leukocytes to release TNF (and possibly other cytokines). Accordingly, the present invention also may enhance lymphocyte and macrophage cytotoxicity towards tumor cells.

The composition of the invention has also been found to inhibit the growth of cells of mouse hybridoma cell line HYB-6-1. The inhibitory effect of the composition in the mouse hybridoma cells suggests antiproliferative activity.

The effect of the composition on the survival of human peripheral blood mononuclear cells (PBMNs) and lymphocytes was also examined. The composition was found to be noncytotoxic to human PBMNs and lymphocytes.

As further exemplified below, the composition of the present invention has, among others, the following characteristics:

1) The component or components responsible for TNF-release from PBMNs eluted early from a $C_{18}$ RP-HPLC column.

2) The composition causes the release of interleukin-1 β (IL-1β), and the component responsible for the IL-1β release elutes early from RP-HPLC, suggesting that it is likely the same substance(s) that releases TNF.

3) The composition also causes the release of low quantities of interleukin-2 (IL-2).

4) The composition causes the release of granulocyte macrophage colony stimulating factor (GM-CSF);

5) The ratio of TNF to GM-CSF release is about 2:1.

6) It is likely that the same molecule(s), i.e., component (s), in the composition are responsible for releasing TNF, IL-1β and GM-CSF. It is possible that the composition acts to stimulate the release of multiple different cytokines, or alternatively, the composition triggers the production and release of one cytokine that in turn stimulates production and release of other cytokines.

7) Physicochemical analysis of the composition, including the precipitates and supernatants thereof, by SDS gel electrophoresis and molecular sieve HPLC indicates that the principal components are less than 2500 daltons.

8) Further physicochemical separation by hydrophilic (polyhydroxyethyl) molecular sieve HPLC confirms the small molecular weight of the components in the composition.

9) Amino acid analysis before and after acid hydrolysis suggest the presence of peptide bonds, indicating the presence of peptides.

As hereinbefore mentioned, the composition of the invention may be prepared by (a) mixing bile from an animal, preferably a bovine, with an equal volume of an alcohol to produce a bile/alcohol solution; (b) separating out the alcohol soluble fraction and isolating a solution substantially free of alcohol; (c) removing bile pigments from the solution to obtain a clear, yellowish liquid; (d) treating the clear, yellowish liquid to substantially remove any residual alcohol; (e) extracting the clear, yellowish liquid with ether and isolating the aqueous phase; and (f) removing residual ether from the aqueous phase.

The composition is obtained from the bile of any animal that produces bile. While the composition may possess a different activity toward a specific disease if obtained from the bile of one species as opposed to another, a generally suitable source of bile is that taken from sharks; bovines, ovines, caprines, and porcines. In most cases, it is practical to obtain the bile of slaughtered healthy food animals, such as bovines, ovines, caprines, and porcines, for use in the preparation of the composition of the invention. The bile thus collected should come directly from the gall bladders and/or hepatic organs (as appropriate to the species' anatomy and physiology) of the slaughtered animals and should be substantially clear, thereby indicating that the bile preparation substantially free of pus or blood.

In a preferred embodiment of the method, bile from bovine sources is utilized. Bovine bile is plentiful, because, in part, relatively large quantities can be extracted from each animal. Moreover, bovines are routinely slaughtered and inspected under health-related regulations, thus such animals provide a reliable source for preparing the composition of the invention. Furthermore, humans are less likely to have an allergic reaction to material of bovine origin.

The bile is mixed with an equal volume of an alcohol to produce a bile/alcohol solution, which is 50% alcohol. The alcohol may be an aliphatic alcohol, preferably methanol, ethanol, or propanol, most preferably ethanol.

A solution that is substantially free of the 50% alcohol-insoluble material may be isolated by centrifuging. Preferably, the bile/alcohol mixture is centrifuged at 3000–5000 rpm, most preferably 4200 rpm, for at least 2 hours, at about 15–25° C. The alcohol contained in the bile/alcohol-soluble fraction then may be removed by taking advantage of the different volatility of alcohol and water, using conventional methods, i.e., heating the fraction to a suitable temperature, e.g., 80–85° C., for a suitable amount of time, e.g., up to about 10 hours.

Bile pigments may be removed from the solution to obtain a clear, yellowish liquid by using activated charcoal, polyamidic microgranules, or filtration. Preferably, an activated charcoal treatment is utilized. The procedure may be repeated in order that the solution satisfies optical density and conductivity standards.

The clear, yellowish liquid is treated to remove substantially any residual alcohol, using conventional methods. Preferably the clear, yellowish liquid is filtered using a filter having about a 1.0–3.5 μm retention, most preferably a retention of 2.5 μm.

The clear, yellowish liquid is then extracted with ether and the aqueous phase is isolated. The ether used in this step is preferably dimethyl ether, ethyl ether, n-propyl ether, iso-propyl ether, or n-butyl ether, most preferably ethyl ether.

Residual ether may be removed from the aqueous phase by, for example, heating the solution up to 55° C., preferably up to about 40° C. for about 5–15 hours, most preferably for about 10 hours.

The composition may be used without further modification simply by packaging it in vials and sterilizing. The composition also may be used in a concentrated form. A preferred concentrated form is prepared as follows. Prior to step (e) described hereinabove, the clear, yellowish liquid optionally may be concentrated to about one eighth of the volume of the bile/alcohol solution by, for example, heating to a temperature of less than about 85° C., preferably, to about 60°–70° C. After step (f), the aqueous phase may be concentrated so that it is one tenth of the volume of the bile/ethanol solution by, for example, heating to about 80–85° C.

In a preferred method to prepare a composition of the invention, the collected bile is mixed with an equal volume of ethyl alcohol. The bile/alcohol mixture is then centrifuged at about 4200 rpm for at least 2½ hours, at about 20±2° C. The supernatant liquid is decanted and checked for pH and ethanol content. Bile pigments are then removed using activated charcoal. The treated bile/ethanol solution is then monitored for optical density (O.D.) and conductivity. O.D. levels or conductivity levels outside acceptable specifications require that the bile/ethanol solution be given additional treatment to remove bile pigments, for example treatment again with activated carbon to achieve a reading within specification limits.

Following activated carbon treatment, the solution is filtered through a filter having a 2.5 μm retention, the alcohol is evaporated off by heating to less than 85° C. and the solution is concentrated to approximately one eighth of the original bile/ethanol solution volume. The concentrated solution is cooled to between about 20–25° C. This solution is then mixed with ethyl ether and the ether phase is discarded. Preferably, relatively small volumes of ether and strong agitation are used, such as 0.1 to 1 volume, preferably 0.2 to 0.5 volume. This step may be repeated once. The aqueous phase is heated to remove residual ether by heating up to 55° C. for about 10 hours, and further reduced in volume to one tenth of the original bile/ethanol volume by heating to about 80–85° C. This solution is then tested for appearance, biological activity, and ethanol and ether content.

The pH of the composition may be adjusted to physiological pH, i.e. 7.4–7.5, using hydrochloric acid (1%) solution and sodium hydroxide (1% solution), and a buffered solution may be obtained using dibasic and monobasic sodium phosphate salts as buffers, using conventional methods.

The composition may be used without further modification by simply packaging it in vials and sterilizing. A preferred sterilization method is to subject the composition to three sterilization cycles by autoclaving followed by incubation.

The composition may be used in a concentrated form. The preparation of the concentrated form is described above. The composition may also be lyophilized.

The composition and concentrated composition are clear yellowish solutions essentially free of foreign matter, containing not more than 10 ppm ethanol and not more than 5 ppm ether. The compositions activate PBMNs to release TNF in vitro as measured by the Monocyte/Macrophage Activation Assay (TNF-Release) as described in Example 2. Moreover, the compositions activate PBMN's from, for example, a cancer patient, which then mediates cytocidal activity against cancerous cells derived from the same patient. Indeed, clinical studies involving animals and humans have shown efficacy in anti-tumor treatments using the composition of the present invention. Similarly, PBMN's activated with the composition have been shown to act upon endometrial cells such that the use of the composition to treat endometriosis and other inflammatory diseases is provided by the present invention.

Figure 2:
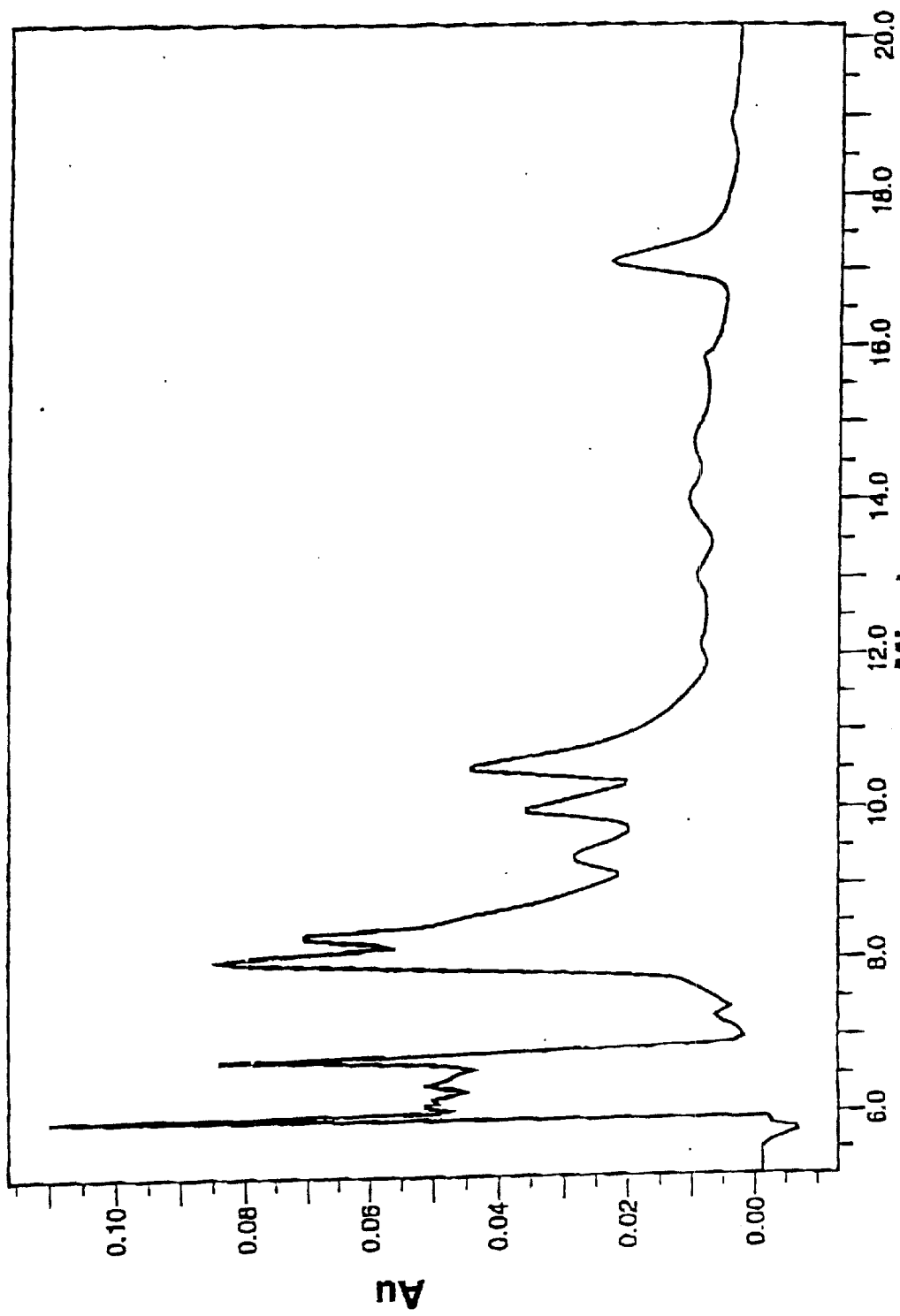
FIG. 2 is an RP-HPLC profile for a concentrated composition of the invention.
Figure 3:
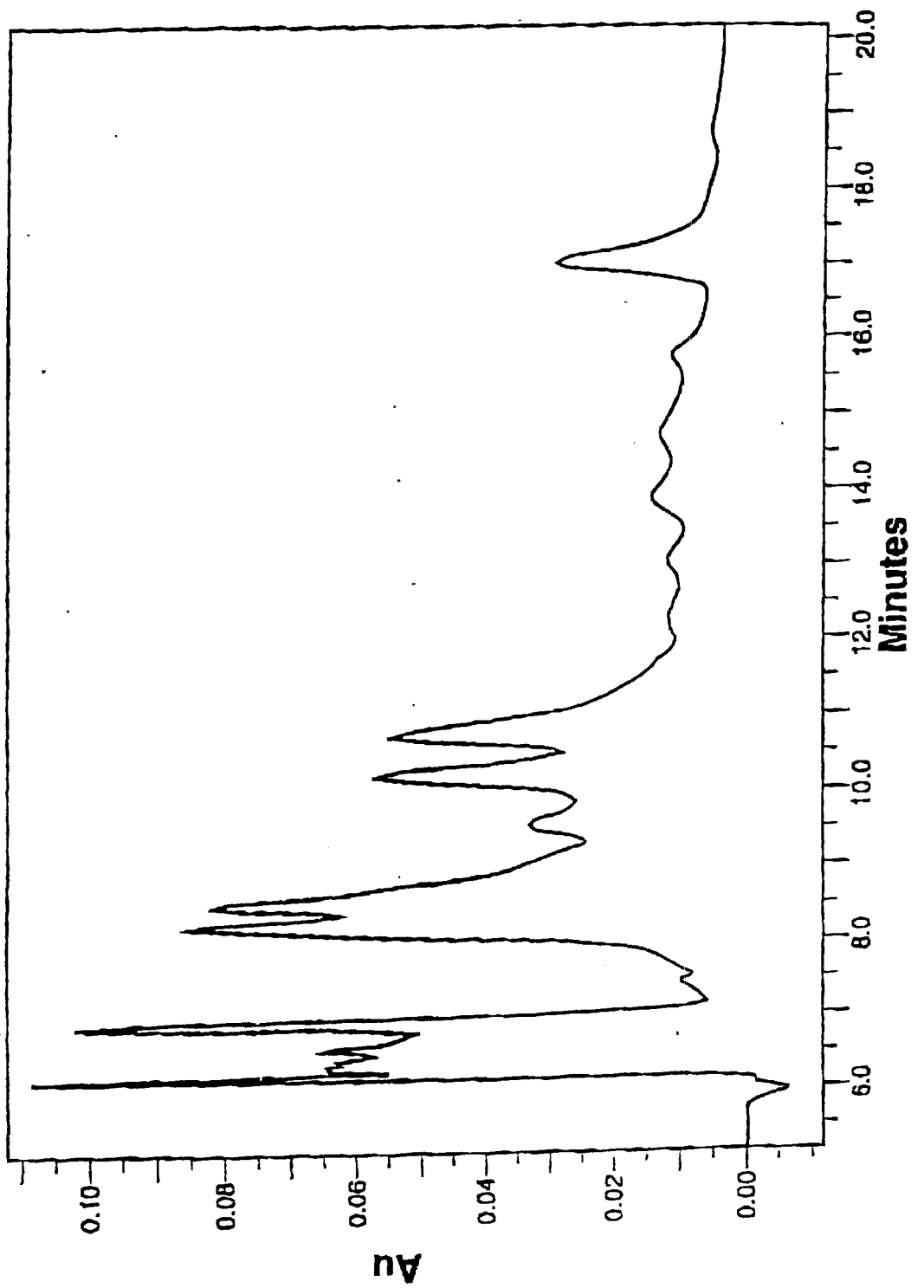
FIG. 3 is a RP-HPLC profile for a concentrated composition of the invention.
Figure 4:
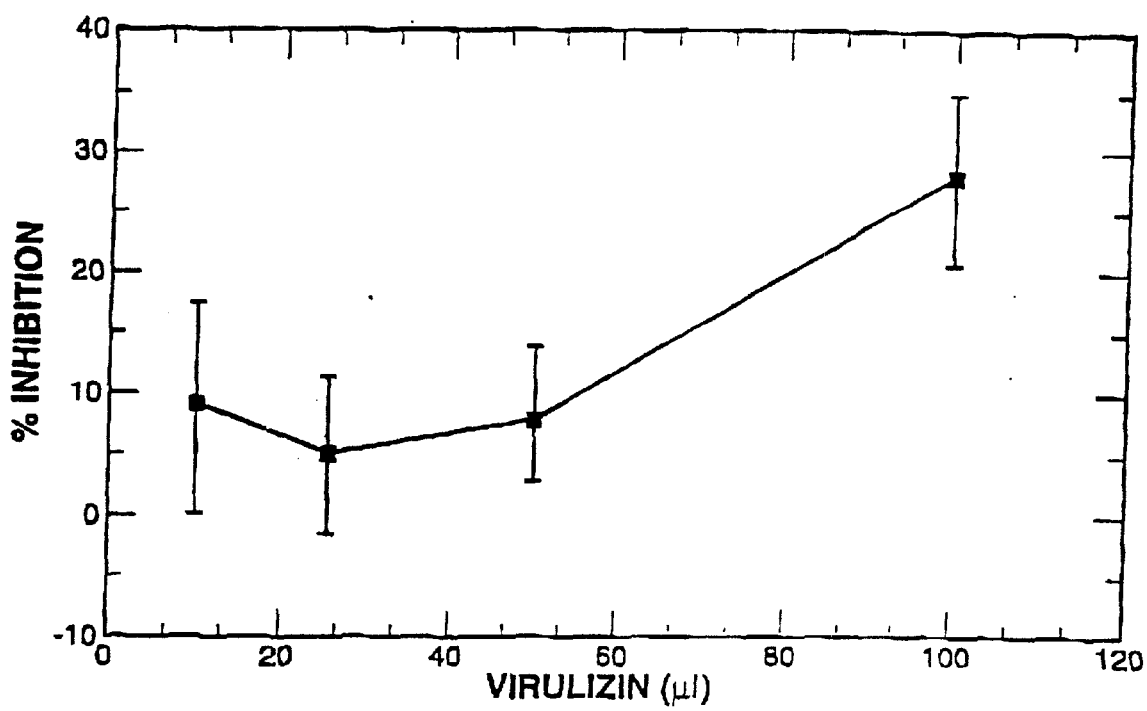
FIG. 4 is a graph showing the effect of the composition on LPS-induced release of TNF by peripheral blood mononuclear cells (PBMNs)

The compositions of the invention can be produced in a consistently reproducible form using the method as generally described above with demonstrated identity, potency and purity from batch to batch. Identity and purity are determined using reverse-phase high pressure liquid chromatography. (See Example 1). The compositions of the invention have a consistently reproducible pattern on reverse-phase HPLC The HPLC readings for three lots of the concentrated composition of the invention are shown in FIGS. 1 to 3. The compositions are also characterized by the properties hereinbefore mentioned, for example their ability to stimulate monocytes and macrophages in vitro and in vivo, etc.

Compounds likely to be present in the present composition, considering the source, include sulfonated bile acids, oxidized bile acids, other naturally occurring bile acids, and their amino acid (especially glycine and taurine) conjugates and sterols. Accordingly, it is believed that the present composition includes at least one compound having the formula

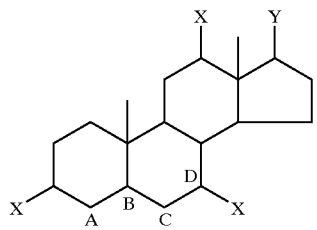

wherein the molecule may or may not be fully saturated, such that, for example, the bond between A and B, B and C, or C and D may be single or double bonds, and wherein X is H, OH, =O, or $OSO_3H$; and Y is

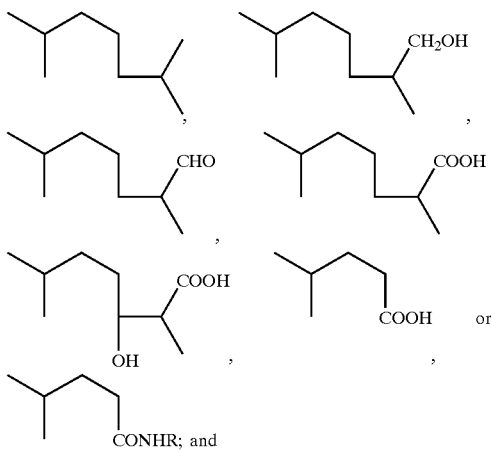

wherein R is an amino acid residue, such as, for example, glycyl, glutamyl, or tauryl, thereby forming the glycine, glutamyl, or taurine conjugate.

In particular, the composition of the present invention has been analyzed as to its component compounds, including organic and inorganic components. Such information was derived using standard methods of analytical chemistry, including mass spectroscopy (MS). The results of such studies include, for example, the identification of specific bile acid compounds thought to be present, including cholic acid, glycocholic acid, deoxyglycocholic acid, ursodeoxycholic acid, cholesterol sulfate, deoxycholic acid, chenodeoxycholic acid, and taurocholic acid.

From the MS it is not distinguishable if the loss of OH and $H_2$ of some compounds are occurring in the MS or if the deoxy, dideoxy and unsaturated analogs of such compounds are also present to begin with. These compounds may all be present as salts of ammonium, aklylammonium and inorganic cations.

The MS analysis also supports the identification in the present composition of phospholipids, sphingolipids and related agents capable of forming miscelles. Specific compounds thought to be present include:

stearic acid $CH_3(CH_2)_{16}COOH$
palmitic acid $CH_3(CH_2)_{14}COOH$
oleic acid Z-9 octadecanoic acid $CH_3(CH_2)_2$ $CH_2CH=CHCH_2(CH_2)_6COOH$
oxidized or hydroxylated/unsaturated short chain fatty acids: $C_6H_8O_3$ (e.g., $CH_3CH=CHCOCH_2COOH$ or a $C_6$ acid with 2 double bonds and a hydroxide)
acetic acid
stearic acid diglyceride
palmitic acid diglyceride
stearic acid, palmitic acid diglyceride
stearic acid-monoglyceride-phosphocholine (a lysolecithin)
stearic acid monoglyceride
stearic acid triglyceride
palmitic acid monoglyceride
phosphocholine
phosphoserine
phosphosphingosine
sphingomyelin
phosphoglycerol
glycerol
stearic acid-sphingosine
sphingosine
stearic acid amide
stearic acid methylamide
choline
glycerophosphocholine
stearic acid, oleic acid diglyceride
stearic acid, oleic acid phosphoglycerol
palmitic acid amide
lecithin
sialic acid-glycerol dimer In addition, preliminary HPLC and titration evidence has been obtained which shows that shorter chain fatty acids are also present, such as those having from 1 to about 30 carbon atoms.

Phospholipid, sphingolipid, and related hydrolysis product compounds likely to be present considering the source and the information derived from the MS and HPLC analyses include at least one compound having the formula

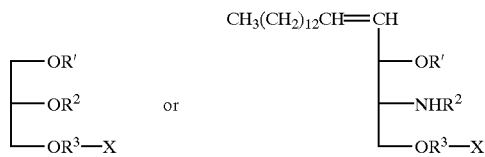

where $R'$, $R^2$, $R^3$ are different or the same and are H, $COR^4$, $CH=CH-R^5$, X, $-P(O)(OH)O-$, or $-S(O)_2$ O—; X is selected from the group consisting of choline, ethanol amine, N-alkylated ethanolamines, serine, inositol, sugars bearing free hydroxyls, amino-sugars, sulfonated sugars, and sialic acids; $R^4$ is $C_1-C_{30}$ alkyl that is saturated or unsaturated, oxidized or hydroxylated; and $R^5$ is an alkyl group or oxidized and/or hydroxylated analogs thereof.

The fatty acids and their conjugates may be present in the aforementioned aqueous extract as salts. The solubility of such compounds is also enhanced by other components of the mixture. Amides of the included carboxylic acids, $RCONR'R^2$, where R' and $R^2$ are the same or different and are H or alkyl, are also believed to be present.

A third class of compounds, namely, mucin and proteoglycan hydrolysis products, are also likely to be present, considering the source of the composition and the aforementioned MS analysis thereof. Such compounds include hydrolysis products of mucoproteins from bile and from the gallbladder wall, such as: chondroitin 4- and 6-sulfates, dermatan sulfate, heparin, heparin sulfate, hyaluronic acid and the hydrolysis products (monomers, dimers, oligomers and polymers) of these mucins. Chitin and other mucins may be similarly hydrolyzed, which hydrolysis products would include:

N-acetyl-D-glucosamine, N-acetyl-D-galactosamine-4-sulfate, galactose-6-sulfate, N-acetyl-D-glucosamine-6-sulfate, glucosamine-6-sulfate, D-glucosamine 2-sulfate, D-glucosamine 2,3-disulfate, D-galactose-6-sulfate, glucuronic aid 2-sulfate, N-acetylneuraminic acid, sialic acid, N-acetyl chondrosine, chondroitin 4-sulfate, chondroitin 6-sulfate, D-glucosamine, D-galactosamine, glucuronic acid, glucose, galactose, mannose, fucose, iduronic acid, hexose, hexosamine, ester sulfate, glucuronic acid, chondrosamine, 2-amino-2-deoxy-D-galactose, serine, proline, threonine, alanine glycine taurine, glutamic acid, aspartic acid, histidine, and small peptides.

Similar products would be obtained by hydrolysis of mucins such as keratin sulfates, dermatan sulfates the natural sugar-sugar linkages in the dimers, oligomers and polymers may be replaced by —O—Si(OH)$_2$—O— bridges between the sugar monomers or adjacent sugar chains.

In particular, specific mucin and proteoglycan hydrolysis product compounds thought to be present include:

sialic acids and their mono and diacetylated and glycolylated monomers;

N-acetylneuraminic acid;

hexosamines, such as glucosamine;

L-fucose;

hexosamine-hexuronic acid (dimer) disulfate;

glucuronic acid;

glucuronic acid or iduronic acid disulfate, monoacetylated;

sialic acid-glycerol (dimer); and dimers, trimers, oligomers and polymers of the above monomers in acetylated and sulfated form.

A fourth class of compounds, namely fat-soluble vitamins, likely to be present considering the source and the aforementioned MS analysis, include A, D, and K vitamins (e.g., A2, D1, D3, D4, K1, K2, K5, K6, K7, K-S(II), and Vitamin E acetate, for example.

In particular, specific fat-soluble vitamin compounds thought to be present include at least one of the group consisting of Vitamin A2, Vitamin D1, Lumisterol (present from its vitamin D1 complex), Vitamin E, Vitamin K1 oxide, and Vitamin K5.

Various miscellaneous organic compounds are likely to be present, considering the source and the aforementioned MS analysis. Such compounds include:

urea;

alkylamines, including methylamine, dimethylamine, ethylamine, methylethylamine, diethylamine, dipropylamine, and/or butylethylamine;

amino acids, including taurine, glutamic acid, glycine, alanine, n-leucine, phosphoserine, phosphoethanolamine, aspartic acid, threonine, serine, sarcosine, α-amino adipic acid, citrulline, valine, isoleucine, β-alanine, γ-amino butyric acid, hydroxylysine, ornithine, and lysine;

bilirubin, and its gluconuride conjugate;

biliverdin, and its gluconuride conjugate;

butylatedhydroxy toluene (BHT);

polyethylene glycol;

traces of steroids;

other plasma solutes, such as sugars, purines and pyrimidines;

miscellaneous dietary lipids; and glutathione and its hydrolysis products.

In particular, specific miscellaneous organic compounds believed to be present in the composition include at least one of the group consisting of urea, methyl amine, dimethylamine, ethylamine, methylethylamine, diethylamine, dipropylamine, butylethylamine, ammonia, choline, taurine, glutamic acid, glycine, alanine, p-ser, p-eu, p-ea, asp thr ser sar, a-aba, cit, val, ile, leu, B-ala, G-aba, OH-lys, orn, lys, butylated hydroxy toluene (BHT), and polyethylene glycol.

Amines present in the present composition, particularly the secondary amines, may include nitrogen oxides from the air, thus forming nitroso compounds. N-oxides and N-carbamate byproducts may also be included. This series of amines cited above should be extended to include all primary, secondary and tertiary alkylamines.

Certain inorganic elements have been identified and quantified (mg/l) as follows:

| | |
|---|---|
| Tungsten | 0.07 |
| Zinc | 0.666 |
| Phosphorus | 378 |
| Cadmium | 0.01 |
| Cobalt | 0.008 |
| Nickel | 0.022 |
| Barium | 0.032 |
| Iron | 0.022 |
| Manganese | 0.039 |
| Chromium | 0.060 |
| Magnesium | 7.46 |
| Aluminum | 0.136 |
| Calcium | 5.97 |
| Copper | 0.087 |
| Titanium | 0.01 |
| Strontium | 0.060 |
| Sodium | 9600 |
| Potassium | 483 |
| Chloride | 15400 |
| Ammonia | 218 |
| Vanadium | 1 ppm |

The compositions of the invention have valuable pharmacological properties. In particular, the compositions of the invention effect neoplastic growth, effect release of tumor necrosis factor, and activate macrophages and monocytes. The compositions have been shown to cause no significant toxicity and only transient adverse side effects (for example, slight fever, polydipsia, pain at injection site). They have also been found to contain no detectable components of high molecular weight matter (i.e., above about 5,000 daltons), which can cause harmful immunologic reactions. The compositions may be used as agents for the prophylaxis and treatment of conditions requiring modification of the immune response, in particular infectious diseases (including bacterial, fungal, protozoal, and other opportunistic infections), inflammations (including endometriosis and inflammatory bowel disease), vaccinations (including use as an adjuvant for HIV; routine childhood and adult immunizations such as diptheria, pertussis, tetanus, polio, measles, mumps, rubella, viral influenza, and haemophilus; and traveller's vaccines such as typhoid, cholera, plague, bacterial meningitis, and malaria), neoplasias, and autoimmune diseases. Such diseases are associated with, and may be the direct result of, an inadequate immune system response. As noted in the Background section above, both humoral and cellular defects may be involved. The present invention, in view of its exemplified ability to activate monocytes and macrophages, can enhance both of these aspects of the immune response. Additionally, the composition of the present invention can be used to ameliorate or block rejection phenomena associated with organ transplant whether intra- or inter-species. The inventive composition may also be used to treat radiation sickness.

Accordingly, the compounds of the present invention may be especially useful in the treatment of various forms of neoplasia, such as leukemias, lymphomas, melanomas, adenomas, sarcomas, and carcinomas. In particular, the composition may be useful for treating malignant melanoma, pancreatic cancer, cervico-uterine cancer, cancer of the kidney, stomach, lung, rectum, ovary, breast, bowel, gastric, liver, thyroid, neck, cervix, salivary gland, leg, tongue, lip, bile duct, pelvis, mediastinum, urethra, bronchogenic, bladder, esophagus and colon, and Kaposi's Sarcoma, which is a form of cancer associated with HIV-infected patients with Acquired Immune Deficiency Syndrome (AIDS). The composition may also be used for other conditions that either cause or are encouraged by a defective immune response, such as arthrosclerosis, and opportunistic or other infections, such as viral infections, in particular AIDS. It may also be used in the treatment of autoimmune diseases, including multiple sclerosis, rheumatoid arthritis, systemic lupus erythematosus, Type I diabetes, myasthenia gravis, Addison's Disease, autoimmune hemolytic anaemia, Crohn's disease and other inflammatory bowel diseases, Goodpasture's syndrome, Graves' disease, Hashimoto's thyroiditis, idiopathic thrombocytopenic purpura, pernicious anaemia, poststreptococcal glomerulonephritis, psoriasis, scleroderma, Sjogrens's syndrome, spontaneous infertility, and pemphigus vulgaris. The composition may further be used to treat inflammatory diseases, such as endometriosis and inflammatory bowel disease.

The compositions of the invention may be converted using customary methods into pharmaceutical compositions. The pharmaceutical composition contain the composition of the invention either alone or together with other active substances. Such pharmaceutical compositions can be for oral, topical, rectal, parenteral, local, inhalant, or intracerebral use. They are therefore in solid or semisolid form, for example pills, tablets, creams, gelatin capsules, capsules, suppositories, soft gelatin capsules, gels, membranes, and tubelets. For parenteral and intracerebral uses, those forms for intramuscular or subcutaneous administration can be used, or forms for infusion or intravenous or intracerebral injection can be used, and can therefore be prepared as solutions of the compositions or as powders of the active compositions to be mixed with one or more pharmaceutically acceptable excipients or diluents, suitable for the aforesaid uses and with an osmolarity that is compatible with the physiological fluids. For local use, those preparations in the form of creams or ointments for topical use or in the form of sprays may be considered; for inhalant uses, preparations in the form of sprays, for example nose sprays, may be considered. Preferably, the composition is administered intramuscularly.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in *Remington's Pharmaceutical Sciences* (Nack Publishing Company, Easton, Pa., USA 1985).

On this basis, the pharmaceutical compositions include, albeit not exclusively, the composition of the invention in association with one or more pharmaceutically acceptable vehicles or diluents, and are contained in buffered solutions with a suitable pH and iso-osmotic with the physiological fluids.

The compositions are indicated as therapeutic agents either alone or in conjunction with other therapeutic agents or other forms of treatment. For example, in the case of a malignant tumor, the present treatment may render a tumor suitable for surgical removal where it was not previously operable. Alternatively, the present treatment may be usefully combined with chemotherapy and/or radiotherapy. The compositions and agents of the invention are intended for administration to humans or animals.

In general, a dosage range of the composition is envisaged for administration in human medicine of from about 0.01 to 20 mg/kg, preferably from about 0.1 to 10 mg/kg, most preferably 0.1 to 1 mg/kg of body weight daily may be employed. In the case of intravenous administration, the dosage is about 0.1 to 5 mg/kg of body weight daily, and in the case of oral administration the dosage is about 1 to 5 mg/kg of body weight daily. Where the concentrated composition is used, approximately half the above mentioned dosages may be used. For example, for intramuscular administration, a dosage of about 0.2 to 1.0 mg/kg of body weight daily, preferably 0.275–0.75 mg/kg of body weight daily may be used.

It will be appreciated by medical practitioners that it may be necessary to deviate from the amounts mentioned and, in particular, to do so as a function of the body weight and condition of the animal to be treated, the particular disease to be treated, the nature of the administration route and the therapy desired. In addition, the type of animal and its individual behavior towards the medicine or the nature of its formulation and the time or interval at which it is administered may also indicate use of amounts different from those mentioned. Thus it may suffice, in some cases, to manage with less than the above-mentioned minimum amounts while in other cases the upper limit mentioned must be exceeded. Where major amounts are administered, it may be advisable to divide these into several administrations over the course of the day.

Thus, the present invention comprises a process for preparing an immunomodulator composition comprising (a) mixing bile from an animal with a water-soluble solvent to produce a bile/solvent solution; (b) isolating an aqueous solution substantially free of solvent from the bile/solvent solution; and (c) removing bile pigments from the substantially solvent-free solution to obtain a clear, yellowish liquid, preferably where the water soluble solvent is an alcohol, and where the bile from the animal is mixed with an equal volume of the alcohol. Preferred aspects of the aforementioned process also comprise further concentrating the clear, yellowish liquid to about one-eighth, or one-tenth, the original volume of the bile/solvent solution. Obviously, compositions produced via the above process form a preferred aspect of the invention.

The present invention also comprises a composition for use as an immunomodulator, comprising at least one component having a molecular weight of less than about 3000 daltons, which shows no cytotoxicity to human peripheral blood mononuclear cells, and has at least one of the following properties:
(a) is capable of stimulating monocytes and macrophages in vitro or in vivo to produce one or more cytokines; or
(b) is capable of stimulating monocytes or macrophages to produce tumor necrosis factor in vitro or in vivo; or
(c) has an anti-proliferative effect in a malignant cell line; and
wherein said component is not an endotoxin, IL-1α, IL-1β, TNF, IL-4, IL-6, IL-8, GM-CSF or IFN-γ. Such compositions may be obtained from the bile of animals, preferably bovines, or from other sources as noted above. In a preferred embodiment of the composition, the composition stimulates tumor necrosis factor production in vitro or in vivo, and most preferably in humans, in the absence of exogenous IL-1α, IL-1β, TNF, IL-4, IL-6, IL-8, GM-CSF, and IFN-γ.

The compositions of the present invention also have components that can be characterized by column chromatography such that when said composition is dried to obtain a solid residue, and 2 grams of said residue are dissolved in 20 ml of a 10% concentrated ammonium hydroxide solution in methanol, and after any insoluble material is removed, is subjected to column chromatography in a methanol column having dimensions of 5 cm×12.5 cm, and containing 102 g of 60 A flash silica gel, and operating at a pressure of 10 pounds per square inch and a flow rate of 11 ml/min with a 10% concentrated ammonium hydroxide in methanol solvent solution, said component is eluted from the column in a fraction taken when the total column elution is between about 180 and about 220 ml, between about 220 ml to about 260 ml, or between about 260 ml and about 300 ml.

Characterization of components may also be accomplished by ion-exchange chromatography, such that when 10 ml of said composition is subjected to anion-exchange chromatography in a column containing Bio-Rad AG-1 hydroxide form resin in an amount sufficient to bind substantially all the anions present in said 10 ml of said composition, said component is eluted from the column using a step gradient of ammonium bicarbonate buffer at a buffer concentration from about 0.1 M to about 1.5 M, preferably at a buffer concentration from about 0.2 M to about 0.4 M, and most preferably at a buffer concentration of about 0.2 M.

Reversed-phase (C18) HPLC can also be used for characterization of components. Other suitable columns, eluents, gradients, flow rates, operating temperatures and detection systems may be used.

The compositions of the present invention can also be characterized by TLC, such that when said composition is subjected to thin layer chromatography on silica gel plates in a suitable solvent system, such as 10% concentrated ammonium hydroxide in methanol, and visualized with a suitable spray, such as ninhydrin; a positive reaction with ninhydrin occurs at, for example, an $R_f$ value from about 0.80 to about 0.90.

The present invention also comprises a method of stimulating tumor necrosis factor production in humans, comprising administering an effective amount of a composition comprising at least one of the following compounds:

(a) a compound of the formula

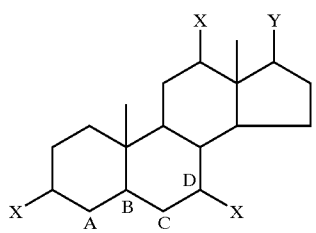

where the bonds between A—B, B—C, and C—D may be single or double bonds, and where X=H, OH, =O, or $OSO_3H$; and

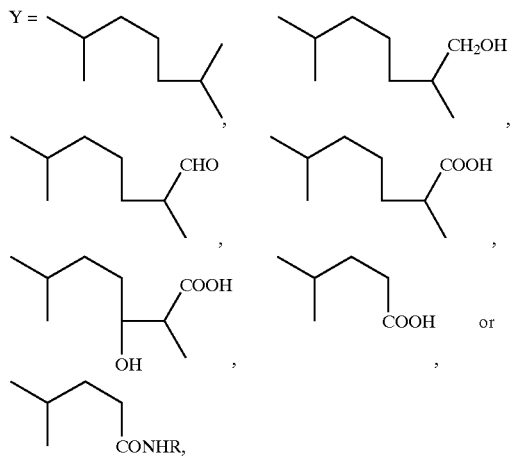

where R is an amino acid residue;

(b) a compound of the formula

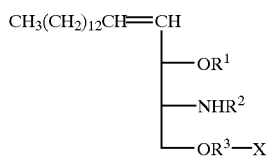

where $R^1$, $R^2$ and $R^3$ are H, $COR^4$, CH=CH—$R^5$, X, P(O)(OH)O—, or —S(O)$_2$O—;

X is choline, ethanolamine, N-alkylated ethanolamines, serine, inositol, sugars bearing free hydroxyls, amino-sugars, sulfonated sugars, or sialic acids; and $R^4$ is a saturated or unsaturated alkyl group having a carbon chain from about $C_1$ to $C_{30}$, or oxidized and hydroxylated analogs thereof; and $R^5$ is an alkyl group or oxidized and hydroxylated analogs thereof;

(c) a mucin hydrolysis product or a proteoglycan hydrolysis product; or (d) a fat-soluble vitamin.

Preferably, compositions of the inventive method comprise at least one compound selected from the group consisting of taurocholic acid and its sulphated derivatives; glycocholic acid and its sulphated derivatives; sphingosine; a diacyl glycerol; lecithin; phosphocholine; phosphoglycerol; glycero-phosphocholine; phosphoryl choline chloride; an oligosaccharide of less than 10 saccharide units in length, where said oligosaccharide is comprised of sialic acid, fucose, hexosamines, or sulphated hexosamines; Vitamin A; retinolic acid derivatives; retinol derivatives; taurine; and glutamic acid and its conjugates. The composition may also additionally comprise at least one compound selected from the group consisting of ammonia; primary alkyl amines; secondary alkyl amines; tertiary alkyl amines; and a carboxylic acid $R^6CO_2H$, wherein $R^6$ is $C_1$–$C_{30}$ alkyl that is saturated or unsaturated, and oxidized and/or hydroxylized derivatives thereof. More preferably, such a composition comprises at least one of the group consisting of phosphocholine, glycero-phosphocholine, glucosamine-3-sulfate, and phosphorylcholine chloride. Most preferably, the composition comprises at least one of the following: phosphocholine, glycero-phosphocholine, or glucosamine-3-sulfate.

The method of the invention also embraces stimulation of TNF production by administration of a composition comprising at least one compound selected from the group consisting of taurocholic acid and its sulphated derivatives; glycocholic acid and its sulphated derivatives; sphingosine; a diacyl glycerol; lecithin; an oligosaccharide of less than 10 saccharide units in length, where said oligosaccharide is comprised of sialic acid, fucose, hexosamines, or sulphated hexosamines; Vitamin A; retinoic acid derivatives; retinol derivatives; taurine; and glutamic acid and its conjugates.

The present invention also provides a method of treating cancer, including carcinomas of the pancreas, ear/nose/throat, ovaries, lung, or endometrium, as well as chronic myelogenous leukemia and Kaposi's sarcoma, wherein the method comprises administering to a patient suffering from the cancer a therapeutically effective amount of the compositions of the invention. The present invention also provides a method for treating other disorders that are caused by or result from an impaired immune system response, including inflammatory disease, including endometriosis and inflammatory bowel disease, autoimmune disease, including rheumatoid arthritis, lupus, multiple sclerosis, and ALS, infectious disease, including bacteria, fungal, mycoplasma, protozoal, and other opportunistic infections, wherein the method comprises administering to a patient afflicted by one of the aforementioned diseases a therapeutically effective amount of the composition of the invention. Moreover, the present invention provides a method of vaccination for prophylaxis against HIV, various childhood diseases, and others, wherein the composition of the present invention is added to such a vaccine as an adjuvant.

Also forming part of the present invention are compositions comprising (1) micelles of sphingosine or sphingosine complexed with a salt, or (2) micelles of retinolic acid or its derivatives, which have at least one of the following properties:

(a) is capable of stimulating monocytes and macrophages in vitro to produce one or more cytokines;

(b) is capable of stimulating monocytes or macrophages to produce tumor necrosis factor in vitro or in vivo; or (c) has an anti-proliferative effect in a malignant cell line.

The micelles may also comprise a diacyl glyceride or lecithin, and may further comprise a bile acid salt, and a source of ammonium or alkyl ammonium ions.

Finally, the present invention also contemplates compositions comprising (1) sphingosine, a bile acid salt and a source of ammonium or alkyl ammonium ions, (2) a bile acid salt, sphingosine, a diacyl glycerol, a source of ammonium or alkyl ammonium ions, and a retinol derivative, (3) a diacyl glyceride, lecithin, and a bile acid salt, or (4) (a) a diacyl glyceride, (b) lecithin, and (c) a mucin hydrolysis product or a proteoglycan hydrolysis product, which has at least one of the following properties:

(a) is capable of stimulating monocytes and macrophages in vitro to produce one or more cytokines;

(b) is capable of stimulating monocytes or macrophages to produce tumor necrosis factor in vitro or in vivo;

(c) has an anti-proliferative effect in a malignant cell line.

The following non-limiting examples are illustrative of the present invention:

EXAMPLE 1

This example describes and illustrates preparation of the composition of the invention.

Bovine bile was collected from the gall bladders removed from healthy cows (both males and females) that were at least one and one-half years old. These cows were slaughtered for food use at a licensed and inspected abattoir. The slaughtered animals had been inspected and evaluated as healthy prior to slaughter and the gall bladders were separated from the livers and examined by a veterinarian to confirm that the gall bladders were free of parasites and evidence of infection, and thus suitable for use as a source of bile for the present invention.

Gall bladders that passed this inspection were subjected to the following procedure:

Gall bladders were wiped with a solution of 70% ethanol to sanitize the exterior of the bladders and bile was removed from the bladders with a syringe. The bile removed was visually examined in the syringe by the veterinarian to assure that it contained no blood or pus and was otherwise satisfactory. Bile from a healthy bovine is a greenish fluid substantially free of blood and pus. Fragments of livers, spleen, and lymph nodes were also collected from the animals whose bile was collected and the fragments were examined for the presence of parasites and other indications of disease.

For species that do not have a defined gall bladder (such as shark), bile is obtained directly from the hepatic organ.

Bile found to be satisfactory was transferred into a graduated amber bottle containing ethanol to give a 50% bile/50% ethanol solution by volume. The bile/ethanol solution was a greenish fluid substantially free of foreign material and tested positive for ethanol in accordance with methods recited at United States Pharmacopeia XXII, Part B (1994). These bottles were labelled with a lot number. Bile collected from a minimum of fifty animals was collected for each lot.

The bile/ethanol solution was then centrifuged at 4200 rpm for at least 2½ hours at 20±2° C. The supernatant liquid was decanted, filtered through a filter having, for example, a 2.5 $\mu$m retention, and checked for pH and ethanol content. The decanted liquid was then subjected to an activated charcoal treatment. The treated liquid was then monitored for Optical Density (OD) at 280 nm and conductivity. OD levels and/or conductivity levels outside specified ranges necessitated additional treatment of the liquid with activated carbon to achieve an OD and conductivity within specified ranges.

Following activated carbon treatment, the treated liquid filtered through a filter having, for example, a 2.5 $\mu$m retention, the ethanol was evaporated off (for example, by heating up to about 85° C.), and the treated liquid was concentrated to approximately one-eighth of the original bile/ethanol solution volume. The concentrated liquid was then cooled to 20–25° C., filtered through a filter having, for example, a 2.5 $\mu$m retention, and mixed with ethyl ether and the ether phase was discarded. This step can be repeated once. The aqueous phase was heated to remove residual ether (for example, by heating up to about 55° C. for about 10 hrs) and further reduced in volume to one-tenth of the original bile/ethanol volume by heating to around 80–85° C. The resultant composition was then tested for appearance, biological activity, and ethanol and ether content. The composition was a clear, yellowish solution, essentially free of foreign matter, and contained less than 10 ppm ethanol and less than 5 ppm ether.

Identity and purity were determined using reverse-phase high pressure liquid chromatography (reverse-phase HPLC). Potency is assayed using the monocyte/macrophage activation test referred to herein as the peripheral blood mononuclear cell-tumor necrosis factor assay (PBMN-TNF assay or, simply, TNF assay), as described in Example 2.

Initial batches of the composition of the invention were manufactured as a non-buffered liquid. Subsequent batches were manufactured as a buffered liquid, prepared by adjusting the pH of the composition to about 7.4±0.2, using hydrochloric acid (1%) solution and sodium hydroxide (1% solution), as well as using dibasic and monobasic sodium phosphate salts as buffers. Bioburden reduction was conducted in a steam autoclave at 104±2° C. for 60 mins. The bulk solution was filled into 5 ml or 10 ml sterile bottles and capped. The filled and capped bottles were subjected to three sterilization cycles by autoclaving them at 104° C.±2° C. for 60 mins followed by incubation at 35° C. for 23±1 hrs. Between each cycle of sterilization (autoclave plus incubation), samples were taken and tested for bioburden. Following the last cycle of sterilization, the bottles were visually inspected against a black and a white background to detect the presence of particulates.

Following inspection, the lot was sampled and tested for conformance to specifications. Tests included identity, sterility, pyrogenicity, endotoxin, bioassay, HPLC and general safety. Table I summarizes the data obtained for the various tests performed on the bile extract of the present invention, including normal ranges of data, where appropriate.

for TNF-α, IL-1α, IL-2, IL-4, IL-6, IL-8, GM-CSF and IFN were conducted. These studies provided the basis for a standardized test for quantitatively evaluating the potency of a given batch of bile extract prepared according to Example 1, which test evaluates the ability of the bile extract, or a component or components thereof, to stimulate TNF-α production in the PBMN or U937 cells.

Whole blood was drawn from 5 healthy human subjects into heparinized Vacutainer tubes (Beckton Dickinson, Canada). PBMNs were isolated by gradient centrifugation on Ficoll-Hypaque (Pharmacia). The PBMNs were washed twice with phosphate-buffered saline (PBS), counted and resuspended in RPMI 1640 culture medium (Gibco Labs) at a concentration of $10^6$ cells/0.5 ml. These cells were cultured in 24-well, flat-bottomed tissue culture plates (Falcon, Becton, Dickinson). A 0.5 ml aliquot of the PBMN suspension was added to each well, which contained 50 ng lipopolysaccharide (LPS) (from $E.\ coli$), 10 µl fetal calf serum and 10–300 µl of the composition of Example 1, as noted in the tables below. The hyperosmolar effect of the composition was neutralized by adding distilled water to the culture wells at a volume equivalent to 10% of the volume of composition used. The total volume was then made up to 1 ml/well with RPMI. PBS was used as a control. The cells were cultured for 2, 6, 24, 48 and 72 hrs at 37° C. in a humidified 5% $CO_2$ incubator. At the end of each incubation period, the cells were harvested and cell-free culture fluids were obtained by centrifugation at 9000 rpm for 10 mins.

TABLE I

Characteristics of Batch Compositions
Obtained In Accordance with Method of Example 1

| FINAL PRODUCT TEST | BATCH # BC0248 | BATCH # BC0249 | BATCH # BC0250 |
|---|---|---|---|
| Potency (pg/ml)* | 210 | 183 | 304 |
| Identity/Purity Agrees with reference | Pass | Pass | Pass |
| Safety (passes test according to 81 CFR § 610.11) | Pass | Pass | Pass |
| Pyrogenicity (temp. increase shall not exceed 0.4° C.) | Pass | Pass | Pass |
| Endotoxin ≦0.4 EU/ml | ≦0.25 | ≦0.25 | ≦0.25 |
| Sterility (no growth) | Pass | Pass | Pass |
| pH (7.40 ± 0.2) | 7.20 | 7.27 | 7.22 |
| Appearance - Visual (clear, light yellowish liquid with little or no precipitate) | Pass | Pass | Pass |
| Appearance - OD (passes test) | 1.34 | 1.38 | 1.85 |
| Osmolarity (<1000) | 877 | 854 | 832 |
| Solids (23 +/− 7 mg/ml) | 18 | 15 | 20 |
| Ethanol (not more than 10 ppm) | Pass | Pass | Pass |
| Ethyl Ether (not more than 5 ppm) | Pass | Pass | Pass |
| Conductivity (35 +/− 5 mMho) | 33 | 35 | 38 |

*Potency was measured with respect to monocyte/macrophage activation as described in Example 2; normal TNF-α release is at least 100 pg/ml.

Accordingly, the inventive composition can be prepared from readily available sources of bile, using standard laboratory methods, resulting in a standardized final product.

EXAMPLE 2

This example describes the biological activity of the composition of Example 1.

Studies were conducted to evaluate the effect of the composition of Example 1 on cytokine release from peripheral blood mononuclear cells (PBMN) and/or U937 cells which is a stable line of pre-monocyte cells (American Type Culture Collection (ATCC), Rockville, Md.). ELISA assays The samples were then stored for up to 2 weeks at −70° C. until immunoassays, such as ELISA, were conducted to quantify the cytokines present.

Cytokine synthesis in the supernatants was measured after stimulating human PBMN with the composition of Example 1 at volumes of 100 and 200 µl per well. The initial preparations of the composition showed no direct (i.e., no LPS) stimulatory effect on cytokine production (see Table II). If there was any effect, it appeared that cytokine production was below the constitutive level when PBMNs were incubated in medium alone.

TABLE II

Direct Effect of Composition of Example 1 on Cytokine Production after 24 hrs Amount of Cytokine Released (pp/ml)[1]

| Cytokine Assayed | Medium | Composition 100 μl | Composition 200 μl | LPS 1 μg |
|---|---|---|---|---|
| IL-1α | 61.6 ± 12 | 59.6 ± 7.8 | 54.3 ± 6.0 | 315 ± 117 |
| IL-1β | 199 ± 184 | 218 ± 165 | 188 ± 174 | 965 ± 99 |
| TNF[2] | 203 ± 149 | 151 ± 117 | 107 ± 120 | 1501 ± 284 |
| IL-6 | 928 ± 776 | 853 ± 673 | 829 ± 543 | 2016 ± 41 |
| IL-8 | 126 ± 70[3] | 94 ± 50[3] | 71 ± 41[3] | 361 ± 165[3] |
| GM-CSF | 13 ± 4 | 13 ± 7 | 15 ± 11 | 54 ± 20 |
| IFN-γ | 11 ± 18 | 9 ± 14 | 5 ± 6 | 54 ± 94 |
| IL-4 | <3.0 | <3.0 | <3.0 | <3.0 |

[1]Mean of eight patient samples in duplicate
[2]Mean of seven patient samples in duplicate
[3]ng/ml Cytokine synthesis in the supernatants was measured at 24 hrs at 37° C. after stimulating PBMNs with the composition of Example 1 and LPS (or LPS alone as positive control), using volumes of 100 μl of the composition of Example 1 per well. TNF was measured by a TNF-α ELISA kit (Endogen, Inc.), which detects a minimum level of 5 pg/ml of the cytokine. The other ELISA immunoassay kits that were used included: IL-1α (Endogen, Inc.); GM-CSF (Endogen, Inc.); RFN-α (Endogen, Inc.); IL-2 (Advanced Magnetics, Inc.); IL-6 (Advanced Magnetics, Inc.); IL-1 (Advanced Magnetics, Inc.); IL-4 (R&D Systems); and IL-8 (R&D Systems). The results indicated that TNF was the major cytokine present in the supernatants, along with smaller amounts of IL-1β and GM-CSF. For example, a 40 μl dose of the composition of Example 1 (batch B0222) stimulated the production and release of 178 pg/ml of TNF-α, 136 pg/ml GM-CSF, and 142 pg/ml of IL-1β.

Different batches of the composition of Example 1 were examined for their effect on LPS-induced release of TNF. In summary, it was found that batches of the composition produced in the same way and from the same animal induced an identical effect. However, changes in the method of preparation of the composition or use of a composition prepared from different animal species had different effects. For example, batches B29/3006, B0213, BC0241, BC0241-01, BC0242 (B=bovine) and C0203 (goat) induced a strong release of TNF above that induced by LPS alone, as shown in Table III, whereas batch 013/2109 (sheep) minimally stimulated TNF release at all doses tested. In contrast, batch R0201 (shark) inhibited TNF release at most doses tested. The TNF values shown in Table III were calculated as the difference in TNF-α release between the stimulation produced by LPS and the composition of Example 1 combined, less the stimulation produced by LPS alone.

TABLE III

Effect of Composition of Example 1 on LPS-Induced Release of TNF from PBMNs

| Batch | Composition Volume (μl) | TNF (pg/ml) |
|---|---|---|
| B0213 | 10 | 193 ± 161 |
|  | 100 | 858 ± 819 |
|  | 200 | 2131 ± 1742 |
| B29/3006 | 10 | 121 ± 102 |
|  | 50 | 422 ± 78 |
|  | 100 | 834 ± 811 |
|  | 200 | 2252 ± 676 |

TABLE III-continued

Effect of Composition of Example 1 on LPS-Induced Release of TNF from PBMNs

| Batch | Composition Volume (μl) | TNF (pg/ml) |
|---|---|---|
| C0203 | 10 | 101 ± 47 |
|  | 50 | 643 ± 231 |
|  | 100 | 2650 ± 1372 |
|  | 200 | 1851 ± 980 |
| B00241 | 10 | 199 |
|  | 25 | 201 |
|  | 50 | 162 |
|  | 100 | 339 |
|  | 200 | 552 |
| BC0241-01 | 10 | 170 |
|  | 25 | 180 |
|  | 50 | 219 |
|  | 100 | 223 |
|  | 200 | 589 |
| BC0242 | 10 | 294 |
|  | 25 | 401 |
|  | 50 | 409 |
|  | 100 | 603 |
|  | 200 | 574 |
| 013/2109 | 50 | −9 ± 73 |
|  | 200 | 179 ± 162 |
|  | 300 | 178 ± 373 |
| R0201 | 50 | 145 ± 256 |
|  | 200 | −370 ± 385 |
|  | 300 | −400 ± 185 |

Given that the composition of Example 1 affected LPS-induced release of TNF from human PBMNs, a series of experiments were conducted to examine the effect of the composition on LPS-induced release of TNF from PBMNs over time.

TABLE IV

Effect of Composition of Example 1 (Batch B0213) On LPS-Induced Release Of TNF (pg/ml) from PBMNs Over Time

| Time (hrs) | LPS only (50 ng/ml) | LPS + Composition (100 μl) |
|---|---|---|
| 2 | 697 ± 94 | 693 ± 339 |
| 6 | 2006 ± 736 | 1949 ± 442 |
| 24 | 800 ± 222 | 2301 ± 658 |
| 48 | 170 ± 149 | 1419 ± 447 |
| 72 | 132 ± 147 | 945 ± 367 |

Table IV shows that, by 2 hours, the level of TNF release from PBMNs induced by LPS had risen to 697 pg/ml and peaked at 6 hours at about 2006 pg/ml. At 24, 48 and 72 hours, the release of TNF progressively decreased. In fact, by 48 and 72 hrs, the TNF release from LPS-induced PBMNs was just above constitutive production levels. In contrast, LPS in combination with Batch B0213 of the composition, which is a strong stimulator of TNF release, induced peak TNF release at 24 hrs, at a time when the stimulatory effect of LPS had begun to fall. Unlike LPS alone, LPS in combination with batch B0213 of the composition continued to stimulate TNF release at 48 and 72 hrs at levels well above constitute production levels. These data show that Batch B0213 of the composition of Example 1 is effective in stimulating TNF production over time.

Batch R0201 of the composition, which was derived from sharks and is an inhibitor of TNF release, markedly inhibited TNF release at 2, 6 and 24 hrs. At 48 and 72 hrs, batch R0201 had minimal positive or negative effects.

Figure 5:
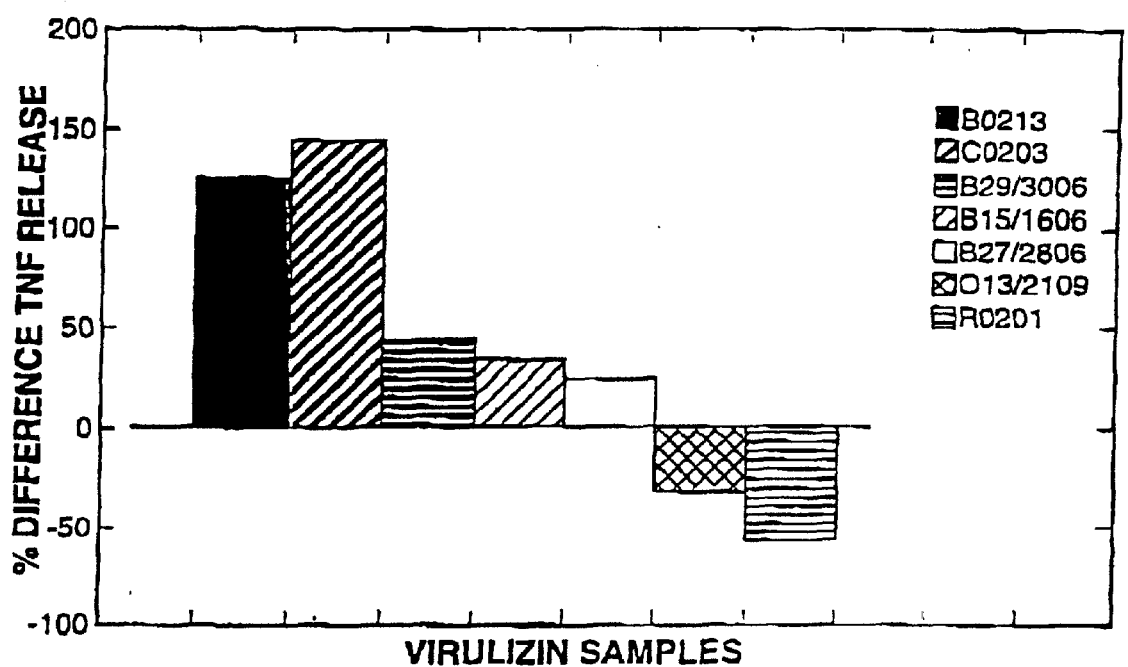
FIG. 5 is a bar graph showing the effect of the composition on LPS-induced release of TNF by PBMNs.

In summary, the above results indicate that some batches of the composition (e.g., from shark) inhibit TNF release from LPS-induced PBMNs, whereas other batches, such as those derived from bovine, goat, and sheep, stimulate LPS-induced TNF release. In conclusion, the composition of the invention can modulate TNF production, in both positive and negative manners. A summary of the data is shown in FIG. 5 and in Table V.

TABLE V

Summary Of Stimulatory And Inhibitory Effects Of Compositions Of Example 1

| Batch No. | Source | Normal or Concentrated | Buffer | TNF Release |
| --- | --- | --- | --- | --- |
| B0213 | Bovine | Normal | Yes | Stimulate |
| C0203 | Caprine | Normal | Yes | Stimulate |
| 013/2109 | Ovine | Concentrated | Yes | Stimulate |
| R0201 | Shark | Normal | Yes | Inhibit |
| B29/3006 | Bovine | Normal | Yes | Stimulate |
| B27/2806 | Bovine | Normal | Yes | Stimulate |
| B15/1606 | Bovine | Concentrated | Yes | Stimulate |

The PBMN-TNF assay as described above was standardized using 100 $\mu$l of the composition of Example 1 and 50 ng of LPS. PBMNs from 3 different human subjects were obtained as described above and used the same day. The results of each of the three assays (using individual subject cells) were averaged to compensate for variations in response between different subjects. The analysis involved determining the amount of TNF-$\alpha$ released in RPMI media alone and in the presence of 50 ng LPS. The TNF-$\alpha$ released in the presence of 100 $\mu$l of the composition of Example 1 in combination with 50 ng LPS was also determined. The TNF-$\alpha$ released in media was subtracted from the LPS value to obtain the TNF-$\alpha$ released in the presence of LPS alone. The media and LPS values were subtracted from the combined composition and LPS value to obtain the TNF-$\alpha$ released in the presence of the composition alone (reported in pg/ml). Accordingly, the TNF release assay served to quantify the potency of the bile extract.

The composition was also found to stimulate release of TNF-$\alpha$ from U937 cells, which were originally derived from a patient with histocytic lymphoma and display many characteristics of monocytes. U937 cells can be obtained from the ATCC. They are routinely maintained in RPMI-1640 medium (GIBCO, Grand Island, N.Y.) supplemented with 10% heat-inactivated fetal calf serum (FCS, GIBCO), 2 mM L-glutamine (ICN Biomedical Inc, Costa Mesa, Calif.), and 10 $\mu$g/ml Gentamycin Sulfate (SIGMA, Mississauga, Ontario, Canada) at 37° C., 5% $CO_2$. Passage of the U937 cells was performed every 3–4 days and seeding was at an initial concentration of $5 \times 10^5$ cells/ml. The U937 cells can be stimulated to differentiate to monocytes by exposure to phorbol 12-myristate 13-acetate (PMA; Sigma Chemical Co., St. Louis, Mo.). The resulting monocytes have the capacity to release TNF upon stimulation, such as with the composition of Example 1, alone or in combination with LPS.

PMA was first dissolved in dimethyl sulfoxide (DMSO, SIGMA) at a concentration of 10 mM and then diluted 1000-fold with PBS to a stock solution concentration of 10 $\mu$m and stored at $-20°$ C. U937 cell suspensions were centrifuged at 350×g for 10 mins at room temperature and reconstituted in fresh complete RPMI-1640 medium at a concentration of $2 \times 10^6$ cells/ml. Cell viability was determined by trypan blue exclusion and was routinely greater than 95%. PMA was further diluted 500-fold with complete culture media to a concentration of 20 nM.

Aliquots of 0.5 ml of U937 cells ($10^6$ cell/ml) were cultured in the presence or absence of 0.5 ml of PMA (20 nM) in 24-well, flat-bottom tissue culture plates (Becton Dickinson, Lincoln Park, N.J.) and incubated for 72 hrs at 37° C., 5% $CO_2$. The final concentrations per well were $5 \times 10^5$ cells and 10 nM PMA.

After 72 hrs of incubation, 120 $\mu$l of media were removed and replaced by 100 $\mu$l of the composition of Example 1 and 10 $\mu$l of sterile deionized distilled water, in the presence or absence of 10 $\mu$l of LPS (5 ng/$\mu$l). After 24 hrs of incubation, any cells and particulate matter were pelleted by centrifugation at 350×g for 10 min and the resulting supernatants were stored at $-20°$ C. until they were assayed for TNF-$\alpha$. All the Virulizin samples were tested on two separate occasions.

Two-site sandwich ELISAs were performed to quantify TNF-$\alpha$ in the U937 cell culture supernatants using TNF-$\alpha$ ELISA kits purchased from Endogen, Inc. (Cedarlane Laboratories, Hornby, Ontario). The protocol recommended by the manufacturer was used. Briefly, 100 $\mu$l of TNF-$\alpha$ standards and test samples were added to antihuman TNF-$\alpha$ pre-coated 96-well plates and incubated at 37° C., 5% $CO_2$ for 3 hrs. After extensive washing with washing buffer, 100 $\mu$l of antihuman TNF-$\alpha$ conjugated to alkaline phosphatase were added to plates and incubated at 37° C., 5% $CO_2$ for 2 hrs. After incubation, the plates were washed as described above and 100 $\mu$l of premixed TMB substrate was added to each well and the enzymatic color reaction was allowed to develop at room temperature in the dark for 30 min. Then 100 $\mu$l of stop solution was added to each well to stop the reaction and the plates were read using an SLT Lab Instrument ELISA reader at 450 nm. The detection limit of the assay was 5 pg/ml.

TNF values for U937 cells were determined as described for PBMN cells. Results of the composition tested with 50 ng LPS are presented in Table III.

TABLE VI

Effect of Composition on TNF Release from U937 Cells

| Composition Batch Number (100 $\mu$l) | TNF (pg/ml) |
| --- | --- |
| BC0241 | 4900 |
| BC0241-01 | 4028 |
| B00242 | 6746 |
| B00247 | 5534 |
| BC0248 | 6053 |
| BC0249 | 5540 |
| BC0250 | 5794 |

EXAMPLE 3

This example describes the physical, chemical and biochemical characteristics of the composition of Example 1.

Physicochemical characteristics, such as conductivity, osmolarity, and total solids, for three manufactured batches of a composition prepared in accordance with Example 1 were determined. The results, tabulated in Table I, demonstrate the sterility, potency, and reproducibility of the manufactured product, and thereby provide a product specification. The ethanol and ethyl ether tests are in process tests only. Potency, i.e., the TNF release was determined as described in Example 2. The methods used to determine the characteristics are tabulated below.

TABLE VII

Characteristics Of Compositions Of Example 1 As Products Of Manufacture

| Test | Specification | Method |
|---|---|---|
| Potency | >100 pg/ml TNF-α | Monocyte/macrophage activation: TNF-α release |
| Identity/Parity | Agrees with reference | HPLC |
| Safety | Passes test | General safety test (mice and guinea pigs) (21 C.F.R. § 610.11) |
| Pyrogenicity | Temperature increase shall not exceed 0.4° C. | Pyrogen test (rabbits) USP |
| Endotoxin | <2 EU/ml | Limulus Amoebocyte Lysate Test USP |
| Sterility | No growth | Sterility Test USP |
| pH | 7.40 ± 0.2 | pH test USP |
| Appearance | Clear, light yellowish liquid with little or no precipitate | Visual Inspection |
| Solids | 23 ± 7 mg/ml | Lyophilization |
| Osmolarity | <1000 mOsm | Freezing point depression USP |
| Ethyl Alochol | Not more than 10 ppm | Direct Injection Gas Chromatography |
| Ethyl Ether | Not more than 5 ppm | Direct Injection Gas Chromatography |
| Conductivity | 35 ± 5 mMHO | Copenhagen Radiometer Model |

The above-described physical and chemical properties, such as conductivity, osmolarity and total solids, were consistent with a composition that is over 99% salt. Less than 1% of the solids in the composition was organic material, around half of the solids were carbohydrates, and the rest were amino acids, lipids, and phospholipids. Proteins and peptides were present. SDS gel electrophoresis confirmed that there were more peptides than proteins in the composition. High molecular weight molecules were not detected.

HPLC and bioassay test methods for the composition of the invention were used to characterize the product as the buffered liquid and the concentrated formula. The HPLC results described below indicate that the product was the same in all of its presentations.

A tandem column reverse-phase HPLC method was used to characterize the composition of Example 1. For this method, samples were lyophilized and then reconstituted in Buffer A (0.1% trifluoroacetic acid (TFA)) and were run on a WP60009-C18 column (W-Pore C18, 250×4.6 mm; Phenomenex of California) in tandem with a prime-sphere HC-C18 column (250×4.6 mm; Phenomenex). The columns were run at ambient temperature using Buffer A and Buffer B (0.1% TFA in 100% acetonitrile), with a flow rate of 0.9 ml/min. A 150 μl sample was applied to the first column and Buffer A was run through the system for 20 mins. Next, a first linear gradient, 0–80% Buffer B, was run over 35 mins, followed by a second linear gradient, 80–0% Buffer B, over 5 mins. Eluted compounds were detected via optical absorbance at from 190 to 284 nm, with most runs being detected at 210 and 235.

The composition of Example 1 had a consistently reproducible pattern on reverse-phase HPLC in which peaks were seen. The reverse-phase HPLC readings for three lots of the composition of the invention are shown in FIGS. 1–3.

Six batches of bile extract, which were prepared as in Example 1 and labeled A–F, were analyzed for their amino acid profiles on an LKB 4151 Alphaplus amino acid analyzer operated in a physiological mode, with post-column detection with ninhydrin. The results, in nmoles/100 μl, are shown in Table VIII.

TABLE VIII

Amino Acids And Urea Profiles Of Compositions Of Example 1

| Amino Acids and Urea | A | B | C | D | E | F |
|---|---|---|---|---|---|---|
| P-Ser | 0.342 | 0.429 | 0.473 | 3.239 | 1.454 | 1.048 |
| Tau | 3.438 | 8.325 | 2.515 | 11.297 | 23.005 | 47.019 |
| Urea | 23.318 | 35.224 | 146.806 | 608.984 | 98.489 | 115.26 |
| Asp | 0.606 | 1.060 | 1.163 | — | — | — |
| Thr | 0.649 | 0.483 | — | 0.345 | 12.646 | 1.548 |
| Ser | 1.104 | 0.833 | 0.452 | 0.821 | — | — |
| Glu | 2.112 | 8.257 | 8.029 | 13.333 | 36.169 | 43.632 |
| Gly | 5.465 | 15.667 | 6.341 | 12.625 | 38.842 | 82.418 |
| Ala | 2.634 | 4.449 | 3.572 | 6.093 | 32.662 | 23.202 |
| Val | 0.942 | 0.645 | 0.550 | 1.311 | 15.521 | 4.362 |
| Ile | — | — | — | — | 3.089 | — |
| Leu | — | — | 0.186 | 1.079 | 7.300 | 1.197 |
| B-Ala | 0.387 | 0.503 | 0.450 | 1.060 | 1.461 | 2.640 |
| Orn | — | — | — | 0.102 | 0.412 | 0.336 |

Samples A–F were also assessed for presence of bovine DNA. The samples were examined utilizing a $^{32}$p-labeled bovine DNA probe generated from bovine genomic DNA. The assay included the samples, spiked samples, negative and positive controls, and standards. The study was conducted in compliance with GLP regulations. This assay detected 3.9 pg of reference standard DNA. Each of the samples was calculated to contain less than 4 pg/ml DNA.

Samples A–F were also tested for the presence of various electrolytes. This analysis was provided by the Biotechnology Service Centre, Department of Clinical Biochemistry, University of Toronto. The results, in mmole/l, are shown in Table IX.

TABLE IX

Electrolyte Content of Compositions of Example 1

| Electrolyte | A | B | C | D | E | F |
|---|---|---|---|---|---|---|
| NA | 55 | 68 | 127 | 359 | 250 | 309 |
| K | 0.9 | 0.9 | 2.5 | 10.2 | 3.6 | 4.2 |
| Ca | 0.06 | 0.10 | 0.006 | 0.2 | 0.13 | 0.27 |
| Mg | 0.25 | 0.15 | 0.09 | 0.35 | 0.14 | 0.17 |
| Cl | 50 | 59 | 118 | 386 | 207 | 263 |
| $PO_4$ | 0.06 | 0.03 | 0.05 | 0.27 | 0.18 | 0.24 |
| $SO_4$ | 2.17 | 1.89 | 2.05 | 1.15 | 7.13 | 11.36 |

Samples A–F were submitted to semi-quantitative multi-element analysis by inductively coupled mass spectrometry (ICP-MS) under standard conditions. The results, in parts per million (ppm), are described in Table X.

TABLE X

Elemental Analysis of Compositions of Example 1

| | A | B | C | D | E | F |
|---|---|---|---|---|---|---|
| Scandium | 0.620 | 0.820 | 1.030 | 1.030 | 2.020 | 1.900 |
| Titanium | 0.210 | 0.310 | 0.260 | 0.720 | 0.920 | 1.180 |
| Vanadium | 0.030 | 0.040 | 0.080 | 0.180 | 0.140 | 0.160 |
| Chromium | 0.030 | 0.040 | 0.060 | 0.080 | 0.170 | 0.190 |
| Iron | 0.300 | 0.380 | 0.510 | 4.310 | 0.690 | 0.760 |
| Manganese | 0.020 | 0.020 | 0.030 | 0.530 | 0.050 | 0.060 |
| Nickel | <det | <det | 0.030 | 0.250 | 0.130 | 0.160 |
| Cobalt | <det | <det | 0.001 | 0.013 | 0.003 | 0.005 |
| Copper | 0.700 | 0.940 | 0.840 | 1.520 | 2.140 | 2.470 |
| Zinc | 15.600 | 18.300 | 8.800 | 0.830 | 29.800 | 32.900 |
| Gallium | 0.008 | 0.008 | 0.004 | 0.003 | 0.013 | 0.015 |
| Selenium | 1.020 | 1.590 | 2.060 | 7.710 | 3.810 | 7.860 |

TABLE X-continued

Elemental Analysis of Compositions of Example 1

|  | A | B | C | D | E | F |
|---|---|---|---|---|---|---|
| Arsenic | 0.030 | 0.070 | 0.100 | 0.200 | 0.250 | 0.350 |
| Strontium | 0.010 | 0.010 | 0.020 | 0.060 | 0.040 | 0.050 |
| Rubidium | 0.090 | 0.110 | 0.190 | 0.320 | 0.410 | 0.490 |
| Ruthenium | <det | 0.001 | <det | 0.001 | <det | 0.001 |
| Palladium | 0.002 | <det | 0.003 | 0.005 | 0.003 | 0.003 |
| Cadmium | <det | <det | <det | 0.002 | 0.005 | 0.003 |
| Silver | <det | <det | 0.002 | 0.002 | 0.001 | <det |
| Tellurium | 0.003 | 0.003 | 0.050 | 0.090 | 0.080 | 0.070 |
| Antimony | <det | 0.002 | 0.003 | 0.002 | 0.007 | 0.006 |
| Barium | 0.017 | 0.019 | 0.035 | 0.040 | 0.057 | 0.080 |
| Cesium | 0.001 | 0.002 | 0.004 | 0.008 | 0.005 | 0.006 |

Note: The term <det means below level of detection.

Anion and cation analysis was also conducted on samples A–F. For this analysis, the samples were prepared as recommended in *APHA Standard Methods For The Examination Of Water And Wastewater*, 16th Edition, 1985 or *MOE Handbook Of Analytical Methods For Environmental Samples*, 1983. Instrumentation for the anion/cation analysis was: (1) for metals, Jarrell Ash 61E ICAP emission, Perkin Elmer 3030 Zeeman Graphite Furnace, and Perkin Elmer 2380 Cold Vapour AA; (2) for anions, Dionex 2000i Ion Chromatograph; and for conventionals, Skalar SA5 Segmented Flow Analyzer. The results, in mg/l, are presented in Table XI.

As several sulfate esters participate in the regulation of many cellular events, such as cell proliferation and differentiation, Sample D was analyzed for sulfate ions before and after acid hydrolysis. Using whole sample D (i.e., unfractionated), the nonhydrolyzed sample yielded 1000 μm sulfate, whereas the hydrolyzed sample yielded 1200 μM sulfate. Since the sulfate ion concentration increased after acid hydrolysis, these results suggest that 20% of the total sulfate ions present are sulfate esters.

Physicochemical standards have been identified for the composition of Example 1 and are essentially consistent with earlier studies, which are described in Example 4. These standards indicate that a consistent product can be repeatedly obtained.

EXAMPLE 4

This example describes the physical, chemical, and biological properties of a number of earlier batches of the composition of Example 1.

Batches of bile extract were prepared in accordance with the method described in Example 1. In addition, the chemical composition of the batches was determined and an amino acid analysis of the batches was conducted, using the methods disclosed in Example 3. The results are shown in the following tables.

TABLE XI

Anion And Cation Analysis Of Compositions Of Example 1

|  | A | B | C | D | E | F |
|---|---|---|---|---|---|---|
| Silver | <0.007 | <0.007 | <0.007 | <0.007 | <0.007 | <.007 |
| Beryllium | <0.003 | <0.003 | <0.003 | <0.003 | <0.003 | <.003 |
| Cadmium | <0.003 | <0.003 | <0.003 | 0.004 | <0.003 | <.003 |
| Bismuth | <0.04 | <0.04 | <0.04 | <0.04 | <0.04 | <0.04 |
| Cobalt | <0.005 | 0.005 | <0.005 | 0.006 | <0.005 | <.005 |
| Copper | 0.013 | 0.036 | 0.043 | 0.138 | 0.112 | 0.210 |
| Manganese | 0.007 | 0.006 | 0.007 | 0.283 | 0.018 | 0.029 |
| Molybdenum | 0.014 | 0.012 | 0.012 | 0.015 | <0.006 | <.006 |
| Nickel | <0.01 | 0.012 | <0.01 | 0.058 | 0.020 | 0.020 |
| Lead | <0.025 | <0.025 | <0.025 | <0.025 | <0.025 | <.025 |
| Strontium | 0.01 | 0.019 | 0.015 | 0.126 | 0.040 | 0.063 |
| Vanadium | 0.009 | 0.008 | 0.004 | 0.011 | <0.003 | <.003 |
| Zinc | 6.04 | 5.93 | 1.95 | 0.383 | 14.5 | 15.2 |
| Tungsten | 0.587 | 0.436 | 0.315 | 0.435 | 0.498 | 0.481 |
| Phosphorus | 10.6 | 11.4 | 3.34 | 676 | 22.8 | 14.1 |
| Titanium | <0.003 | <0.003 | 0.006 | 0.005 | <0.003 | 0.004 |
| Barium | 0.062 | 0.056 | 0.055 | 0.105 | 0.079 | 0.117 |
| Chromium | 0.025 | 0.036 | 0.028 | 0.107 | 0.102 | 0.124 |
| Sodium | 1250 | 1570 | 2770 | 13900 | 5350 | 6570 |
| Potassium | 30.2 | 32.8 | 65.4 | 686 | 125 | 154 |
| Iron | 0.018 | 0.023 | 0.024 | 0.008 | 0.036 | 0.037 |
| Aluminum | 0.240 | 0.238 | 0.052 | <0.025 | 0.790 | 0.361 |
| Calcium | 1.22 | 5.34 | 2.00 | 10.2 | 5.04 | 10.4 |
| Magnesium | 0.757 | 0.756 | 0.891 | 15.8 | 2.27 | 3.70 |
| Fluoride | <100 | <100 | <100 | <100 | <100 | <100 |
| Chloride | 2120 | 1860 | 3110 | 30400 | 10900 | 9110 |
| Sulphate | 144 | 154 | 152 | 332 | 1150 | 1590 |
| Phosphate-P | 1.8 | 1.3 | 1.5 | <det | <det | <det |
| Nitrate as N | <10 | <10 | <10 | <10 | <10 | <10 |
| Nitrite as N | <100 | <100 | <100 | <100 | <100 | <100 |
| Bromide | <35 | <35 | <35 | <35 | <35 | <35 |
| Ammonia as N | 98.0 | 125 | 130 | 492 | 425 | 592 |

TABLE XI

Chemical Composition Earlier Batches of Compositions of Example 1

| Composition Batch No. | Solids (mg/ml) | Amino Acids (µg/ml) | Sugars (µg/ml) | Lipids (µg/ml) | High M.W. >3kD Polypeptide (µg/ml) |
|---|---|---|---|---|---|
| B0201 | 15.3 | 4.59 | 40.85 | ND | NA |
| B0202 | 15.7 | 13.16 | 54.95 | ND | NA |
| B0203 | 15.0 | 72.67 | 25.5 | ND | NA |
| B0208 | 7.8 | 4.53 | 30 | ND | ND |
| B0209 | 8.5 | 2.27 | 24 | ND | ND |
| B0211 | 5.6 | 1.47 | 19.2 | ND | ND |
| B0106 | 32.2 | 1.16 | 32.6 | ND | ND |
| B0706 | 32.7 | 1.42 | 26.2 | ND | ND |
| B1306 | 22.3 | 8.01 | 48 | ND | ND |
| B2006 | 21.7 | 9.73 | 38.4 | ND | ND |
| B2306 | 28.5 | 16.35 | 42 | ND | ND |
| B0213 | 31.6 | 21 | 61 | ND | ND |
| R0201/−pH | 52.5 | 1553 | 216 | ND | ND |
| R0201/+pH | 55.8 | 1530 | 280 | ND | ND |
| C0203 | 36.1 | 113 | 42 | ND | ND |
| 0-13/2109 | 12.1 | 149 | 36 | ND | ND |
| B27/2806 | 17.5 | 28 | 37 | ND | ND |
| B29/3006 | 28.7 | 26 | 60 | ND | ND |
| B15/1606 | 26.8 | 41 | 45 | 75 | ND |

Note: ND means not detectable, thus less than 0.5 µg/ml lipids per and/or less than 1.0 µg/ml high molecular weight polypeptide. NA means not assayed.

TABLE XII

Physical, Chemical and Biological Properties of Earlier Batches of Compositions of Example 1

| Batch No. | pH | Conductance (mMho) | Osmolarity (mOsM) | Absorbance (O.D. 280 nm) | UV, VIS Peaks | Activity (Units/ml) | Potency pg/ml |
|---|---|---|---|---|---|---|---|
| B0201 | 7.37 | 16.9 | 361 | 0.98 | 404 nm | 10.5 | |
| B0202 | 7.35 | 17.3 | 298 | 0.777 | None | 6.5 | |
| B0203 | 7.3 | 17.7 | 360 | 0.67 | 365 nm | 21.0 | |
| B0208 | 7.00 | 16.1 | 250 | 0.453 | None | 8.1 | |
| B0209 | 7.31 | 11.2 | 259 | 0.594 | None | 6.7 | |
| B0211 | 7.35 | 34.9 | 175 | 0.287 | None | 7.5 | |
| B0106 | 7.57 | 34.3 | 627 | 0.341 | None | 17.2 | |
| B0706 | 7.57 | 11.6 | 627 | 0.387 | None | 23.0 | |
| B1306 | 8.02 | 35.6 | 790 | 1.147 | None | 17.0 | |
| B2006 | 8.56 | 33.9 | 651 | 1.024 | None | 21.0 | |
| B2306 | 8.01 | 35.1 | 623 | 1.054 | None | 19.0 | |
| B0213 | 7.75 | 29.5 | 628 | 0.48 | none | | 858 |
| R0201-pH | 7.95 | 44.5 | 877 | 1.59 | 271 nm 0.65 O.D. | | NA |
| R0201/-+pH | 7.60 O.D. | 50.0 | 1162 | 2.29 | 266 nm 1.6 | | NA |
| C0203 | 7.90 | 34.8 | 657 | 0.96 | none | | NA |
| 0-13/2-109 | 7.73 | 17.0 | 316 | 0.83 | none | | NA |
| B27/2806 | 7.71 | 22.0 | 453 | 0.49 | none | | NA |
| B29/3006 | 7.67 | 28.8 | 605 | 0.55 | none | | NA |
| B15/1606 | 7.84 | 35.0 | 753 | 1.04 | none | | NA |

Comments:
1. Full isotonic PBS solids were added to batches No. B0106 and B0706.
2. Batches B1306, B2006 and B2306 were concentrated two times without adjusting pH.

TABLE XIII

Amino Acid Composition of Earlier Batches of Composition of Example 1

| | BATCH NUMBER | | | | | | | |
|---|---|---|---|---|---|---|---|---|
| | B-0208 | B-0209 | B-0211 | 01/06 | 07/06 | 1306 | 2006 | 2306 |
| Asparagine | 365 | | | | 113 | | | 289 |
| Serine | | 69 | 12 | 7 | 17 | 144 | 119 | 308 |
| Glycine | 22 | 449 | 274 | 279 | 417 | 3731 | 5314 | 10371 |
| Histidine | | 192 | | 90 | 68 | 938 | 1335 | 2114 |
| Arginine | | | | 161 | | | 533 | |
| Threonine | | 19 | 13 | | 30 | 148 | 142 | 250 |
| Alanine | | 173 | 112 | 24 | 64 | 949 | 1002 | 1423 |
| Proline | 1092 | | | | 74 | 817 | 639 | 1075 |
| Tyrosine | 15 | 55 | 57 | 43 | 39 | 205 | 135 | 45 |
| Valine | 121 | 63 | 31 | 10 | 15 | 367 | 335 | 224 |
| Methionine | | 970 | 461 | 462 | 13 | 107 | 121 | 70 |
| Cysteine | | 103 | 90 | 41 | 12 | 86 | 49 | 10 |
| Isoleucine | 2721 | 84 | 95 | 17 | | 232 | 216 | 68 |
| Leucine | | 58 | | | 9 | 221 | 242 | 84 |
| Phenylalanine | | 57 | 200 | 16 | | 45 | 80 | 23 |
| Lysine | 191 | 36 | 123 | 6 | 18 | | 15 | |
| Total AA μg/ml | 4.53 | 2.27 | 1.47 | 1.16 | 1.42 | 8.01 | 9.73 | 16.35 |

EXAMPLE 5

This example describes the biological activity of fractions of the composition of Example 1.

The biological activity of fractions of the composition of Example 1 was investigated. The analytical results are consistent with the biological activity of the composition being attributed to small molecular weight components (i.e., less than 3000 daltons). This was determined through an experiment in which the composition was passed through the reverse-phase HPLC described in Example 3 and eluted fractions who isolated and analyzed for potency by the PBMN-TNF assay described in Example 2. Significant activity was only detected in the early-eluting peak (F1), i.e., 5.6 to 6.2 mins. which is consistent with a molecular weight of less than 3000 daltons (see Table XIV).

TABLE XIV

Effect of Fractions of Composition of Example 1 Eluted by Reverse-Phase HPLC on TNF Release Prom LPS-Induced PBMNs

| Sample Tested | HPLC (min) | Quantity per Well | TNF-α Released (pg/ml) Total | -LPS | Osmolarity (mOsm) |
|---|---|---|---|---|---|
| LPS | — | 50 ng | 305 ± 79 | 0 | 304 |
| Composition of Example 1: | | | | | |
| Whole | 0 | 100 μl | 519 ± 195 | 213 | 415 |
| F1 | 5.60–6.20 | 100 μl | 508 ± 82 | 203 | 344 |
| F2 | 6.20–6.55 | 100 μl | 149 ± 44 | −157 | 281 |
| F3 | 6.55–7.10 | 100 μl | 306 ± 80 | 1 | 309 |
| F4 | 7.10–7.90 | 100 μl | 316 ± 123 | 11 | 309 |
| F5 | 7.90–8.40 | 100 μl | 390 ± 95 | 84 | 309 |
| F6 | 8.40–8.90 | 100 μl | 282 ± 103 | −24 | 311 |
| F7 | 8.90–9.40 | 100 μl | 296 ± 108 | −10 | 309 |
| F8 | 9.40–10.00 | 100 μl | 341 ± 112 | 36 | 309 |
| F9 | 10.00–10.40 | 100 μl | 33 ± 139 | 24 | 308 |
| F10 | 10.40–12.00 | 100 μl | 316 ± 101 | 11 | 311 |
| F11 | 12.00–13.60 | 100 μl | 354 ± 74 | 49 | 311 |
| F12 | 13.60–14.20 | 100 μl | 344 ± 107 | 39 | 315 |
| F13 | 14.20–15.35 | 100 μl | 296 ± 117 | −9 | 311 |
| F14 | 15.35–15.75 | 100 μl | 344 ± 108 | 39 | 314 |
| F15 | 16.75–18.20 | 100 μl | 300 ± 104 | −5 | 313 |

Note:
1. Number of patients tested: 3.
2. Total TNF-a Released is corrected for release by RPMI Media (13 ± 4 pg/ml, 306 mOsm).
3. HPLC fractions 1–2 reconstituted in water; 3–15 reconstituted in PBS buffer.
4. Columns in tandem are: W-Porex C18 and PrimeSphere. Both from Phenomenex, 250 × 4.6 mm.
5. Volume of LPS per well: 10 μl.
6. Total volume per well: 1000 μl.
7. Sample volumes are equivalent.

Additional experiments were done as follows to show that the active (TNF-releasing) components had molecular weights less than 3500 and less than 1000 daltons. Batch BC0241 was fractionated by carrying out a Folch extraction according to Tamari et al., *Agr. Biol. Chem.,* 40 (10), 2057–2062 (1977). The water layer was dried on a rotovap to yield a light brown, granular solid. A stock solution of this solid was prepared at a concentration of 5 mg/ml. A portion of the stock solution was loaded into Centri/por Centrifuge Concentrators (Spectrum Products, Houston, Tex.) having a 3500 or 1000 dalton molecular weight cutoff membrane. The Concentrators were centrifuged at approximately 1500×g until a portion of the material had passed through the membrane. The solution that passed through the membrane was assessed for potency in the PBMN-TNF assay. The results are presented in Table XV.

TABLE XV

Molecular Weights of Active Components of Composition of Example 1.

| SAMPLE | TNF Released (pg/ml) |
| --- | --- |
| Folch water layer from BC0241 | 1709 |
| Folch water layer passed through 3500 dalton membrane | 2318 |
| Folch water layer passed through 1000 dalton membrane | 2423 |

The analysis of the biological activity of molecular weight fractions indicates, accordingly, that the TNF-releasing components are less than 1000 daltons molecular weight.

EXAMPLE 6

This example illustrates the effect of the composition of Example 1 on T and B lymphocytes in culture.

The growth of human lymphocytes was examined under carefully controlled conditions in the presence and absence of the composition of Example 1. Standard concentrations of lymphocytes were incubated in wells containing various concentrations of the composition. When normal T and B human lymphocytes were incubated with the composition in concentrations similar to those that are used clinically, there were no adverse effects as judged by trypan blue dye exclusion. Accordingly, the composition of the invention was non-toxic to normal T and B lymphocytes in culture.

The effect of the composition on the survival of human PBMN also was examined. PBMNs were incubated for 24 and 48 hrs in plastic microwell plates with various volumes of the composition and tissue culture medium. At the end of this period, the number of surviving cells was estimated by trypan blue dye exclusion.

TABLE XVI

Concentration of Viable PBMNs After Incubation with Composition of Example 1

| | | No. of Live PBMN per Well by Trypan Blue (×10$^6$)[1] | |
| --- | --- | --- | --- |
| Concentration (µl/well) | Zero time | After 24 hrs No. (% viable) | After 48 hrs No. (% viable) |
| Patient S.Z. | | | |
| 0 | 0.70[2] | 0.23 (33) | 0.10 (14) |
| 25 | | 0.43 (61) | 0.15 (21) |
| 50 | | 0.10 (14) | 0.23 (33) |
| 100 | | 0.15 (21) | 0.18 (26) |
| 200 | | 0.48 (69) | 0.23 (33) |
| LPS (µg/well) | | | |
| 1 | | 0.30 (43) | 0.28 (40) |
| 10 | | 0.25 (36) | 0.13 (18) |
| Patient E.S. | | | |
| 0 | 1.30[2] | 0.70 (54) | 0.33 (25) |
| 25 | | 0.65 (50) | 0.15 (12) |
| 50 | | 0.68 (52) | 0.38 (29) |
| 100 | | 0.75 (58) | 0.23 (18) |
| 200 | | 0.65 (50) | 0.20 (15) |
| LPS (µg/well) | | | |
| 1 | | 0.60 (46) | 0.53 (41) |
| 10 | | 0.15 (12) | 0.15 (12) |

[1]Approximately 1 × 10$^6$ cells plated/well in triplicate.
[2]Actual number of cells counted/well (×10$^6$).

The above data show that the number of surviving cells fell at 24 and again at 48 hours; however, the number of surviving cells in the presence or absence of the composition was not different. Moreover, increasing volumes of the composition had no effect on survival. Thus, the composition showed no cytotoxicity to human PBMN.

The ability of the composition to stimulate lymphocytes was evaluated in the following 3 indicator systems: 1) stimulation of lymphocyte DNA synthesis; 2) induction of lymphocyte-mediated cytotoxic function; and 3) induction of monocyte/macrophage-mediated cytotoxic function. These tests were chosen for the screen because they measure immunological functions that have been shown to be associated with different clinical parameters in patients with malignant disease. These indicators of immune function also can be modulated in cancer patients treated with different biological response modifying agents, such as IFN or IL-2. The results of the initial screening procedures are presented below.

1. Stimulation of lymphocyte DNA synthesis: comparison with an optimal stimulating concentration of phytohemagglutinin (PHA):

| Stimulant | Counts Per Minute |
| --- | --- |
| Medium | 374 |
| PHA | 125,817 |
| Composition (#222) | 1,116 |
| Composition (1:10) | 1,021 |
| Composition (1:50) | 649 |

Unlike the prototypic mitogen, PHA, it was noted that the composition of Example 1 did not stimulate lymphocytes to undergo blastogenesis and cell division, which is consistent with these results showing little or no stimulation of DNA synthesis by the composition.

2. Stimulation of lymphocyte-mediated cytotoxic function and comparison with an optimal stimulating concentration of IL-2:

| Stimulant | Lytic Units |
| --- | --- |
| Medium | 30.8 |
| IL-2 | 472.5 |
| Composition (neat) | 48.1 |
| Composition (1:10) | 33.3 |
| Composition (1:50) | 44.8 |

Unlike the prototypic stimulator of lymphocyte cytotoxic function, IL-2, the composition did not elicit lymphocyte cytotoxicity. The number of lytic units stimulated by the composition was virtually identical to that of the negative control (i.e., medium).

3. Stimulation of monocyte-mediated cytotoxic function by the composition: comparison with IFN-γ and LPS (IFN+LPS)

| Stimulant (E/T = 20/1) | % Cytotoxicity |
| --- | --- |
| Medium | 4.3 |
| IFN + LPS | 24.4 |
| Composition (neat) | 19.7 |
| Composition (1:10) | 20.0 |
| Composition (1:50) | 11.5 |

The composition of Example 1 was capable of stimulating peripheral blood monocytes to express tumoricidal function in a dose-dependent manner. The magnitude of stimulation is comparable to that elicited by the prototypic imacrophage activator combination of IFN-γ and LPS. It is important to recognize that the action of the composition in these in vitro assays did not require the addition of endotoxin, as in the case with any other macrophage activator.

EXAMPLE 7

This example illustrates the results of assays conducted to survey what, if any, cytokines are present in the composition of Example 1.

Samples of a bile extract (50 μl and 100 μl aliquots per test) prepared according to Example 1 were tested for the presence of the following cytokines (sources and detection limits of the ELISA immunoassay kits used are noted parenthetically): TNF-α (Endogen, Inc. (5 pg/ml)); IL-1α (Endogen, Inc. (50 pg/ml)); IL-1β (4.3 pg/ml); GM-CSF (Endogen, Inc.); RFN-α (Endogen, Inc.); IL-2 (Advanced Magnetics, Inc.); IL-6 (Advanced Magnetics, Inc. (7 pg/ml)); IFN-γ (5 pg/ml) [source]; IL-1 (Advanced Magnetics, Inc.) [need limit]; IL-4 (R&D Systems (3 pg/ml)); and IL-8 (R&D Systems (4.7 ng/ml)). Procedures used were according to the individual kit's instructions, which can be easily followed by an ordinary artisan.

It was determined that the composition of the invention contained no measurable levels of any cytokine tested, those being TNF-α, IL-1 α, IL-1 β, IL-4, IL-6, IL-8, GM-CSF and IFN-γ, as described in Table XVII.

TABLE XVII

Elisa Determination of Cytokines In Composition

| Cytokine (pg/ml) | 50 μl | 100 μl |
| --- | --- | --- |
| TNF | <5 | <5 |
| IL-1β | — | 6.5 |
| GM-CSF | <5 | — |
| IL-6 | <7 | — |
| IFNγ | <5 | — |
| IL-1α | <50 | — |
| IL-4 | — | <13 |
| IL-8 (ng/ml) | | <4.7 |

EXAMPLE 8

This example describes pharmacodynamic studies in mice with the composition of Example 1, including the direct in vitro effect of Virulizin™ as well as the effect of Virulizin™ administered in vivo on murine peritoneal macrophages.

Peritoneal macrophages were harvested from C57BL/6 mice 72 hours after intraperitoneal injection of 1.5 ml of 4% protease peptone. The macrophages were then stimulated in vitro with medium alone, 50 ng LPS, or VIRULIZIN™. Measurements of the stimulation was done with respect to TNF (by ELISA) and NO (by spectrophotometric assay using the Greiss reagent) levels in duplicate experiments. Standard error of the mean between duplicate experiments was less than 10%. As noted in Table XVIII, VIRULIZIN™ induced a slight increase in TNF-α production (60–232 pg/ml) compared to background (medium) levels (120 pg/ml), but VIRULIZIN™ in comparison to LPS (2225 pg/ml) was not a strong stimulant of macrophage TNF-α release. Nitric oxide production was zero.

TABLE XVIII

In Vitro Stimulation of Protease Peptone Macrophages

| Macrophages Stimulated With | TNF (pg) Mean | NO (μM) Mean |
|---|---|---|
| Medium | 120 | 0 |
| LPS (1 μg/ml) | 2225 | 11 |
| Virulizin | | |
| 1:2 | 62 | 0 |
| 1:5 | 181 | 0 |
| 1:10 | 206 | 0 |
| 1:20 | 202 | 0 |
| 1:40 | 232 | 0 |
| 1:80 | 142 | 0 |
| 1:200 | 122 | 0 |

In vitro synergy of Virulizin™ with LPS for TNF-α release was also addressed. Peritoneal macrophages were harvested from C57BL/6 mice after the same aforementioned treatment. The macrophages were then stimulated with 50 ng LPS alone or LPS with different dilutions of VIRULIZIN™. As above, TNF was determined via ELISA. As noted in Table XIX, LPS alone induces about 2900 pg/ml of TNF-α release from mouse peritoneal macrophages in vitro compared to 262 pg/ml for medium. When LPS is combined with VIRULIZIN™, there is about an 800 pg/ml increase in TNF-alpha release at dilutions of VIRULIZIN™ 1:5 and 1:10 and enhanced release to at least 1:40.

TABLE XIX

Synergistic Combinations between Virulizin ™ and IFN-α or LPS

| Macrophages Stimulated With | TNF (pg/ml) | NO (μM) |
|---|---|---|
| Medium | 262 | 1.6 ± 1.1 |
| LPS (5 ng/ml) | 2900 | 8.6 ± 1.3 |
| LPS (5 ng/ml + Composition of Example 1: | | |
| 1:5 | 3750 | 13.2 ± 0.5 |
| 1:10 | 3750 | 16.9 ± 2.7 |
| 1:20 | 3500 | 13.5 ± 2.5 |
| 1:40 | 3600 | 27.1 ± 11.6 |
| 1:80 | 3000 | 10.1 ± 1.9 |
| 1:200 | 3400 | 9.7 ± 1.3 |
| 1:1000 | 3200 | 9.4 ± 1.2 |
| IFN-γ (100 U) + LPS (5 ng/ml) | 6800 | 74.1 ± 0.6 |
| IFN-γ (100 U) + Virulizin: | | |
| 1:5 | 512 | 46.9 ± 0.6 |
| 1:10 | 625 | 57.3 |

In vitro synergy of Virulizin™ with LPS for nitric oxide (NO) was addressed in the same procedure as above, except NO was determined in the supernatant of the treated macrophages. As above, the assay for NO is spectrophotometric and uses a Greiss reagent. As noted in the table above, LPS causes some release of NO (9 μm). VIRULIZIN™ in synergy with LPS induces a marked increase in NO production (13–27 μm) to dilutions of 1:40. VIRULIZIN™ by itself did not induce release of NO by macrophages.

In vitro synergy of Virulizin™ with IFN-γ for TNF-α release was studied, using the same peritoneal mouse macrophages derived from C57BL/6 mice treated as above. The data are included in the table above concerning "Synergistic Combinations." As shown, peritoneal mouse macrophages phages exhibit a baseline release of TNF-α after 24 hours of in vitro culture. The same macrophages stimulated with either LPS or IFN-γ release almost 3000 pg/ml of TNF-α. When VIRULIZIN™ and IFN-γ were added together, the release of TNF-α was diminished. By comparison, the combination of LPS and IFN-γ have an additive effect on TNF-α release.

In vitro synergy of Virulizin™ with IFN-γ for NO release was studied, using the same peritoneal mouse macrophages derived from C57BL/6 mice treated as above. The data are included in the table above concerning "Synergistic Combinations." As shown, LPS and IFN-γ alone each enhanced NO production (9 and 7 μm, respectively). VIRULIZIN™ added to IFN-γ induced a marked increase in NO production (47–57 μm) that almost equaled the combination of LPS and IFN-γ (74 μM). The results are consistent with the conclusion that VIRULIZIN™ in combination with IFN-γ enhances NO production but inhibits TNF-α release.

In vivo production of TNF-α over 72 hours was studied on macrophages harvested from C57BL/6 mice that, prior to harvest, were treated with nothing, injected intraperitoneally 72 hours previously with 1.5 and 4% protease peptone, or injected intraperitoneally 72, 48, or 24 hours previously with 1.0 ml Virulizin™ diluted 1:10 in PBS. The macrophage monolayers were treated in vitro for 24 hours with IFN-γ (50 μ/ml), LPS only (5 ng/ml), or the combination thereof. TNF and NO were determined as recited above. The data are presented in Table XX.

TABLE XX

TNF and No Release From Macrophages Harvested From Treated Mice

| Macrophages Harvested from Mice Injected With | In Vitro Stimulant | TNF (pg/ml) | NO (μM) |
|---|---|---|---|
| Nothing | Medium | 315 | 0 |
| | IFN-γ | 402 | 25.8 ± 1.6 |
| | LPS | 3,750 | 1.9 ± 0.2 |
| | IFN-γ + LPS | 6,300 | 40.9 ± 3.8 |
| Protease Peptone (72 hrs prior) | Medium | 335 | 0.9 ± 0.5 |
| | IFN-γ | 838 | 48.6 ± 1.7 |
| | LPS | 5,975 | 23.2 ± 3.4 |
| | IFN-γ + LPS | 10,875 | 55.8 ± 1.9 |
| Virulizin (72 hrs prior) | Medium | 258 | 1.2 ± 0.6 |
| | IFN-γ | 425 | 37.5 ± 2.6 |
| | LPS | 3,300 | 4.0 ± 0.9 |
| | IFN-γ + LPS | 4,650 | 54.0 ± 0.9 |
| Virulizin (48 hrs prior) | Medium | 350 | 8.5 ± 1.8 |
| | IFN-γ | 560 | 62.0 ± 2.5 |
| | LPS | 5,300 | 36.5 ± 1.2 |
| | IFN-γ + LPS | 12,475 | 58.5 ± 1.6 |
| Virulizin (24 hrs prior) | Medium | 248 | 2.9 ± 2.1 |
| | IFN-γ | 475 | 44.1 ± 0.7 |
| | LPS | 9,025 | 12.5 ± 2.4 |
| | IFN-γ + LPS | 12,375 | 52.8 ± 0.6 |

As described, the release of TNF-α from macrophages was examined in the absence of a stimulus or with IFN-γ, LPS, or LPS/IFN-γ after 24 hrs in vitro culture. Mouse peritoneal macrophages were shown to release little TNF-α after in vivo stimulation with VIRULIZIN™. When the harvested macrophages were exposed to IFN-γ at 24 and 48 hrs prior to testing, they showed a small increase in production of TNF-γ. By contrast, harvested macrophages stimulated with LPS at 24 and 48 hrs, but not 72 hrs prior to testing, showed enhanced release of TNF-γ. Likewise, there was a synergistic effect of LPS and IFN-γ on harvested macrophages that were stimulated 24 and 48 hrs but not 72 hrs before testing.

In vivo production of NO over 72 hrs was studied with macrophage cells and tests under the same conditions described above with respect to TNF-α production. There was a small spontaneous release of NO measured at 24 and 48 hrs after intraperitoneal injection of VIRULIZIN™ (hereinafter IP Virulizin™). When the harvested cells were incubated with IFN-γ, there was a marked release of NO, and the harvested macrophages that had IP VIRULIZIN™ at 24 and 48 hrs prior to testing showed an exponential increase in release of NO, which fell back at 72 hrs towards the baseline values of IFN-γ alone. When the harvested cells were stimulated with LPS, they showed a markedly enhanced output of NO, which was once again observed for the 24 and 48 hrs VIRULIZIN™ treated macrophages compared to macrophages that had not received IP VIRULIZIN™. The harvested macrophages that had received IP VIRULIZIN™ 72 hrs before responded no differently than macrophages that had no VIRULIZIN™ pretreatment. Finally, when harvested macrophages pretreated with IP VIRULIZIN™ were incubated with LPS/IFN-γ, they showed enhanced production of NO compared to macrophages not so pretreated. The maximum response was with macrophages pretreated with VIRULIZIN™ 48 hrs before harvesting and testing.

EXAMPLE 9

This example illustrates the activation of monocytes and macrophages with the composition of Example 1 and methods for testing same.

Investigations have shown that the composition of Example 1 will activate normal monocytes to demonstrate cytotoxicity towards the Chang hepatoma cell line, which is used to measure monocyte toxicity, and that the monocytes and macrophages from cancer patients (e.g., those afflicted with cancers of the cervix, ovaries, ear/nose/throat, and endometrium/uterus, and chronic myelogenous leukemia) have been stimulated by the composition to attack and destroy tumor cells derived from the same patient.

More particularly, the monocyte tumoricidal function has been tested in the presence of the composition of the invention and the basic procedure for these experiments is outlined below. This procedure has been named the "Monocyte/Macrophage Cytotoxicity Assay to Cell Lines and Autologous Tumor Cells," or "Cytotoxicity Assay" for short.

The method requires isolation of monocytes/macrophages phages, which is accomplished as follows: Venous blood is collected aseptically in heparinized Vacutainer tubes. Sterile preservative-free heparin is added to a final concentration of 20 units/ml. The blood is diluted 3:1 in Hanks balanced salt solution (HBSS), layered onto lymphocyte separation medium and centrifuged to obtain a band of peripheral blood mononuclear cells (PBMNs). After centrifugation, the mononuclear cell layer is recovered from the interface, washed twice in medium (medium is Roswell Park Memorial Institute [RPMI] 1640 media supplemented with 10% heat-inactivated fetal bovine serum, 50 units/ml penicillin, and 50 µg/ml streptomycin) and monocytes are enumerated by latex ingestion. Monocytes are isolated by adherence in 96-well plastic plates (for 2 hours at 37° C., followed by two cycles of washing with medium). Adherent cells are estimated to be greater than 90% monocytes. Wells containing adherent cells are incubated overnight in the presence of VIRULIZIN™ (1:10–1:200 final dilution). Then, adherent cells are washed to remove VIRULIZIN™ and incubated overnight with tumor cells. The tumor cells are maintained in medium in which endotoxin concentration is guaranteed by the manufacturer to be low and is non-stimulatory in the assay.

For studies using a standard cell line, $^{51}$Cr (chromium) labelled Chang hepatoma cells are used because this cell line is insensitive to natural killer cell cytotoxicity. These hepatoma target tumor cells are added to adherent cell monolayers at effector:target (E:T) cell ratios of 20:1 to 15:1. This E:T ratio is used because it falls well into the plateau range on a curve prepared by varying the E:T ratio from 5:1 to 30:1. After 24 hours, supernatants are collected and $^{51}$Cr release is quantitated. The percent specific cytotoxicity is calculated as:

$$\% \text{ specific release} = \frac{E - S}{T - S} \times 100$$

In the equation above, E=CPM released from target cells in the presence of effector cells; S=CPM released from target cells in the absence of effector cells; T=CPM released from target cells after treatment with 2% sodium dodecyl sulfate).

For studies using autologous tumor cells, these cells are obtained from surgical biopsies, labelled with $^{51}$C, and used in the same way as the hepatoma cells described above.

Preparation of peritoneal and alveolar macrophages is done by the methods described in Braun et al., *Cancer Research*, 53, 3362–3365 (1993).

Using this protocol, the composition was found to cause monocytes from healthy donors to exert cytotoxicity toward the Chang hepatoma cell line. Subsequently, whether monocytes and macrophages from a cancer patient could be stimulated by the composition to attack and destroy their own particular tumor was investigated. Using similar protocols as described for the standard cell line (Chang hepatoma cells), monocytes and/or peritoneal macrophages from cancer patients were isolated. Peritoneal macrophages were isolated from peritoneal fluids collected at the time of laparoscopy. The composition was found to activate peripheral monocytes and peritoneal macrophages from a patient with cervical cancer to produce cytotoxicity against the patient's own tumor cells. This effect was comparable to or better than that produced by the combination of IFN and LPS. Peritoneal macrophages from a patient with ovarian cancer were also found to be stimulated by the composition to attack and destroy the ovarian tumor cells in culture.

Monocyte/MacroPhage Studies with the Composition

Because the screening procedures demonstrated that the composition does not stimulate lymphocyte functions but can stimulate monocyte functions, subsequent studies were aimed at further characterization of the monocyte/macrophage stimulatory activities of the composition. A number of comparative studies aimed at determining the dose response characteristics of the composition in stimulating monocyte/macrophage tumoricidal function were performed as well as testing different batches of the compound. The main emphasis of the studies was to test the capacity of the composition to simulate tumoricidal function in monocytes and macrophages from different anatomical sites of cancer patients. For these investigations, the following were relied upon: (1) peripheral blood monocytes from cancer patients and control subjects; (2) alveolar macrophages from lung cancer patients and control patients with non-malignant lung diseases; and (3) peritoneal macrophages from patients with gynecological malignancies.

Figure 14:
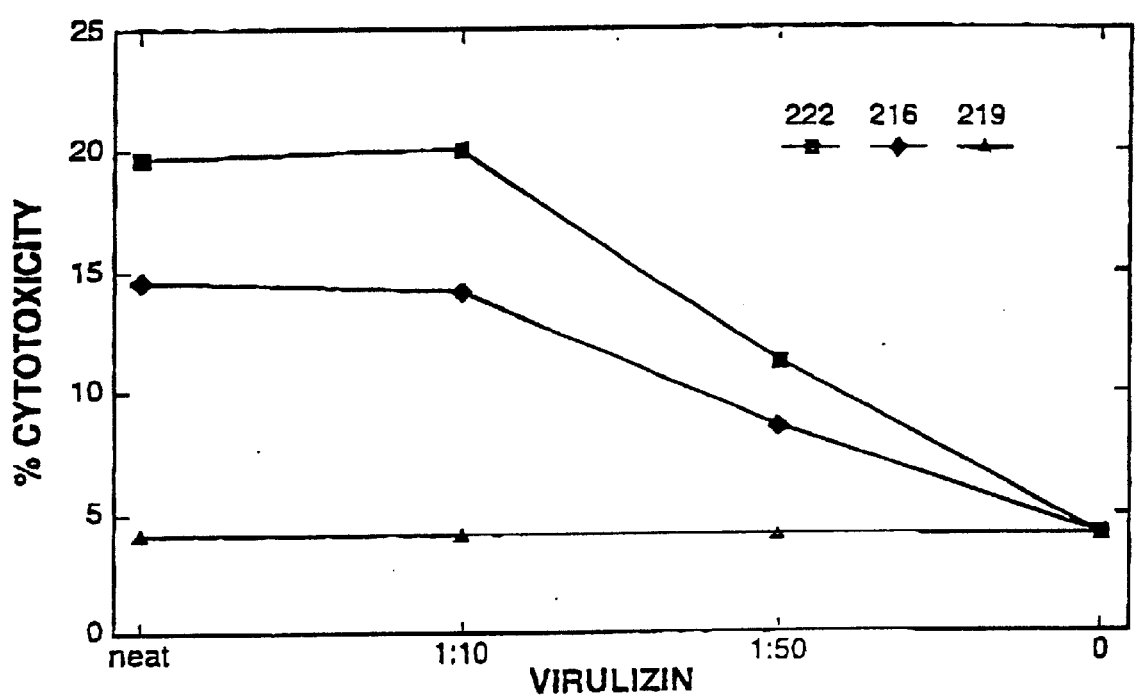
FIG. 14 is a graph showing dose response of the composition of the invention in stimulating peripheral blood monocyte function.

Dose response studies with different batches of the composition, all prepared in accordance with Example 1, were completed. These studies relied on peripheral blood monocytes to test the stimulatory activities of different doses and different batches of the composition (Batch nos. 216, 219 and 222). Each batch of the composition was tested without dilution (neat), a 1:10 dilution and a 1:50 dilution of material. The results are depicted graphically in FIG. 14.

Batch #222 and #216 were shown to stimulate monocyte tumoricidal function, however, Batch #219 did not. It appeared that #222 was superior to #216 in these preliminary investigations. Batch #222 appeared to stimulate equivalent levels of tumoricidal function at the undiluted (neat) and 1:10 dilutions, but lesser, still detectable activity at the 1:50 dilution. Batch #216 gave the greatest stimulation of tumoricidal function at the undiluted (neat) concentration, with less activity at the 1:10 dilution and no detectable activity at the 1:50 dilution. As stated above, Batch #219 did not elicit detectable monocyte tumoricidal function at any concentration tested.

Tumoricidal function in peripheral blood monocytes was also evaluated. Tests were performed on 4 peripheral blood monocyte samples from control subjects. These tests utilized an optimal stimulating concentration of the composition (1:10 dilution of batch #222) and an optimal stimulating concentration of IFN-γ plus LPS. The target cells in these studies were a cultured, NK-insensitive cell line, namely the Chang Hepatoma. Results are presented in the following table.

| Stimulant (E/T-20/1) | % Cytotoxicity |
| --- | --- |
| Medium | 5.4 ± 1 |
| IFN-γ + LPS | 18.6 ± 4 |
| Composition | 22.3 ± 6 |

A test was also performed on 1 monocyte sample from a patient with cervical cancer. This test was important because the patient's own tumor cells were available to be used as target cells in the assay. As before, this test utilized an optimal stimulating concentration of the composition (1:10 dilution of Batch #222) and an optimal stimulating concentration of IFNγ plus LPS. Also, the effector/target cell ratio was reduced to 15/1 to conserve patient tumor cells. Results of this test are presented in the following table.

| Stimulant (E/T-20/1) | % Cytotoxicity |
| --- | --- |
| Medium | 5.5 |
| IFN-γ + LPS | 14.4 |
| Composition | 20.9 |

In the peripheral blood monocytes from control subjects, the composition stimulated monocyte tumoricidal function against the Chang Hepatoma cells at a level equal to or greater than the level elicited by an optimal stimulating concentration of IFN-γ+LPS. In the peripheral blood monocytes from a patient with cervical cancer, the composition stimulated tumoricidal function against the patient's own tumor cells at a level which exceeded that elicited by IFN-γ plus LPS by greater than 30%.

Tumoricidal function in peritoneal macrophages from patients with gynecological malignancies was tested. These tests were performed on peritoneal macrophage samples isolated from lavage fluids of 1 patient with cervical cancer and 1 patient with ovarian cancer. These tests were performed with the patient's own tumor cells as target cells in the assay. As before, an optimal stimulating concentration of the composition (1:10 dilution of Batch #222) and an optimal stimulating concentration of IFN-γ plus LPS were compared. Also, the effector/target cell ratio was reduced to 15/1 to conserve patient tumor cells. The resulting data were:

| Stimulant | Cervical Cancer | Ovarian Cancer |
| --- | --- | --- |
| Medium | 8.2 | 0.6 |
| IFN + LPS | 29.8 | 4.1 |
| Composition | 13.2 | 8.9 |

These test results highlighted the fact that the local tumor environment may be a determinant of the response of immune cells to immunological activators. In this case of cervical cancer, there was no pathological evidence of malignant disease within the peritoneal cavity and the development of tumoricidal function against the autologous tumor was better with IFN-γ and LPS combined than with the composition. In the patient with ovarian cancer, there was a significant tumor in the peritoneal cavity. The response against the patient's own tumor to IFN-γ and LPS combined was minimal at best, whereas the response to the composition was greater.

Tumoricidal function in alveolar macrophages from lung cancer patients and control subjects was tested. These tests were performed on alveolar macrophage samples isolated from bronchoalveolar lavage fluids of a patient with non-small cell lung cancer and three (3) patients with non-malignant diseases of the lung. These tests utilized an optimal stimulating concentration of the composition (1:10 dilution of batch #222) and an optimal stimulating concentration of IFN-γ and LPS combined. The target cells in these studies were the Chang Hepatoma cells and the effector/target cell ratio was 20/1. The resulting data were:

| Stimulant | Cancer Patients | Control |
| --- | --- | --- |
| Medium | 2.6 ± 2 | 19.5 ± 4 |
| IFN-γ + LPS | 10.9 ± 13 | 1.2 ± 5 |
| Composition | 5.2 ± 2 | 18.6 ± 8 |

The results were consistent with the observation that alveolar macrophages from lung cancer patients are impaired in their development of tumoricidal function in response to conventional macrophage activators such as IFN-γ+LPS. The results showed that the tumoricidal function of alveolar macrophages from lung cancer patients is greatly reduced compared to control subjects. The data presented earlier indicated VIRULIZIN™ to be a poor stimulator of alveolar macrophages. Further investigation with alveolar macrophages from non-small cell lung cancer patients is presented in Example 23. The activity in alveolar macrophages phages appears to vary with the VIRULIZIN™ preparation. Thus, alveolar macrophage cytotoxicity was elicited in only 2/7 alveolar macrophage preparations with the origin batches tested (222, 219, 216). In contrast, 3/4 alveolar preparations were stimulated with the later preparations (233, 238). The difference could be related to age and potency of the preparation or patient variability. Accordingly, the composition can activate tumoricidal activity in alveolar macrophages.

The preliminary in vitro tests with the composition demonstrate that it is a macrophage activator. The material provided was able to elicit tumoricidal activity in a standard cytotoxicity assay against both an NK insensitive cell line and against freshly dissociated human tumor cells. The activity elicited was also found to be concentration-dependent in these tests. The capacity of the composition to active macrophage tumoricidal function in vitro was comparable to that of the best macrophage activating combination presently available, namely, IFN-γ and endotoxin (i.e., LPS) combined. As stated above, the capacity of the composition to elicit this level of tumoricidal function in the absence of endotoxin would be considered important biologically if the material is free of endotoxin contamination. The composition is free of endotoxin contamination when tested for pyrogens by the United States Pharmacoepeia (USP) rabbit pyrogen test.

As has been found for other macrophage activators, the activity of the composition in stimulating macrophage tumoricidal function varies with the source of the macrophages phages. It appears that the composition is an excellent activator of peripheral blood monocytes being equivalent to IFN-γ+LPS with normal donors and possibly superior to IFN-γ+LPS with cancer patient donors. Malignant disease has a significant impact on the development of monocyte tumoricidal function depending on the activator used (Braun et al., (1991)). One determinant of the biological activity of different macrophage activators in cancer patients monocytes is the sensitivity of the activator to arachidonic acid metabolism and the secretion by the cell of prostaglandins. From these initial studies with the composition, it appears that activity elicited with the compound is not sensitive to the inhibitory effects of prostaglandins. If prostaglandin insensitivity can be proven definitively for cancer patient monocytes stimulated with the composition, this would be considered important therapeutically because the effectiveness of many other biological activators is limited by prostaglandins. Preliminary studies with 2 specimens indicate that the composition may have good activity in peritoneal macrophages, particularly when malignant disease is present in the peritoneal cavity.

These preliminary results also illustrate what has been found when comparing the capacity of different activators to stimulate tumoricidal function in peritoneal macrophages of patients with different gynecological malignancies. In those studies, it was found that the presence of malignant disease within the peritoneal cavity influences the responsiveness of the peritoneal macrophages to specific activators. In patients with cervical cancer, malignant disease is not present in the peritoneal cavity in general, and thus, the response of the resident macrophages phages to IFN-γ+LPS is normal. When disease is present in the cavity, however, as in the case with ovarian cancer, the response to IFN-γ+LPS is suppressed. This is related, in part, to changes in the arachidonic acid metabolism of the peritoneal macrophages when malignant disease is present (Braun et al., 1993). The fact that the composition activates tumoricidal function in peritoneal macrophages phages from ovarian cancer patients against the patient's own tumor cells is consistent with a mechanism for activation that is independent of the arachidonic acid metabolic pathway.

Accordingly, as shown in the aforestated in vitro studies, the composition of the present invention is able to activate monocytes and macrophages to increase their immune system function.

EXAMPLE 10

This example illustrates the tumoricidal function in response to the composition of the invention and other macrophage activators in peripheral blood monocytes and peritoneal macrophages from patients with gynecological diseases.

The patient population consisted of 7 patients, 3 with benign disease and 4 with malignant disease (2 ovarian cancers, 1 endometrial cancer, and 1 cervical cancer). Samples were removed from patients at the time of surgical procedure. Preparations containing peripheral blood monocytes were isolated from blood samples using the procedure set out in Braun et al., Cancer Immunol. Immunother., 32, 55–61 (1990) and preparations containing peritoneal macrophages were isolated as set out in Braun et al., Cancer Research, 53, 3362 (1993). Tumor cell cytotoxicity in response to the composition of the invention (1:10 dilution of stock batch #222) and other activators, namely IFN-γ (100 U/ml), IL-12 (500 U/ml), and monocyte-CSF (500 U/ml) was assessed using the monocyte cytotoxicity assay described in Braun et al.

The results as shown in the following table demonstrate that the composition of the invention stimulates tumoricidal function in both the peripheral blood monocytes and the peritoneal macrophages from patients with malignant and non-malignant gynecological diseases. The results are recited as percentage of tumor cytotoxicity (±S.E.) at a monocyte/tumor cell ratio of 15:1.

| Stimulation of Peripheral Blood Monocytes and Peritoneal Macrophages | | |
|---|---|---|
| Activator | Peripheral Blood Monocytes | Peritoneal Macrophage |
| Medium | 8.6 ± 3 | 3.1 ± 1 |
| Gamma Interferon | 18.3 ± 2 | 9.5 ± 1 |
| Interleukin-12 | 26.0 ± 4 | 8.5 ± 2 |
| Monocyte-CSF | 16.0 ± 2 | 7.0 ± 2 |
| Composition of the Invention (Virulizin) | 23.0 ± 6 | 12.5 ± 2 |

Accordingly, the tumor cytotoxicity elicited by the composition of the invention is equal to or greater than that elicited by the other biological stimulators which were tested.

EXAMPLE 11

This example illustrates the effect of indomethacin, a prostaglandin synthesis inhibitor, on the development of tumoricidal function in response to the composition of the invention; the impact of other macrophage activators on peripheral blood monocytes from cancer patients was also investigated.

Samples from the patients with malignant disease in Example 10 were tested using the assay system as described in Example 10 with the exception that indomethacin (up to 5 ng/ml) was simultaneously added with the composition of the invention, IL-12 (500 U/ml), and monocyte-CSF (500 U/ml).

The results as shown in the following table indicate that indomethacin augments cytotoxicity in response to IFN-α, GM-CSF and M-CSF.

| Indomethacin Augmentation of Cytotoxicity | | |
|---|---|---|
| Activation Conditions | No. Donors | % Cytotoxicity |
| IFN-γ | 23 | 11.9 ± 9 |
| IFN-γ + Indomethacin | 23 | 25.2 ± 17 |
| GM-CSF | 10 | 7.8 ± 6 |

-continued

Indomethacin Augmentation of Cytotoxicity

| Activation Conditions | No. Donors | % Cytotoxicity |
|---|---|---|
| GM-CSF + Indomethacin | 10 | 17.8 ± 8 |
| PMA | 6 | 27.3 ± 14 |
| PMA + Indomethacin | 6 | 22.0 ± 17 |
| IL-12 | 3 | 24.7 ± 5 |
| IL-12 + Indomethacin | 3 | 25.6 ± 6 |
| M-CSF | 3 | 14.31 ± 3 |
| M-CSF + Indomethacin | 3 | 19.0 ± 3 |
| Composition (Virulizin) | 4 | 18.7 ± 6 |
| Composition (Virulizin) + Indomethacin | | 16.4 ± 6 |

Thus, the development of tumoricidal function in response to IFN-γ, GM-CSF, and M-CSF was regulated by an indomethacin-sensitive function. In contrast, the development of tumoricidal function in response to Phorbol Ester (PMA)), IL-12 and the composition of the invention was not regulated by an indomethacin-insensitive function, i.e., indomethacin did not augment cytotoxicity in response to the composition of the invention, IL-12 and PMA.

EXAMPLE 12

This example illustrates the effect of prostaglandin $E_2$ on the development of tumoricidal function in response to the composition of the invention in the presence of indomethacin.

The subject population consisted of one normal and nine patients (one healthy, one patient with a pancreatic tumor, two patients with head and neck tumors, one with endometriosis, and four with HIV). Preparations containing peripheral blood monocytes were isolated from blood samples from the patients using the procedure set out in Braun et al. (1990). Tumor cell cytotoxicity in response to the composition of the invention (1:10 dilution of stock batch #222) and indomethacin (up to 5 ng/ml), with or without $PGE_2$ ($10^8$M), was assessed using the monocyte cytotoxicity assay described in Braun et al., id.

The results are presented in the following table, wherein the results are recited as percentage tumor cytotoxicity at a monocyte/tumor cell ratio of 15:1.

| Diagnosis | Composition (Virulizin) | Composition (Virulizin) + Indomethacin | Composition (Virulizin) + Indomethacin + PGE |
|---|---|---|---|
| HIV | 6 | 7 | 8 |
| HIV | 15 | 12 | 19 |
| HIV | 21 | 16 | 20 |
| HIV | 23 | 22 | n.d. |

The data in the following table show that pathophysiological levels of $PGE_2$ ($10^{-8}$M) failed to suppress the level of tumoricidal function that developed in response to the composition of the invention. This conclusion is in contrast to the capacity of $PGE_2$ to suppress tumoricidal function in monocytes stimulated with IFN-γ (Braun et al. (1993)).

EXAMPLE 13

This example illustrates the development of tumoricidal function against autologous tumor cells in monocytes stimulated with the composition of the invention.

Preparations containing peripheral blood monocytes were isolated from blood samples from 7 patients (three ovarian cancers, one endometrial cancer, one cervical cancer and two ENT cancers) using the procedure set out in Braun et al. (1990). Tumor cell cytotoxicity in response to the composition of the invention (1:10 dilution of stock batch #222) and indomethacin (up to 5 ng/ml), with or without PGE ($10^{-8}$ M) was assessed using the monocyte cytotoxicity assay described in Braun et al. (1990), with the exception that the patient's tumor cells were used in place of the Chang hepatoma cells. The patient's tumor cells were treated with collagenase and DNase, single cell preparations were prepared, and the cells were labelled as described in Braun et al. (1990).

The results shown in the following table demonstrate that the composition of the invention is capable of activating the patient's own monocytes to kill the patient's tumor.

Monocyte Tumoricidal Function Induced By Composition of Example 1

| Diagnosis | Culture Conditions | % Tumor Cytotoxicity (E/T = 15/1) |
|---|---|---|
| Ovarian Cancer | Medium | 2 |
| | Composition (Virulizin) | 11 |
| Ovarian Cancer | Medium | 1 |
| | γ-Interferon + LPS | 4 |
| | Composition (Virulizin) | 9 |
| Ovarian Cancer | Medium | 0 |
| | γ-Interferon + LPS | 14 |
| | Composition (Virulizin) | 11 |
| Endometrial Cancer | Medium | 6 |
| | γ-Interferon + LPS | 14 |
| | Composition (Virulizin) | 21 |
| Cervical Cancer | Medium | 8 |
| | γ-Interferon + LPS | 30 |
| | Composition (Virulizin) | 13 |
| ENT Cancer | Medium | 11 |
| | γ-Interferon + LPS | 12 |
| | Composition (Virulizin) | 25 |
| ENT Cancer | Medium | 18 |
| | γ-Interferon + LPS | 11 |
| | IL-12 | 11 |
| | M-CSF | 3 |
| | Composition (Virulizin) | 35 |

The experimental results in Examples 10 to 13 indicate that the composition of Example 1 is capable of activating monocytes to express tumoricidal function; it works in the blood with peritoneal macrophages; and, the results are consistent with it not being subject to the inhibitory effects of prostaglandins, which is one of the principle forms of immunosuppression in patients. The experimental data also support the utility of the composition in the treatment of peritoneal, alveolar, and gynecological malignancies.

EXAMPLE 14

This example illustrates the results of assays conducted to estimate protein within the composition.

Protein estimation of the composition was done using the Pierce Micro BCA Protein determination technique (Smith et al., Anal. Biochem., 150, 76–85 (1985)). A 10 μl sample of a batch of the composition was made up to 1 ml with distilled water. Five concentrations of bovine serum albumin (0.150 μg/ml) was also made up to be used as standards. As a blank, 0.1 N NaOH was used. To all these samples was added a mixture of BCA (2% bicinchonic acid sodium salt; Pierce), 4% copper sulfate and microreagent A ($NaCO_3$, $NaHCO_3$, Na tartrate in 0.2 N NaOH). The sample mixtures were incubated for 1 hr at 60° C., cooled, and the resultant absorbency read at 562 nm using a spectrophotometer. The amount of protein in the test sample was then compared to the plotted standard curve and the appropriate calculations made. The protein concentration of the composition was found to be low and estimated to be 32 µg/ml.

EXAMPLE 15

This Example demonstrates, in summary, the following: (1) the composition has TNF-α releasing activity and the TNF-α releasing activity is not related to any contamination with endotoxin; (2) priming of macrophages enhances the ability of the composition to stimulate release of TNF-α; and (3) the hyperosmolarity of the composition is not responsible for TNF-α releasing activity.

To test whether an endotoxin effect was associated with the biological activity noted above for the composition of Example 1, further composition experiments were performed with polymyxin added to the reactants. Polymyxin inhibits the action of endotoxin on leukocytes. The following table and succeeding notes recite the composition experiment performed and its results.

Absence of Endotoxin for TNF-2 Releasing Effect and Enhancement of Release With Macrophage Priming

| Sample Tested | Additive | TNF Released (pg/ml) | |
|---|---|---|---|
| | | Total | -LPS |
| LPS | Polymyxin | 11 ± 7 | 0 |
| | None | 517 ± 118 | 0 |
| Composition (#B0213) | Polymyxin | 1591 ± 413 | 1581 |
| | None | 5256 ± 2585 | 4738 |

Notes:
1. Total TNF released is correct for TNF release by 1640 medium.
2. Polymyxin concentration: 50,000 units/ml.
3. Composition volume: 200 µl.
4. With polymyxin, 8 patients tested. With no additive, 3 patients tested.
5. LPS concentration: 50 ng/10 µl.

The results show that polymyxin completely inhibits the LPS-induced release of TNF-α. In the absence of polymyxin, LPS induces 517 pg/ml of TNF-α, whereas in the presence of polymyxin, 11 pg/ml of TNF-α is released. The composition, on the other hand, releases 1591 pg/ml of TNF-α in the presence of polymyxin. In the absence of polymyxin, LPS and the composition show more than just an additive effect of the stimulators, suggesting that the composition acts with greater intensity when macrophages are primed.

Absence of Effect of Hyperosmolarity on TNF-2 Release

| Batch # | pH | Osmolarity (mOsm) |
|---|---|---|
| Concentrated: | | |
| B0222 | pre-pH | 411 |
| B0222 | pH adjusted | 581 |
| B0216 | pH adjusted | 872 |
| B0219 | pH adjusted | 886 |
| Nonconcentrated: | | |
| B0221 | pre-pH | 652 |
| B0221 | pH adjusted | 533 |
| B0213 | pH adjusted | 675 |
| B0225 | pH adjusted | 590 |
| B0226 | pH adjusted | 540 |
| BC 11-06 | pH adjusted | 445 |
| BC 11-09 | pH adjusted | 603 |

The osmolarity of different batches was determined using standard methods. The results are shown in the previous table. B0213 is moderately high at 675 mOsm. B0222, shown to have TNF releasing activity even better than B0213, is less hyperosmolar, 581 mOsm. The fractions B0226, BC11-06 and BC11-09 range from 540 to 603 mosm. The effect of the hyperosmolarity of the composition on TNF-α releasing activity was also studied. It was found that the composition, when adjusted for osmolarity, even to the point of being hypoosmolar, continued to release TNF-α.

EXAMPLE 16

This example illustrates toxicity studies regarding the composition of the present invention. Preliminary toxicity studies were conducted on a variety of animal species, as tabulated below.

All animals (listed in the following table) were assessed on the basis of daily clinical observation while receiving the injections of the composition on days 14, 21 and 30 thereafter. Hematologic data was collected every third day for the first 30 days and once monthly thereafter. No adverse effects were noted in any of the over 358 animals included in this study throughout the period that injections were administered or during the follow-up period (one month for all species except the dogs which were followed for 4 months).

| Animal | Quantity | Dose |
|---|---|---|
| White mice | 100 | 0.2 ml i.m. at 3-day intervals 4 times |
| Male Wistar rats | 100 | 2.0 ml i.m. at 3-day intervals 4 times |
| Golden hamsters | 60 | 1.5 ml i.m. at 4-day intervals 4 times |
| Guinea pigs | 60 | 3.0 ml at 3-day intervals 4 times |
| Rabbits | 15 | 5.0 ml i.m. at 3-day intervals 4 times |
| Cats | 10 | 3.0 ml i.m. at 3-day intervals 6 times |
| Dogs | 12 | 2 ml/kg i.m. given once - observed for 4 months |

A second toxicity study was conducted to determine the effect of a single large intramuscular dose of the composition. Thirteen Sprague Dawley rats received a single intramuscular dose of 5 ml/kg of the composition. Three rats were observed for 7 days. Ten rats were observed for 14 days followed by euthanasia and necropsy. No symptoms of toxicity were observed in either group and no gross pathologic findings were observed in the animals that were necropsied. Based on these observations the $LD_{50}$ for intramuscular administration of the composition in rats was determined to be greater than 5 ml/kg.

Another toxicity trial was conducted by the Ontario Veterinary College, wherein the composition was administered to two mixed breed dogs. The protocol is summarized in the following table:

| Animal | Age and Weight | Dose 1 | Dose 2 | Dose Interval |
|---|---|---|---|---|
| Male Mixed Breed | Adult 5 kg | 5.5 ml i.m. | 0.6 ml i.m. | 7 days |
| Female Mixed Breed | 6 months 13 kg | 12.5 ml i.m. | 1.3 ml i.m. | 7 days |

In each case, one dose was given in the right rear leg and the second dose 7 days later was given in the left rear leg. Both dogs were observed for 14 days after the first injection. Appetite, activity, temperature, pulse rate, and respiratory rate were monitored twice daily throughout the study. Routine urinalyses, hematology and serum chemistry profiles were performed at the following time points: pretreatment and 24 hours, 72 hours, 7 days and 14 days after the first injection. Neither animal showed signs of pain associated with either injection. There was no evidence of anaphylaxis associated with the second injection. No abnormalities or changes in physical or laboratory parameters were observed that could be attributed to the drug. The drug appeared to be well tolerated by healthy dogs.

A 17-day repeat dose toxicity study was carried out with VIRULIZIN™ in conjunction with an animal model study at the Ontario Cancer Institute. The model used female C57Bl mice. There were 4 groups as follows (IM=intramuscular, IP=intraperitoneal):

| Group # | Treatment | Dose Volume | Number/Group |
|---|---|---|---|
| 1 | Saline, IM | 0.05 ml | 10 |
| 2 | Virulizin ™, IM | 0.05 ml | 10 |
| 3 | Virulizin ™, IM | 0.05 ml X2 | 10 |
| 4 | Virulizin ™, IP | 0.5 ml | 10 |

Each group of mice were injected at day 0 with $5 \times 10^3$ of B16F1 melanoma cells plus microspheres. On each of the first 17 days, each group received daily injections of Virulizin™ or saline, as above. On day 18, the animals were sacrificed.

Prior to sacrifice, food intake, weight gain, and behavior were normal. In addition, there was no evidence of toxicity causing changes observable by light microscopy in any of the organs examined, which were: large intestine, spleen, stomach, pancreas, urinary bladder, liver, brain, kidneys, small intestine, and heart. Food intake and behavior were normal. Weight gain was normal.

A 13-week repeat dose toxicity study in Fischer-344 rats (total of 40 males and 40 females) was carried out administering VIRULIZIN™ IM three times per week for 13 weeks. The largest dose was 1.1 ml/kg, about 20× the human dose. Animals were subjected to full histopathology after 13 weeks. The only treatment related finding observed was a small decrease in mean body weight gain in the 20× dose group as compared to controls. No toxicity was demonstrated.

EXAMPLE 17

This example illustrates the clinical use of the composition of the invention for the treatment of various malignant tumors in companion animals.

Eleven cats and ten dogs with advanced neoplastic disease, none of which were responding to conventional therapy, were treated with the composition given intramuscularly in weekly doses. The following table summarizes the individual clinical cases in this study, as follows:

Summary of Cases of Animals with Malignant Neoplasms

| No. | Name and Age | Species/Sex | Diagnosis | From–To | Injections | Surgeries | Results |
|---|---|---|---|---|---|---|---|
| 1 | Bandit-13 | Canine-M/n | Orinasal fibrosarcoma | 01/31/87–05/19/87 | 16 | 3 | Minor partial response Progressive disease Euthanasia |
| 2 | Bob-5 | Feline-M/n | Focal osseous metaplasia with osteosarcomatous development, Spindle Cell sarcoma, Feline fibrosarcoma, Squamous, Recurrent Spindle Cell Sarcoma-invasive (necropsy diagnosis) | 04/02/87–08/10/87 11/08/88–02/21/90 | 18 69 | 11 | First recurrence 16 months all complete response |
| 3 | J.D.-7 | Canine-M/n | Oral amelanotic melanoma, benign papilloma, recurrent round cell sarcoma | 03/02/87–08/24/87 12/14/87–04/05/88 04/04/89–08/01/89 11/09/89–11/30/89 12/24/90 25029189 | 26 20 14 17 15 4 94 | 3 | Complete response. Currently asymptomatic (4 months) |
| 4 | Mimi-7 | Canine-F/s | Recurrent invasive fibrosarcoma | 02/27/87–08/10/87 | 22 | 5 | Stable (no change); limb amputation. No recurrence. |
| 5 | Goliath-17 | Feline-M/n | Malignant melanoma fibrosarcoma | 04/02/87–09/14/87 11/30/87–07/25/88 | 22 31 | 3 | Initial major partial response. Subsequent minor partial response. Progressive disease. Euthanasia. |
| 6 | Diablo-15 | Feline-M/n | Malignant squamous cell carcinoma | 05/28/89–06/29/87 | 5 | 1 | Initial minor response then progressive disease. Euthanasia. |

-continued

Summary of Cases of Animals with Malignant Neoplasms

| No. | Name and Age | Species/Sex | Diagnosis | From–To | Injections | Surgeries | Results |
|---|---|---|---|---|---|---|---|
| 7 | Oliver-10 | Canine-M/n | Malignant round cell sarcoma | 02/24/89–05/30/89 | 12 | 1 | Complete response. Asymptomatic 1 year. |
| 8 | Karu-7 | Canine-M/n | Mucinous intestinal carcinoma-metastatic | 06/02/87–09/14/87 | 14 | 1 | Minor partial response. Then progressive disease. Euthanasia |
| 9 | Puppy-12 | Feline-M/n | Ceruminous gland adenocarcinoma | 07/22/88–10/04/88 | 10 | 1 | Minor partial response. Then progressive disease. Died 10/10/87. |
| 10 | Grandpa-16 | Feline-M/n | Anaplastic neoplasm high grade malignancy | 01/17/89–03/20/89 | 9 | 2 | Minor partial response. Then progressive disease. Euthanasia 03/26/87 |
| 11 | Sam-7 | Feline-F/s | Mediastinal lymphoma | 11/02/87–12/21/87 | 7 | 0 | Minor partial response. Then progressive disease. Died 12/21/87. |
| 12 | Pete-3 | Feline-M/n | Acute feline | 04/13/87–05/11/87 | 5 | 0 | Transient minor partial leukemia response. Then progressive disease. died 05/05/87. |
| 13 | Midnight-8 | Feline-M/n | Feline leukemia | 11/24/87–01/01/88 | 2 | 0 | Progressive disease. Euthanasia 01/07/88. |
| 14 | Stormy-10 | Canine-M/n | Amelanotic melanoma | 03/02/87–07/04/87 | | | Complete response, recurrence after nine months, progressive disease. |
| 15 | Penny-10 | Canine-F | Malignant melanoma | 03/02/87–07/08/87 | | | Partial response(?) progressive disease. |
| 16 | Muky-5 | Feline-F | Anaplastic carcinoma | 02/09/87–06/08/87 | 6 | 3 | Complete response, recurrence after three months stable. |
| 17 | George-10 | Feline-M | Malignant melanoma | 03/02/87–08/04/87 | 15 | 1 | Minor partial response, no change after 26 months stable. |
| 18 | Simon-13 | Canine-M | Benign prostatic hyperplasia | 04/02/87–08/31/87 | 10 | 1 | Minor partial response. |
| 19 | Tequila-14 | Canine-F/s | Malignant intestinal adenocarcinoma | 11/24/89–08/09/90 | 35 | 1 | Minor partial response. Euthanasia 08/09/90. |
| 20 | Sheba-12 | Canine-F/s | Invasive osteosarcoma skull | 12/06/89–06/28/90 | 25 | 1 | Initial minor partial response. Then progressive disease. Euthanasia. |
| 21 | Mesha-14 | Feline-F/s | Osteosarcoma | 02/07/89–05/06/89 | 13 | 2 | Limb amputation. Complete response. No recurrence or mestases 1 yr. |

Note: M/n means neutered male; F/s means spayed female.

The number of injections ranged from 2 to 69, with volumes up to 7.5 ml given into a single intramuscular site. Protocols of weekly injections allowed for examinations and careful monitoring of the individual cases, with diagnostic tests determined individually for each case. The clinician noted that there was no local irritation or severe allergic reactions, including anaphylaxis. The clinician and the owners of the animals did not observe any systemic adverse reactions. The investigators noted some clinical improvements consisting of minor reductions, improved appetite and activity levels, significant weight gain in a few animals and a decrease in pain and/or discomfort.

The clinical results noted in the previous table include the certain terms to describe the response of the animal to treatment with Virulizin™. These terms are defined in the following chart:

| Response | Definition |
|---|---|
| Complete Response | Disappearance of all clinical evidence of active tumors. The patient must be free of all known disease as determined by two observations not less than four weeks apart. |
| Partial Response Major | Where there is a greater than 50% reduction in the sum of the product of the perpendicular dimension of all measurable tumor with no new lesions appearing elsewhere. |
| Minor | Where there is a 25–50% shrinkage in the sum of the products of the perpendicular diameters of all measurable tumors; or subjective responses such as improvement in performance status, appetite and feeling of well being; or tumor necrosis or lysis as seen on ultrasound, x-rays, or changes in consistency and character of the tumors suggesting a decrease in adhesions and an increase in tumor mobility. |
| Stable Disease | Less than 25% increase or decrease in the size of one or more measurable lesions without tumoral lysis, or appearance of new lesions. |
| Progressive Disease | Increase of 25% in the size of one or more measurable lesions, without tumoral lysis, or appearance of new lesions. |

Six animals (3/10 canines and 3/11 felines) experienced a complete response. One animal (1/11 felines) had an initial major partial response. Eleven animals (5/10 canines and 6/11 feline) experienced a minor partial response. One animal (1/10 canines) remained stable and one animal (1/11 felines) did not respond. The clinical experience in animals clearly supports a degree of efficacy of the composition in the treatment of malignant neoplasms.

EXAMPLE 18

This example illustrates results of an Open Phase II Clinical study conducted on cancer patients.

In 1988 an Open Phase II clinical study was initiated at The Montreal General Hospital by Dr. Thirlwell and expanded to the Saskatoon Cancer Centre in 1989 under the direction of Dr. Maksymiuk. The trial remains open to patients with various advanced solid tumors who have or have not had previous treatment (excluding radiation) for their disease. Patients have been and continue to be treated three times a week with intramuscular injections of 7.5 ml of VIRULIZIN™ and have been and continue to be followed for safety, Eastern Cooperative Oncology Group ("ECOG") performance status, quality of life and survival.

As of Mar. 31, 1994, 99 patients had been treated. Adverse events were generally mild to moderate. Five patients discontinued treatment due to adverse events. No complete or partial responses were observed, although 18 patients achieved stabilization of their disease. With regard to clinical endpoints, there was no change or an improvement following 8 weeks of VIRULIZIN™ treatment in the quality of life, pain and ECOG performance status in 51%, 78% and 56%, respectively for those patients where data were available. A subgroup of patients (n=12) treated with VIRULIZIN™ for advanced pancreatic cancer showed a one-year survival rate from date of VIRULIZIN™ treatment of 29% with a median survival of 160 days. This group showed a one-year survival rate from date of diagnosis of 38% compared to 13.8% for historical controls.

Accordingly, the results from the Open Phase II Clinical study have been consistent with the in vitro and animal tests: Virulizin™ is effective to an appreciable extent for cancer therapy.

EXAMPLE 19

This example illustrates the methods and results of Pancreatic Cancer Clinical studies, in particular a Phase II trial (Protocol C02-104) with the composition of the invention for patients with measurable, biopsy-proven pancreatic cancer.

Treatment consisted of the composition prepared as in Example 1, 0.11 ml/kg (minimum dose 7.5 ml) administered with a single deep intramuscular injection to the gluteus maximus, alternating buttocks with each dose. Patients received 3 injections during the first week followed by twice-weekly injections until tumor progression.

Response was defined using standard criteria, as recited by Miller et al., Cancer, 47, 207–214 (1981). A complete response (CR) was defined as complete disappearance of all evidence of disease for at least 4 weeks. A partial response (PR) was defined as at least a 50% reduction in the product of the two largest perpendicular diameters of the largest measurable lesion, with no new lesions or progression of any lesion, for at least 4 weeks. Progressive disease was defined as a 25%, or more increase in the size of one or more measurable lesions or the appearance of new lesions. Disease not meeting criteria for response or progressive disease was termed stable disease.

A total of 22 patients were enrolled in the study, but five patients were considered inevaluable for efficacy. There were no complete or partial responses. Three patients had disease progression within the first month. Six patients had disease stabilization for more than 3 months (i.e., 3.5, 3.5, 5, 8, 12+, and 14+ months). Median survival for the entire group was 8 months from the date of diagnosis and 5 months from the start of treatment. One patient with biopsy-proven liver metastases and a CEA level of 37 ng/ml (normal is less than 3 ng/ml), had absolute stabilization of the liver metastases and CEA level for 8 months. One had stable disease for 5 months. One patient had disease relapse in her pancreatic bed 4 months after a Whipple procedure and has been stable on the composition for at least one year, with the exception of a slowing, but rising CEA. A third patient had a percutaneous stent inserted and continued to work full-time for at least 14 months with no evidence of tumor progression.

All 22 patients were evaluable for toxicity, having received a total of over 500 injections. None developed any clinical or laboratory evidence of drug-related toxicity. There was no detrimental effect on Quality of Life which generally parallelled disease activity. No significant changes in total white blood cell counts or absolute lymphocyte counts on serum immunoglobulins were seen.

Figure 6:
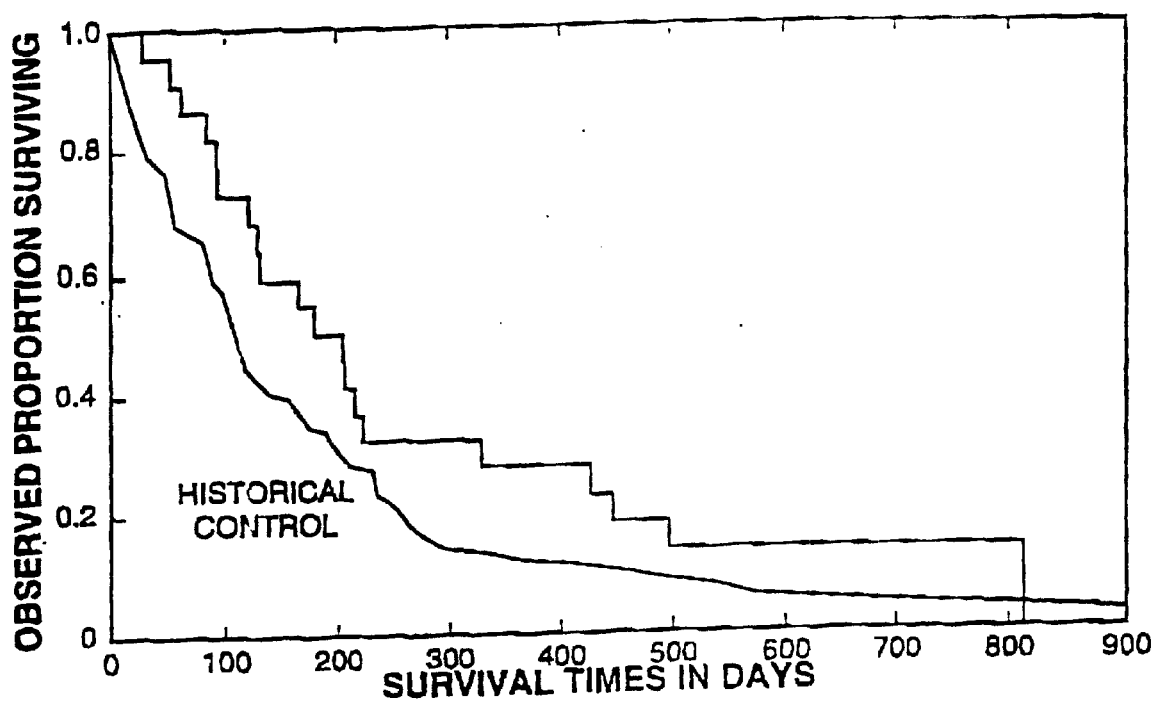
FIG. 6 is a graph showing survival taken from diagnosis of pancreatic cancer patients treated with the composition of the invention.
Figure 7:
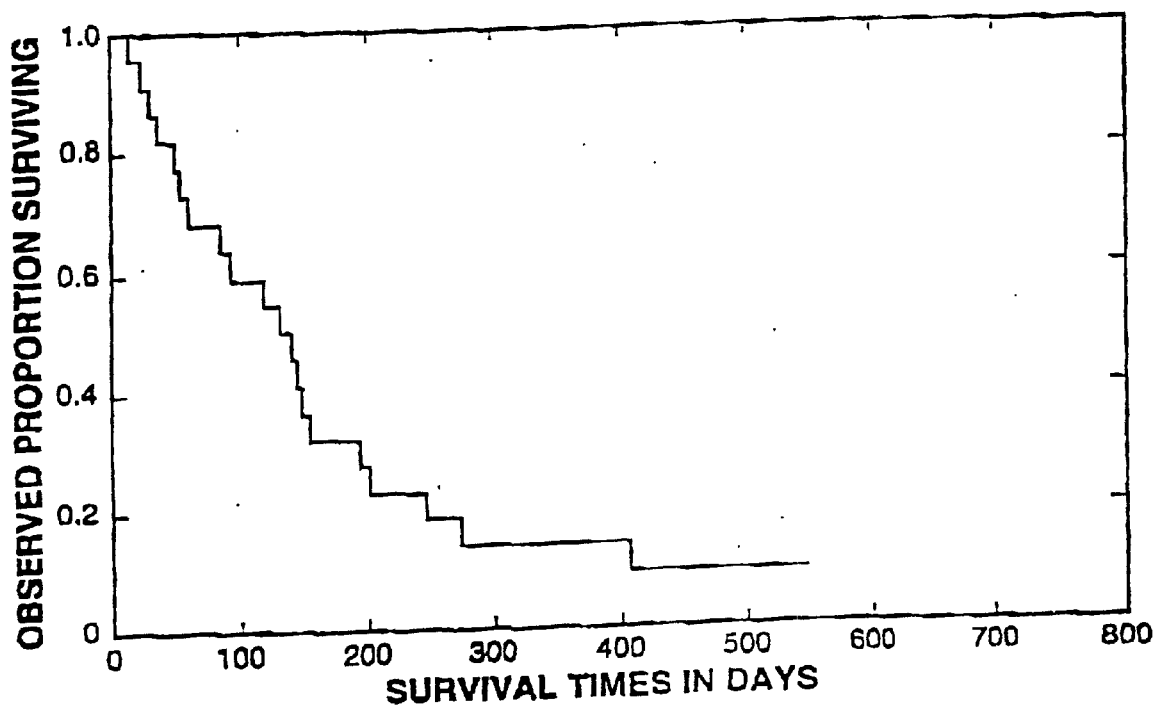
FIG. 7 is a graph showing survival taken from treatment of pancreatic cancer patients treated with the composition of the invention.

Survival curves representing the survival times from diagnosis and from treatment initiation are presented in FIGS. 6 and 7, respectively. For comparison, an historical survival curve for Gudjonsson (1987) has been superimposed in FIG. 6. Another example of a comparable historical survival curve may be found in Bakkevold, Petterson, Arnesjo and Espenhaug (1990).

The results of the survival analyses are summarized below:

| Survival | Patient Population | Mean Survival (days) | Standard Deviation | Median Survival (days) |
|---|---|---|---|---|
| From diagnosis | Protocol CO2-104 patients | 281 | 203 | 182 |
|  | Protocol CO2-104 evaluable patients | 304 | 157 | 219 |
| From treatment start | Protocol CO2-104 patients | 166 | 135 | 133 |
|  | Protocol CO2-104 evaluable patients | 220 | 132 | 146 |

The mean survival time for diagnosis was 281 days, as noted in FIG. 6. The median survival was 182 days (approximately 5 months). For comparison, Gudjonsson (1987) reported the mean survival of his 188 surgical patients as 208 days with a median survival of 120 days. The mean survival time from treatment start was 166 days (see FIG. 7). The median survival was 133 days (approximately 4 months and 1 week).

Survival times were also estimated among a subset of evaluable patients who had each received at least 13 injections. Fourteen of the 22 patients were evaluable. Among these patients, as noted in the previous table, the median survival from diagnosis was 219 days (approximately 7 months and 1 week). The median survival from treatment is start was 146 days (approximately 5 months).

The one year survival rate for evaluable patients (n=17) from the initiation of VIRULIZIN™ treatment was 18%, with a median survival of 5 months. The one-year survival rate from diagnosis was 35% with a median survival of 7.3 months. In a historical cohort of patients with similar disease, the one-year survival rate from diagnosis was 13.8% with a median survival of 120 days. The quality of life, pain and ECOG performance status remained constant or improved over 8 weeks of VIRULIZIN™ treatment for 57%, 71% and 66% of patients respectively for whom data were reported. Stable and declining CEA levels supported the clinical finding of stable disease.

EXAMPLE 20

This example illustrates clinical trials regarding treatment of malignant melanoma with Virulizin.

Advanced malignant melanoma was defined to include all stage III or IV patients and all loco-regional or distant relapses occurring after primary treatment. The standard treatment by which all other treatments are judged is DTIC (dacarbazine), which has a reported response rate of about 15%. The median response is 3–6 months, and carries with it severe nausea and vomiting, and a potentially lethal side effect of acute liver necrosis by thrombosis of the hepatic veins. This treatment fails to show any definitive survival advantages.

This study was conducted to determine the safety and efficacy of the composition of the invention and to determine its effect on survival and on quality of life, when used in patients with advanced malignant melanoma. The study, was a non-comparative, multicenter trial.

An initial dosing schedule of 7.5 ml injections of the composition of the invention intramuscularly 3 times per week was used. After no organ or marrow toxicity was observed, the loading schedule was increased to daily injections for 15 days, followed by maintenance of 3 injections per week. Subsequently the loading dose was increased to 30 days. Duration of treatment was 36 weeks and then reduced to 16 weeks, after which patients were given the option of entering a continuation protocol.

Thirty-three patients with advanced melanoma were included in the study population (17 females and 16 males), ranging in age from 17 to 85 years of age. Of the study population, 64% had been previously treated and 36% were untreated; 25 of the 33 patients were evaluable. The Karnofsky Performance Status (baseline) was in the range of 40–100%, median 80%. Eleven patients were alive at the end of the study period and five of these were under treatment.

A minor partial response was observed in 16/33 patients (48%). One patient had a reduction of 33% in the lungs, six patients had pain reductions and eight patients gained more than 1000 grams in weight for more than a month (Range 1000–2600 grams). A stable condition was observed in 19/33 patients (58%) (Range 60–170 days, median 77 days).

Figure 8:
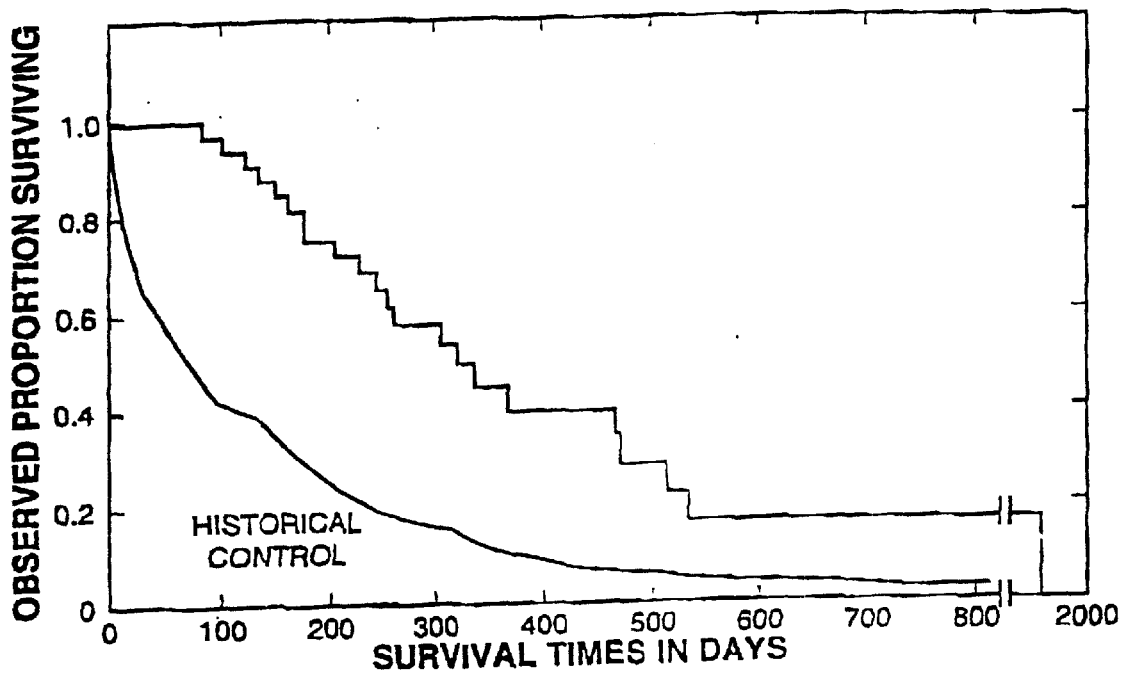
FIG. 8 is a graph showing survival of all melanoma patients treated with the composition of the invention.
Figure 9:
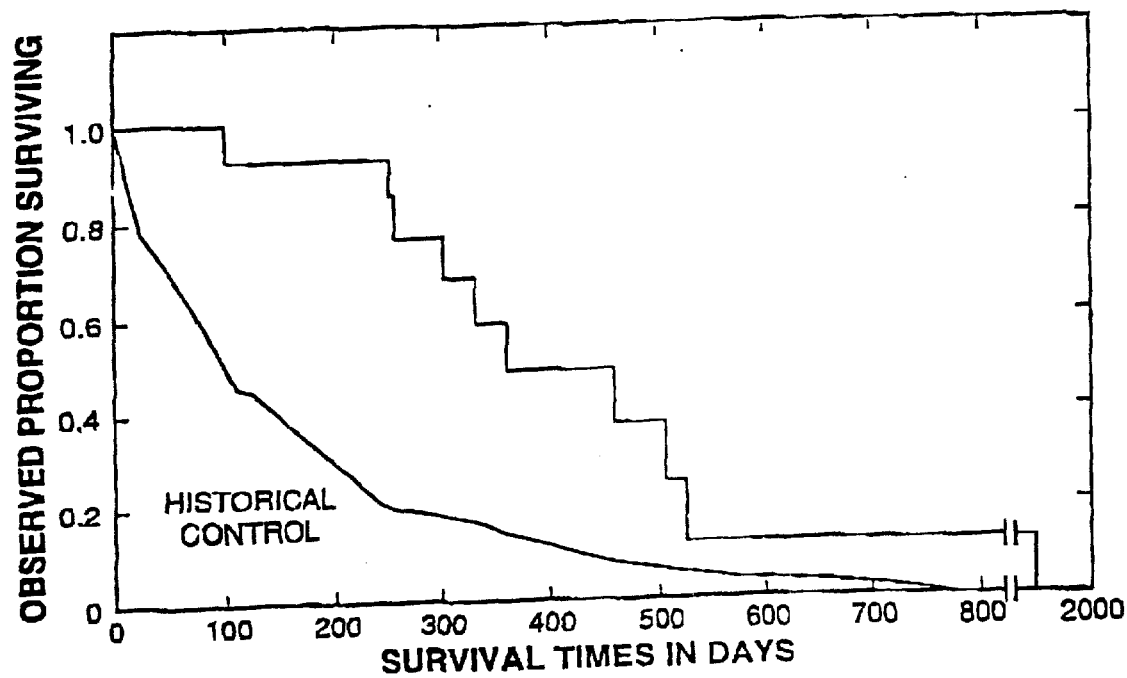
FIG. 9 is a graph showing survival of melanoma patients with two or more tumor sites treated with the composition of the invention.
Figure 10:
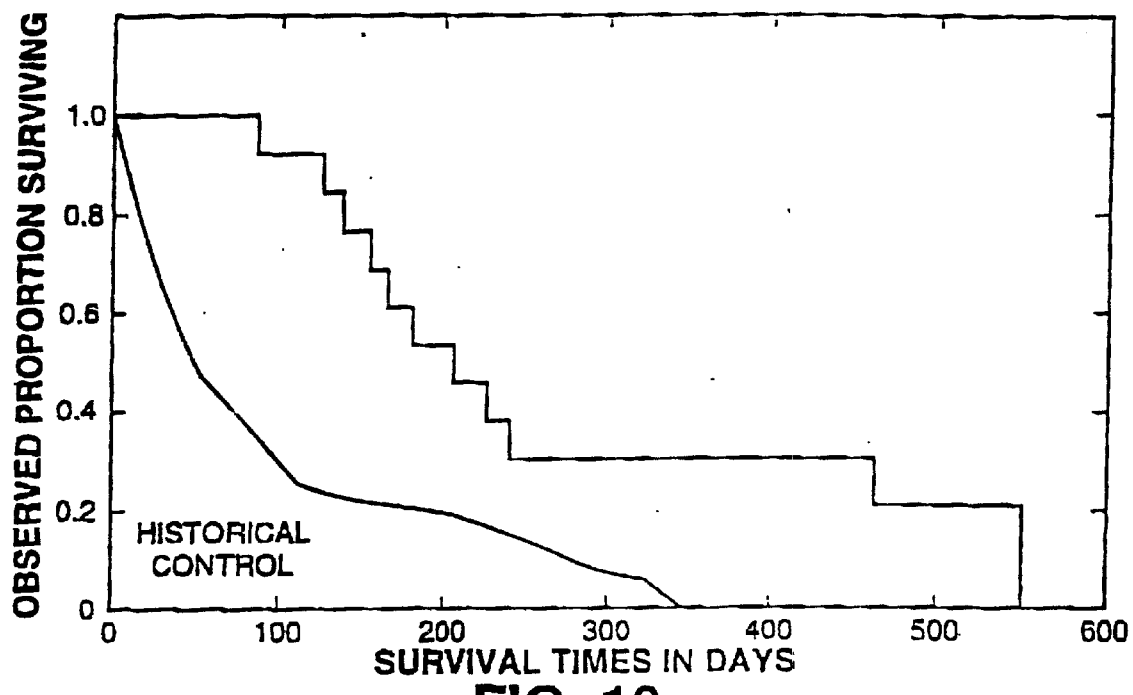
FIG. 10 is a graph showing survival of melanoma patients with three or more tumor sites treated with the composition of the invention.

FIGS. 8, 9 and 10 show the survival of patients treated with the composition of the invention compared to historical controls, measured as survival from diagnosis of metastases/recurrence in days. The solid line represents the survival curve for patients treated with the composition of the invention and the broken line represents the historical survival curve (Balch et al., *Cutaneous Melanoma,* 2nd. ed. 1992, Chps. 14 and 39, pp. 165–187 & 499–508, Lippincott Co., Philadelphia, Pa.). The survival of all patients treated with the composition of the invention, including patients with one to over three tumor sites, is shown in FIG. 8. Survival of patients with two tumor sites and with three or more tumor sites is shown in FIGS. 9 and 10, respectively.

The group of all patients treated with the composition of the invention had a 39% survival (Kaplan-Meier estimation) at one year. The survival rate at one year for all advanced malignant melanoma (AMM) patients is approximately 11% in historical controls (matched by number of tumor sites). The group had a median survival of 315 days compared to the historical median of 89 days.

For patients with two tumor sites, the one-year survival was 49% in the patients treated with the composition of the invention, as compared with 13% in historical controls. This group had a median survival of 360 days compared to the historical median of 120 days. With three or more tumor sites the one year survival was 31% in the patients treated with the composition of the invention, as compared with 0% in historical controls. The group with three or more tumors had a median survival of 205 days compared to the historical median of 60 days.

Quality of life was assessed by weight gain, performance status (Karnofsky), Quality of Life Index (Spitzer) and pain scale (Linear Analogue). Weight gain over time is shown in the following table.

| Number of patients/evaluable | 1st month | 2nd month | 3rd month | 4th month | 5th month | 6th month |
|---|---|---|---|---|---|---|
|  | 11/25 | 12/25 | 4/25 | 4/25 | 1/25 | 1/25 |
| Percent | 44% | 48% | 16% | 16% | 4% | 4% |
| Range (gr) | 100–2400 | 200–6000 | 100–1000 | 100–2000 | — | — |
| Average (gr) | 900 | 1480 | 525 | 775 | 100 | 2000 |

The Karnofsky and Spitzer scales are both subjective and were found to agree approximately in each individual. Fifteen patients reported no change in these parameters. Four patients showed fluctuations which later returned to previous levels. One patient had a decrease (from 40–20%).

The results of pain evaluation for six patients showed that by week 4 the pain dropped from 5 (worst possible) to 2 (moderate) or 0 (no pain). One patient had a drop in pain from 3 to 0. One patient with hepatic metastasis had pain reduction to 0 and stabilization for 11 months. Nine patients who entered the study with 0 pain maintained that level throughout the study. Five patients had a moderate (2 unit) increase in pain. Three patients had transient pain increases (1 to 2 units) during the second or third month.

Out of 1734 injections administered to 33 patients, 21 patients had no adverse drug reactions. Fourteen adverse drug reactions were reported in 12 patients. The adverse drug reactions usually occurred at weeks 4 or 8 and were mild to transient, and most frequently were a low grade fever.

The difference in survival between the historical groups and the protocol groups treated with the composition of the invention suggests a survival benefit for patients treated with the composition of the invention. The cancer seemed to stabilize in 19 patients. All patients treated for AMM were included in the survival data. Also included were 21 previously treated patients (many clinical trials require untreated patients, because of the poor prognosis of failed previous treatments). The tumor burden in this population was high (82% had more than one metastatic site).

The survival and quality of life data suggest that most patients received some benefit from the treatment. Eleven patients were still alive at the end of the study period and of those 11, five continued treatment.

Preliminary analysis on 33 patients demonstrated a one-year survival rate (from diagnosis of recurrence) of 39%. Upon conclusion of the study, final data were available for 45 patients. Forty-one of these patients had distant metastases. The one-year survival rate from diagnosis of distant metastases for these patients was 61%, with a median survival of 529 days (17.6 months). This can be compared to a survival rate of 13% (median 92 days) from historical data. The one-year survival rate from initiation of VIRULIZIN™ for all patients was 22%, with a median survival of 200 days (6.7 months).

The quality of life, pain and ECOG performance status showed no change or an improvement over the first 8 weeks of treatment in 63%, 93%, and 70% of patients respectively for whom data were available. In addition, pre- and post-VIRULIZIN™ tumor pathology demonstrated an unusual pattern of tumor cell necrosis, fibrosis, and vascular thrombosis consistent with TNF-α mediated effects.

EXAMPLE 21

This example illustrates a pathology protocol directed to malignant melanoma.

The following is a report of a 73 year old female with progressive malignant melanoma of the hard palate and gums. FIG. 15 shows two views of malignant melanoma as seen under the microscope. In FIG. 15a, looking from top to bottom, one can see the epithelial layer with accompanying keratin, beneath which the malignant cells start to became more apparent. These melanoma cells can be seen to be rounded or oval, with an abundant eosinophilic cytoplasm, and pleomorphic hyperchromatic nuclei. These cells have substituted the normal submucosal tissue. The blood vessels which are seen appear normal, and there is a paucity of any kind of inflammatory/immune response as would be represented by the presence of leukocytes (poly-morphonuclear and mononuclear cells). This is an example of tumor tissue which is thriving, i.e. the tumoral architecture is intact.

In FIG. 15b a tumor tissue sample is shown from the same patient, who had been treated with the composition for two months. Starting from top to bottom, one can see that the continuity of the epithelium has been disrupted by a necrotic process. This necrosis, while common in the center of any tumor that has reached a critical mass, is rarely seen on the periphery, especially in malignant melanoma, and is a sign that the host's immune response is mounting an attack against the tumor. Throughout the photo are a massive number of cells different from the original tumor cells. These are the immune cells, including neutrophils, lymphocytes, macrophages, which have orchestrated the disruption of the typical tumoral architecture. The blood vessel walls have become densely infiltrated with a large number of host immune cells (arrow). This cellular infiltrate subsequently will cause the destruction of the blood vessel, which in turn prevents the tumor from receiving its supply of nutrients and oxygen (ischemic necrosis). This immune response which contributed to the tumoral disruption seen in this patient's tissue slide is consistent with reported changes known to be brought about by TNF (tumor necrosis factor) and with the results of the work described in the previous examples.

The immune response demonstrated in the after treatment with the composition slide (FIG. 15b) strongly links the in vitro TNF immune modulation by the composition with known in vivo anti-tumoral TNF effects.

EXAMPLE 22

This example illustrates the effects of Virulizin™ on tumoricidal function of peripheral blood monocytes of cancer patients.

Peripheral blood monocytes from venous blood from cancer patients were obtained, processed, and assayed for tumoricidal activity against Chang hepatoma cells according to the procedure of Example 9. The results are presented in the following table, wherein the following abbreviations are used:

"ENT CA" is Ear, nose, & throat carcinoma;
"KS/HIV" is Kaposi's sarcoma in patients infected with Human Immunodeficiency Virus;
"Ovarian CA" is ovarian carcinoma;
"Lung CA" is lung carcinoma;
"Endo CA" is endometrial carcinoma of uterus;
"CML" is chronic myelogenous leukemia;

Terms used in the table include: "Diagnosis," which refers to the type of cancer that the patient had. The total number of patients that provided monocytes for testing is noted as a "# tested." The number of patients whose monocytes showed the ability to be stimulated by VIRULIZIN™ over the total number of patients tested, is termed "# stimulated/total (Virulizin™)." The number of patients whose monocytes showed ability to be stimulated by a combination of 100 Units/ml of interferon-gamma (IFN-γ) and 2 ng/ml of lipopolysaccharide (LPS) of *Escherichia coli* origin over the total number of patients tested is termed "# stimulated/total (IFN/LPS)." With respect to stimulated/total (IFN/LPS or Virulizin™), stimulation is defined as an increase of greater than 50% above the tumoricidal values obtained by culture with medium alone. "Batches/stimulation" recites the batch or lot number of the Virulizin used followed by the number of tests that showed stimulation over the total number of tests with that batch/lot in parentheses.

EFFECTS OF VIRULIZIN ON TUMORICIDAL FUNCTION OF PERIPHERAL BLOOD MONOCYTES OF CANCER PATIENTS

| Diagnosis | # Tested | # Stimulated/Total (Virulizin) | # Stimulated/Total (IFN/LPS) | Batches/Stimulation |
|---|---|---|---|---|
| ENT CA | 10 | 8/10 | 5/10 | 222 (3/4) |
|  |  |  |  | 219 (2/3) |
|  |  |  |  | 216 (1/2) |
|  |  |  |  | 233 (3/3) |
|  |  |  |  | 238 (1/2) |
| KS/HIV | 9 | 6/9 | 2/9 | 222 (4/7) |
|  |  |  |  | 238 (2/2) |
| Ovarian CA | 3 | 2/3 | 2/3 | 222 (2/2) |
|  |  |  |  | 216 (0/1) |
| Lung CA | 2 | 2/2 | 1/2 | 222 (2/2) |
| Endo CA | 1 | 1/1 | 1/1 | 222 (1/1) |
| CML | 1 | 1/1 | 0/1 | 233 (1/1) |
|  |  |  |  | 238 (1/1) |
| TOTALS: | 26 | 20/26 (77%) | 11/26 (42%) |  |

These results show that the tumoricidal activity elicited by VIRULIZIN™ in cancer patients' monocytes was equal to or greater than the activity produced in response to a combination of conventional macrophage activators (IFN-α and LPS). VIRULIZIN™ can also stimulate tumoricidal function in macrophages obtained from HIV patients with Kaposi's sarcoma, even at very late stages of the disease. Thus, the action of VIRULIZIN™ appears to be independent of collaboration with other immune cell types, including helper T lymphocytes.

EXAMPLE 23

This example illustrates the effects of Virulizin™ on tumor-associated macrophages from cancer patients.

Alveolar macrophages from 11 patients with non-small cell lung cancer were obtained by bronchoalveolar lavage and assayed for tumoricidal activity against Chang hepatoma cells by the procedure described in Example 9.

Peritoneal macrophages were obtained from 7 patients with gynecological cancer (2 endometrial, 3 ovarian, and 2 cervical) and assayed for tumoricidal activity against Chang hepatoma cells by the aforementioned procedure.

The results are displayed in the following table, wherein the abbreviations and terms used are defined as recited in Example 22.

EFFECTS OF VIRULIZIN ON TUMOR-ASSOCIATED MACROPHAGES FROM CANCER PATIENTS

| # Tested | # Stimulated/Total (Virulizin) | # Stimulated/Total (IFN/LPS) | Batches/ Stimulation |
|---|---|---|---|
| Alveolar Macrophages in Non-Small Cell Lung Cancer | | | |
| 11 | 5/11 | 5/11 | 222 (2/7) |
| | | | 219 (1/4) |
| | | | 216 (1/4) |
| | | | 233 (2/3) |
| | | | 238 (3/4) |
| Peritoneal Macrophages in Gynecological Cases | | | |
| 7 | 7/7 | 6/7 | 222 (6/6) |
| | | | 219 (2/2) |
| | | | 216 (0/1) |

These results indicate that VIRULIZIN™ can stimulate both the peripheral blood monocytes and regional, tumor-associated macrophages from cancer patients to express significant tumor-killing activity. This result was observed in peritoneal macrophages from women with gynecological malignancies and alveolar macrophages from patients with lung cancer. From these results, it is believed that VIRULIZIN™ can also stimulate the macrophages of cancer patients that are unresponsive to stimulation with conventional activators such as gamma interferon plus endotoxin.

EXAMPLE 24

This example illustrates the effect of Virulizin™ on the development of tumoricidal function against autologous tumor cells in monocytes from cancer patients.

Peripheral blood monocytes were obtained and assayed for tumoricidal activity against autologous tumor cells, using the methods described in Example 9. Thus, monocytes from a patient with an ear/nose/throat carcinoma, for example, were assayed for tumoricidal activity against that patients own tumor cells. Analogous tests using ovarian and endometrial carcinoma and chronic myelogenous leukemia cells were also accomplished. The results are displayed in the following table, wherein the abbreviations and terms used are as recited in Example 22. The medium used is Roswell Park Memorial Institute [RPMI] 1640 media supplemented with 10% heat inactivated fetal bovine serum, 50 Units/ml penicillin, and 50 ug/ml streptomycin.

EFFECT OF VIRULIZIN ON THE DEVELOPMENT OF TUMORICIDAL FUNCTION AGAINST AUTOLOGOUS TUMOR CELLS IN MONOCYTES FROM CANCER PATIENTS

| | | % Cytotoxicity | | |
|---|---|---|---|---|
| Diagnosis | Batch # | Medium | IFN/LPS | Virulizin |
| ENT CA | 222 | 14.9 | 11.5 | 10.9 |
| ENT CA | 222 | 11.6 | 12.0 | 24.9 |

-continued

EFFECT OF VIRULIZIN ON THE DEVELOPMENT OF TUMORICIDAL FUNCTION AGAINST AUTOLOGOUS TUMOR CELLS IN MONOCYTES FROM CANCER PATIENTS

| | | % Cytotoxicity | | |
|---|---|---|---|---|
| Diagnosis | Batch # | Medium | IFN/LPS | Virulizin |
| ENT CA | 222 | 13.7 | 10.5 | 25.7 |
| ENT CA | 222 | 17.7 | 11.4 | 35.2 |
| ENT CA | 240 | 3.2 | 15.6 | 15.7 |
| Ovarian CA | 222 | 0.0 | 17.2 | 14.0 |
| Ovarian CA | 233 | 2.9 | 16.1 | 12.3 |
| Ovarian CA | 238 | 2.9 | 16.1 | 15.0 |
| Ovarian CA | 239 | 2.9 | 16.1 | 13.0 |
| Ovarian CA | 240 | 2.9 | 16.1 | 9.2 |
| Endo CA | 222 | 26.7 | 44.5 | 35.5 |
| Endo CA | 222 | 1.2 | 4.5 | 9.2 |
| CML | 233 | 10.7 | 15.2 | 22.6 |
| CML | 238 | 10.7 | 15.2 | 17.0 |
| # Stimulated/Total | | | 5/10 (50%) | 9/10 (90%) |

These results indicate that VIRULIZIN™ can stimulate tumoricidal activity in macrophages of cancer patients against autologous tumor cells prepared from surgical biopsies from cancer patients. From these results, it is believed that VIRULIZIN™ can stimulate the macrophages of cancer patients that are unresponsive to stimulation with conventional activators such as gamma interferon plus endotoxin.

EXAMPLE 24

This example illustrates the effect of cytokine-specific antibodies on the development of tumoricidal function in Virulizin-stimulated monocytes.

Peripheral blood monocytes from a patient with lung cancer and from a patient with chronic myelogenous leukemia (CML) were obtained and assayed for tumoricidal activity against Chang hepatoma cells according to the method of Example 9. VIRULIZIN™ alone was used to test for stimulation of the monocytes as well as VIRULIZIN™ plus anti-IL1α, or anti-IL1β, or anti-TNFα, or isotype control antibody. The amount of antibody used was a saturating amount for these assay conditions as determined by titration experiments in accordance with standard methods.

The results are displayed in the following table, wherein the abbreviations used are as recited in example 23. In addition, "anti-IL1α" is antibody to interleukin 1 alpha; "anti-IL1β" is antibody to interleukin 1 beta; "anti-TNFα" is antibody to tumor necrosis factor alpha; and "isotype control" is antibody to an epitope unrelated to the above cytokines.

Effect of Cytokine-Specific Antibodies on the Development of Tumoricidal Function in Virulizin-Stimulated Monocytes

| Culture | % Specific Cytotoxicity |
|---|---|
| Experiment 1 (Lung Cancer Patient, Chang Hepatoma) | |
| λ-IFN/LPS | 8.1 |
| Virulizin (219) | 10.6 |
| Virulizin + anti-IL1α | 13.9 |

-continued

Effect of Cytokine-Specific Antibodies on the Development
of Tumoricidal Function in Virulizin-Stimulated Monocytes

| Culture | % Specific Cytotoxicity |
|---|---|
| Virulizin + anti-IL1β | 10.1 |
| Virulizin + anti-TNFα | 5.9 |
| Virulizin + isotype control | 9.3 |
| Experiment 2 (CML Patient, Chang Hepatoma) | |
| Medium | 5.7 |
| Virulizin (216) | 11.0 |
| Virulizin + anti-IL1α | 9.2 |
| Virulizin + anti-IL1β | 9.1 |
| Virulizin + anti-TNFα | 2.8 |

The results indicate that antibodies against tumor necrosis factor alpha inhibit the tumoricidal function elicited by VIRULIZIN™. Antibodies against either interleukin 1 alpha or interleukin 1 beta failed to reduce the tumoricidal function of VIRULIZIN™ stimulated monocytes. The results are consistent with the conclusions that the macrophage tumoricidal function that develops in response to VIRULIZIN™ is associated with the production of tumor necrosis factor-alpha (TNFα) by the monocytes.

EXAMPLE 25

The example illustrates the effect of cytotoxic therapy on the development of tumoricidal function in Virulizin-stimulated peripheral blood monocytes.

Peripheral blood monocytes were obtained from cancer patients at the end of their first course of remission induction chemotherapy and assayed for tumoricidal activity against Chang hepatoma cells using the methods of Example 9.

The results are disclosed in the following table, wherein the abbreviations used as disclosed in Example 24. In addition, "Pt" is cis-platinum; "5-FU" is 5 fluorouracil; "RT" is radiotherapy; and "Ara C" is cytosine arabinoside. The term "Diagnosis" is the type of cancer the patient had. When the phrase "recurrent" is listed here, the cancer has recurred, otherwise the cancer was newly diagnosed. The term "Therapy" is the regimen of cancer chemo/radiotherapy that the patient was undergoing.

EFFECT OF CYTOTOXIC THERAPY ON
THE DEVELOPMENT OF TUMORICIDAL FUNCTION IN
VIRULIZIN-STIMULATED PERIPHERAL
BLOOD MONOCYTES

| | | % Cytotoxicity | | |
|---|---|---|---|---|
| Diagnosis | Therapy | Medium | IFN/LPS | Virulizin |
| ENT CA | Pt/5-FU | 6.8 | 11.7 | 10.2 |
| ENT CA Recurrent | RT/Pt/5-FU | 5.8 | 10.1 | 24.2 |
| ENT CA | RT | 28.8 | 31.2 | 44.3 |
| ENT CA Recurrent | RT/Pt/5-FU | 11.6 | 12.0 | 24.9 |
| ENT CA Recurrent | RT/Pt/5-FU | 46.0 | 56.8 | 80.1 |
| ENT CA Recurrent | RT | 11.6 | 22.8 | 27.6 |
| CML | Ara C/Idarubicin | 13.5 | 10.7 | 35.6 |
| # Stimulated/Total | | | 3/7 (43%) | 6/7 (86%) |

The results indicate that VIRULIZIN™ stimulates tumoricidal function in macrophages obtained from cancer patients who are undergoing cytotoxic therapy. Accordingly, it is believed that VIRULIZIN™ interacts favorably with other therapeutic modalities. Of note is the fact that VIRULIZIN™ was more effective in stimulating tumoricidal function than conventional activators such as gamma interferon plus endotoxin.

EXAMPLE 26

This example illustrates the effect of Virulizin on macrophage cytotoxicity in patients with endometriosis.

Peripheral blood monocytes and peritoneal macrophages from endometriosis patients were obtained in as in Example 9 and tested for tumoricidal activity against Chang hepatoma cells and for cytotoxicity against autologous endometrial cells prepared from uterine biopsies.

The results are displayed in the following table, wherein the abbreviations and terms used are as in Example 25. In addition, "Stage" refers to endometriosis staging based on the RAFS (Revised American Fertility Society) classification system.

EFFECT OF VIRULIZIN ON MACROPHAGE CYTOTOXICITY IN
PATIENTS WITH ENDOMETRIOSIS

| Stage | Batch # | Medium | IFN/LPS | Virulizin | Effect |
|---|---|---|---|---|---|
| III | 219 | 9.5 | ND | 21.3 | Stimulation |
| II | 219 | 1.2 | 4.5 | 9.2 | Stimulation |
| IV | 233 | 11.5 | 15.3 | 26.9 | Stimulation |
| IV | 238 | 11.5 | 15.3 | 37.3 | Stimulation |
| III | 233 | 7.4 | 11.1 | 14.0 | Stimulation |
| III | 238 | 7.4 | 11.1 | 16.4 | Stimulation |

The results indicate that VIRULIZIN™ stimulates peripheral blood monocytes and peritoneal macrophages from endometriosis patients to kill endometrial cells prepared from uterine biopsies. Accordingly, the composition of the present invention may provide a treatment for endometriosis.

EXAMPLE 27

This example illustrates the results of preliminary testing of Virulizin™ batches.

Peripheral blood monocytes from venous blood were obtained, processed, and assayed for tumoricidal activity against Chang hepatoma cells by the procedure described in Example 9. The Virulizin™ was prepared according to Example 1.

The results are displayed in the following table, wherein the abbreviations and terms used are as in Example 26. In addition, "Donor" is disease status of patients from whom peripheral blood monocytes were obtained. "Normal" means the patient had no disease. "ENT CA" means the patient had head and neck (ear/nose/throat) cancer.

Preliminary Tests of Virulizin Batches 247, 248, and 249

| Donor | Batch # | Medium | IFN/LPS | Virulizin |
|---|---|---|---|---|
| Normal | 247 | 11.7 | 21.0 | 31.1 |
| Normal | 248 | 11.7 | 21.0 | 19.6 |
| Normal | 249 | 11.7 | 21.0 | 29.1 |
| ENT CA | 247 | 11.6 | 22.8 | 27.6 |
| ENT CA | 248 | 11.6 | 22.8 | 26.7 |
| ENT CA | 243 | 9.3 | 15.3 | 29.6 |
| ENT CA | 247 | 9.3 | 15.3 | 17.9 |
| ENT CA | 248 | 9.3 | 15.3 | 11.4 |
| ENT CA | 249 | 9.3 | 15.3 | 26.2 |

The results indicate that the tumoricidal activity elicited by VIRULIZIN™ in normal and cancer patients' monocytes was equal to or greater than the activity produced in response to a combination of conventional macrophages phage activators (IFN-γ and LPS).

EXAMPLE 28

This example illustrates the isolation of active fractions.

A 300 ml sample of the composition was evaporated to dryness on a rotovap in which the temperature of the bath did not exceed 40° C. In order to ensure that the solution remained basic during the evaporation, 5 drops of a concentrated ammonium hydroxide solution was added every half hour to the composition until the evaporation was complete. The resulting residue had a weight of 11.6 g.

20 ml of a 10% concentrated ammonium hydroxide in methanol solution was then added to 2 g of the above residue. The insoluble material was filtered off and the filtrate was chromatographed through 101.93 g of 60 Å flash silica gel in a column with dimensions of 5 cm×12.5 cm. The solvent system used was 10% concentrated ammonium hydroxide in methanol solution. The column was run at a pressure of 10 p.s.i. and a flow rate of 11 ml/min. After 100 ml of solvent had passed through the column, twelve 20 ml. fractions were collected. The collection of these fractions correlated to the appearance of an off-white band that was quickly moving down the column.

Thin layer chromatography (TLC) of these fractions was run on silica gel plates in a 10% concentrated ammonium hydroxide solution in methanol and visualized with a ninhydrin spray. Fractions having similar TLC profiles were combined, resulting in the following fraction combinations, which were dried on a rotovap:

| Fractions | Volume Through Column to Obtain Fraction | Yield (g) |
|---|---|---|
| 1–4 | 100–180 | 0 |
| 5–6 | 180–220 | 0.1175 |
| 7–8 | 220–260 | 0.1969 |
| 9–10 | 260–300 | 0.0151 |
| 11–12 | 300–340 | 0.0053 |

Fractions 5–6, 7–8 and 9–10 had a positive reaction with ninhydrin at an $R_f$ value of 0.81.

Fractions 5–6 and 9–10 were tested in vitro for TNF stimulation (in accordance with Example 9). The results are shown below:

| Fraction | Activity |
|---|---|
| 5–6 | 50 pg/mg |
| 9–10 | 1814 pg/mg |

Thus, fraction 9–10 was an extremely active TNF stimulator.

Samples of Fraction 5–6 were analyzed by Electron Impact Mass Spectroscopy (EI MS) and Electrospray Mass Spectroscopy to identify specific compounds likely to be present in the fraction. The Electrospray MS was performed on a Perkin-Elmer Sciex API-III spectrometer, using 5% acetic acid in water as the solute. In some instances, methanol was added to aid dissolution. The EI MS using a direct insertion probe was performed on a VG Analytical model ZAB-SE spectrometer using glycerol as a matrix, and using a DCI probe on a Kratos Analytical Profile Mass Spectrometer.

A review of the resultant spectra indicated that the following compounds were likely present in Fraction 5–6: phosphocholine, taurocholic acid, choline-stearic acid diglyceride, stearic acid, stearic acid diglyceride, palmitic acid-stearic acid diglyceride, and a sphingosineoleic acid conjugate.

EXAMPLE 29

This example illustrates an expanded procedure to isolate active fractions.

Example 28 was repeated on a larger scale, as follows. 10 ml of a concentrated ammonium hydroxide solution was added to 900 ml of the composition and the resulting solution evaporated to dryness on a rotovap in which the temperature of the bath did not exceed 40° C. In order to ensure that the solution remained basic during the evaporation, 5 drops of a concentrated ammonium hydroxide solution was added every half hour to the composition until the evaporation was complete, leaving a residue.

150 ml of a 10% concentrated ammonium hydroxide in methanol solution was then added to the total residue. The solution was sonicated for 15 min. and the insoluble material was filtered off. The filtrate was chromatographed through 1695 g of 60 Å flash silica gel in a column with dimensions of 30cm×12 cm. The solvent system used was 10% concentrated ammonium hydroxide in methanol solution. The column was run at a pressure of 6 p.s.i. and a flow rate of 30 ml./min. The results of the column are summarized in the table below.

| Fraction # | Volume of each fraction (ml.) | Observations |
|---|---|---|
| 1 | 550 | clear, yellowish |
| 2 | 450 | clear, yellowish |
| 3 | 400 | clear, yellowish |
| 4 | 150 | clear, yellowish |
| 5 | 100 | clear, yellowish |
| 6–7 | 75 | clear, yellowish |
| 8–13 | 50 | clear, yellowish |
| 14 | 50 | tan colored solution begins to elute |
| 15–35 | 50 | tan colored solution |
| 36–40 | 50 | clear, yellowish |

TLC was run on silica gel plates in a 10% concentration ammonium hydroxide solution and visualized with a ninhydrin spray. Fractions having similar TLC profiles were combined, resulting in the following fraction combinations, which were dried on a rotovap:

| Fraction # | Volume Through Column to Obtain Fraction | Yield (g) | Comments |
|---|---|---|---|
| 3 | 1000–1400 | 0.0504 | white powdery solid |
| 4–5 | 1400–1650 | 0.0855 | white powdery solid |
| 6–8 | 1650–1850 | 0.1555 | white powdery solid |
| 9–12 | 1850–2050 | 0.3014 | white powdery solid |
| 13–14 | 2050–2150 | 0.3595 | white powdery solid |
| 15–16 | 2150–2250 | 0.6914 | slight brown color - solid is tacky |
| 17–18 | 2250–2350 | 1.0284 | tan color - solid is clumpy |
| 19 | 2350–2400 | 0.3432 | tan color - solid is clumpy |

-continued

| Fraction # | Volume Through Column to Obtain Fraction | Yield (g) | Comments |
|---|---|---|---|
| 20–23 | 2400–2600 | 1.1531 | brown color - solid is clumpy |
| 24–30 | 2600–2950 | 0.8517 | brown color - solid is clumpy |
| 31–34 | 2950–3150 | 0.0813 | brown oil |

All fraction combinations from 15–16 through Fraction 31–34 had a positive reaction with ninhydrin at an $R_f$ value of 0.87, a value very similar to the $R_f$ value for the active fractions of Example 28. Fractions 24–30 and 31–34 had an additional positive reaction with ninhydrin at an $R_f$ value of 0.85.

Fractions 4–5, 15–16 and 17–18 were tested in vitro for TNF stimulation (in accordance with Example 9), resulting in no TNF stimulation activity. Elemental analysis of the above fractions showed them to be high in $NH_4Cl$, which is known to inhibit TNF production.

Samples of fractions 15–16 and 24–30 were dialyzed and then analyzed by mass spectroscopy, using the methods described in Example 28. Undialyzed samples from fractions 17–18 and 24–30 were also analyzed. A review of the resultant spectra indicated that the following compounds were likely present: glycocholic acid, a trihexosamine trimer, and taurocholic acid (Fraction 15–16); stearic acid, and a hexosamine dimer; and glycocholic acid (Fraction 24–30).

EXAMPLE 30

This example illustrates the application of further methods to fractionate and analyze the active components of the inventive composition.

Having identified that TNF, IL-1β and GM-CSF releasing activity can be precipitated, in part, by 80% acetonitrile and that much of the releasing activity elutes early from $C_{18}$ RP-HPLC, the physicochemical properties of the precipitate fraction have been studied and compared to the whole composition and supernatant fraction of the composition.

Figure 11:
FIG. 11 is an SDS gel of the composition of the invention.

FIG. 11 shows an SDS gel electrophoresis of whole composition and precipitates and supernatants of the composition. In all three instances, the composition runs near the SDS front, indicating a low molecular weight. The smallest standard used was 14,400 daltons.

The molecular size of the composition was also examined by determining its time of elution from a molecular sieve HPLC column. The elution times of whole composition, precipitate and supernatant compared to standards. All three eluted later than insulin, which eluted at 24.5 min. Once again, physicochemical analysis indicates a mol. wt. less than 2,400 daltons.

Figure 13:
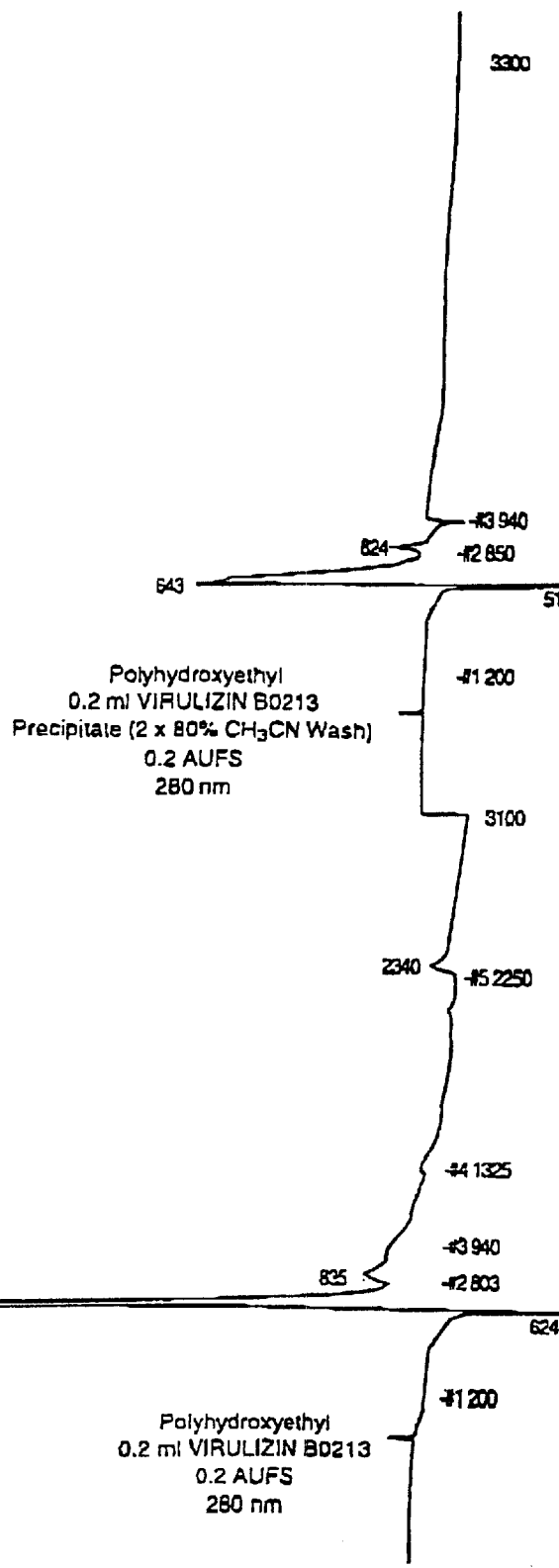
FIG. 13 shows the elution of a precipitate of the composition of the invention on hydrophilic HPLC.

The TNF-releasing component elutes early. Thus a column with the opposite effect was chosen, a hydrophilic column in the presence of organic solvents. The ideal eluting conditions for the polyhydroxyethyl column is 80% acetonitrile. However, as indicated in the prior Example, some of the substances in the preparation precipitated at this concentration. Consequently, the composition was analyzed at a low concentration of acetonitrile where the column functions mostly as a molecular sieve column. FIGS. 12 and 13 show the profile of whole supernatant and precipitate. The front sheet summarizes the elution time for the different peaks. The elution times indicate the active component of the composition has a low molecular weight.

The composition and its precipitate and supernatant were separated by ion-exchange HPLC. Both by AX300 (anion exchange) chromatography and by CMX 300 (cation exchange) chromatography, there was no significant separation of components. Hydrophobic reverse phase chromatography did not separate the peaks.

In another series of experiments, 10 ml of VIRULIZIN™ was loaded onto an anion exchange chromatography column (Bio-Rad AG-1, hydroxide form, total resin wet volume was 10 ml, equilibrated with Millipore deionized water). The volume of resin was calculated to be sufficient for the binding of all the anions present in the extract. The unbound fraction was collected and reloaded onto the column in order to maximize the binding to the resin. The unbound fraction from this second passage was collected and saved. Any unbound material remaining on the column's void volume was removed by washing with deionized water (2×20 ml). Bound molecules were eluted with a step gradient of ammonium bicarbonate, 20 ml/step. Free ammonium bicarbonate was removed by lyophilization. Samples from all the fractions were tested for TNF-releasing activity in the monocyte/macrophage activation assay. TNF-releasing activity was not found in the unbound fraction (effluent), but the majority was found in the eluate eluted with 0.2 M ammonium bicarbonate. These results indicate that the active components are polar, anionic, acidic in nature.

Samples from all the fractions were analyzed for TNF stimulation activity, in accordance with the procedures of Example 2. The results are shown below:

| Sample | TNFα release-inducing activity-LPS (pg/ml) |
|---|---|
| 0 M | −496 |
| 0.1 M | −156 |
| 0.2 M | 1638 |
| 0.3 M | −36 |
| 0.4 M | 256 |
| 0.5 M | −27 |
| 0.6 M | −175 |
| 1.0 M | −246 |
| 1.5 M | −346 |
| VIRULIZIN ™ control | 1961 |

The results from the activity assays show that TNF production stimulation was found in the 0.2 M and 0.4 M fractions.

The composition was subjected to dialysis and drying of the dialysate, as follows: 100 ml of the composition was placed inside a Spectra/Por® CE membrane tubing which had a molecular weight cut off of 100. The ends of the tubing were sealed with clips and the tubing was placed into a stirred bath of 10 L of distilled water. The dialysis was monitored daily by removing 1 ml. of solution from the dialysis tubing and adding 3–4 drops of a 1/10 N silver nitrate solution. The presence of chloride indicated that the dialysis was not complete. If the dialysis was not complete the bath was replaced with fresh distilled water. Dialysis completion occurred after 3–4 days. After dialysis was complete, the dialyzed material was dried on a rotovap to yield an average of 0.3 mg of solid per ml of original volume.

A sample of the solid material was then dissolved in HPLC grade water, and TLC was run on silica gel plates in a 10% concentrated ammonium hydroxide solution in methanol, and visualized with a ninhydrin spray. A positive reaction with ninhydrin was obtained at an $R_f$ value of 0.83.

A sample of the solid material was also analyzed by mass spectroscopy, using the methods described in Example 28. A review of the resultant spectra indicated that the following compounds were likely present: a sphingosineoleic acid conjugate, diacetyl sialic acid, a fucose-hexosamine dimer, deoxyglycocholic acid, taurocholic acid, a sialic acid-fucose dimer, and a di(fucose)hexosamine trimer.

EXAMPLE 31

This example will illustrate the use of Reverse Phase-HPLC (RP-HPLC) to analyze the inventive composition.

Samples were lyophilized and then reconstituted in 0.1% trifluoroacetic acid (TFA) in water (buffer A) and subsequently run in the following columns and conditions:

| | |
|---|---|
| Column: | WP60009-C18 column (W-Pore C18, 250 × 4.6 mm, Phenomenex, California) in row with prime-sphere HC-C18 column (250 × 4.6 mm, Phenomenex, California) |
| Eluents: | Buffer A:0.1% TFA in $H_2O$ |
| | Buffer B:0.1% TFA in acetonitrile |
| Gradient: | 150 μl sample applied to column |
| | Run buffer A for 20 minutes |
| | Start linear gradient, 0–80% buffer B, run over 35 minutes |
| | Run 80–0% buffer B over 5 minutes |
| Flow: | 0.9 ml/minute |
| Temperature: | Ambient |
| Detection: | Absorbance from 290 to 284 nm, with most runs being detected at 210 and 235 |

Fifteen eluent fractions were collected, at the approximate times from injection noted in the following table. In addition, a TNF release essay, as described in Example 2, was performed on each fraction, with the following results:

| Fraction # | Time (min.) | TNF (pg/ml) |
|---|---|---|
| 1 | 5.6–6.25 | 203 |
| 2 | 6.25–6.6 | −157 |
| 3 | 6.6–7.1 | 1 |
| 4 | 7.1–7.9 | 11 |
| 5 | 7.9–8.4 | 84 |
| 6 | 8.4–8.9 | −24 |
| 7 | 8.9–9.4 | −10 |
| 8 | 9.4–10.0 | 36 |
| 9 | 10.0–10.4 | 24 |
| 10 | 10.4–12.0 | 11 |
| 11 | 12.0–13.6 | 49 |
| 12 | 13.6–14.2 | 39 |
| 13 | 14.2–15.35 | −9 |
| 14 | 15.35–16.75 | 39 |
| 15 | 16.75–18.20 | −5 |
| WholeVIRULIZIN ™ | | 213 |

Accordingly, the majority of the active components of VIRULIZIN™ eluted in Fraction 1. Activity was also found in Fractions 4–5, 8–9, 11–12, and 14.

Samples from all RP-HPLC fractions were analyzed by mass spectroscopy in accordance with Example 28. A review of the resultant spectra for the fractions indicated that the following compounds were likely present: taurocholic acid, a sialic acid-glycerol dimer, NaCl, trimethylamine, methylethylamine, and propylamine.

EXAMPLE 32

This example illustrates the compounds that have been identified in the inventive composition.

The inventive composition was prepared in accordance with Example 1 and subjected to standard methods of fractionation, including (1) dialysis in 100 MWCO dialysis membrane; (2) classical organic extractions including Folch extractions, (Tamari et al., Agr. Biol. Chem., 40 (10), 2057–2062 (1976)); (3) silica column chromatography; (4) ion exchange chromatography); and (5) preparative silica TLC fractionation using butanol: acetic acid: water 6:2:2 as the eluant and ninhydrin as the visualization reagent, using standard methods as disclosed in Dying Reagents for Thin Layer and Paper ChromatoQraphy, E. Merck, Darmstadt, Germany, 1971.

Identification of the compounds was based on the following instrumentation and techniques, used individually or in combination:

A VG 70-250S spectrometer was used to obtain EI-MS, CI-MS (OH—), and FAB-MS (in glycerol or thioglycerol matrices). A VG Analytical Model ZAB-SE instrument was used to obtain EI-MS, FAB-MS (in glycerol or thioglycerol matrices), and GC-MS. The gas chromatograph (GC) used in conjunction with the instrument was a Hewlett Packard model 5890. A Kratos profile spectrometer was used to obtain EI—MS, LSIM-MS (in glycerol and NPOE matrices), and GC-MS mass spectra. The GC used in conjunction with the instrument was also a Hewlett Packard model 5890. MS-MS, electrospray using either water or water alcohol (methanol or isopropyl alcohol) mixtures as solutes, EI-MS and FAB-MS in glycerol and thioglycerol were performed on a perkin-Elmer Sciex API-III spectrometer. Fractions were derivatized for MS analysis as required by acetylation with acetic anhydride/pyridine or methylation with diazomethane. Conversion of molecules into sodiated species was accomplished by addition of sodium acetate to the electrospray solute. Protonation of molecules for electrospray MS was achieved using acetic acid or trifluoroacetic acid. TLCs of extracts and standards were run on silica TLC plates using butanol:acetic acid: water 6:2:2 or cited eluants as mobile phases and several reagent sprays for visualization.

Standard methods were used in connection with the aforementioned instruments, which are further recited in the following references: Rigler et al., J. Chromatography, 277, 321–327 (1983); Sundaram, et al., Clinica Chimica Acta, 34 425–429 (1971); Bandurski et al., J. Biol. Chem., 193 405–410 (1951); and Larsen et al., J. Chromatography, 226 484–487 (1981).

Typical TLC profiles on silica plates (using butanol:acetic acid: water, 6:2:2 as the eluant) are as tabulated for active lots of VIRULIZIN™:

| Visualization Reagent | TLC Profile* |
|---|---|
| sulfuric acid | Rf = 0 to 0.25, white spot |
| ceric ammonium sulfate | Rf = 0.05 to 0.42, yellow spot |
| molybdate | Rf = 0 to 0.3, pale blue-green to white spots with blue-green edges |
| anisaldehyde | Rf = 0.03 to 0.25, whit spot |
| 8-anilino-1-napthalene sulfonic acid | Rf = 0 to 0.25, yellow spots (by eye) |
| ninhydrin | Rf = 0 to 0.13, pale pink spot |
| | Rf = 0.12 to 0.3, purple spear-headed shaped spot |

| Visualization Reagent | TLC Profile* |
|---|---|
| | Rf = 0.15 to 0.3, burgundy spot |
| | Rf = 0.3 to 0.45, pale yellow-colored spot |
| | Rf = 0.35 to 0.5, deep yellow-colored spot |
| | Rf = 0.4 to 0.5, burgundy spot |
| | Rf = 0.5 to 0.6, burgundy spot |

*Rf values will vary slightly depending on the degree of activity of the silica gel coating of the plates and the precise composition of the elution solvent.

Analysis of the inventive composition using the aforementioned instrumentation and methods revealed the following compounds contained therein:

1) BILE ACIDS:
cholic acid;
glycocholic acid;
deoxyglycocholic acid;
cholesterol sulfate;
deoxycholic acid;
chenodeoxycholic acid; and
taurocholic acid.

Note: From the MS it is not distinguishable if —OH and —$H_2$ are occurring in the MS or if the deoxy, dideoxy and unsaturated analogs are also present to begin with. These compounds may all be present as salts of ammonium, alkylammonium and inorganic cations.

2) PHOSPHOLIPIDS, SPHINGOLIPIDS AND RELATED (HYDROLYSIS) PRODUCTS:
stearic acid $CH_3(CH_2)_{16}COOH$;
palmitic acid $CH_3(CH_2)_{14}COOH$;
oleic acid Z-9 octadecanoic acid: $CH_3(CH_2)_2CH_2CH=CHCH_2(CH_2)_6COOH$
oxidized or hydroxylated/unsaturated short chain fatty acids, such as $C_6H_8O_3$ ($CH_3CH=CH-COCH_2COOH$ or a $C_6$ acid with 2 double bonds and a hydroxide);
acetic acid;
stearic acid diglyceride;
palmitic acid diglyceride;
stearic acid, palmitic acid diglyceride;
stearic acid monoglyceride-phosphocholine (a lysolecithin);
stearic acid monoglyceride;
stearic acid triglyceride;
phosphocholine;
phosphoserine;
phosphosphingosine;
sphingomyelin;
lecithin;
stearic acid-sphingosine;
sphingosine;
phosphoglycerol;
glycerol;
choline;
glycero-phosphocholine;
stearic acid, oleic acid diglyceride;
stearic acid, oleic acid phosphoglycerol;
stearic acid amide;
stearic acid methylamide; and
palmitic acid amide.

In addition, preliminary HPLC and titration evidence has been obtained which shows that shorter chain fatty acids are also present (acids range from $C_1$ to $C_{30}$).

3) MUCIN HYDROLYSIS PRODUCTS:
sialic acids and their mono and diacetylated monomers;
N-acetylneuraminic acid;
hexosamines, such as glucosamine;
L-fucose;
hexosamine-hexuronic acid (dimer) disulfate;
glucuronic acid;
glucuronic acid or iduronic acid disulfate, monoacetylated;
sialic acid-glycerol (dimer); and
dimers, trimers, oligomers and polymers of the above monomers in acetylated and sulfated form.

4) FAT-SOLUBLE VITAMINS:
Vitamin A2;
Vitamin D1;
lumisterol (present from its vitamin D1 complex);
Vitamin E;
Vitamin K1 oxide; and
Vitamin K5.

5) MISCELLANEOUS ORGANIC:
urea;
alkyl amines, including methyl amine, dimethylamine, ethylamine, methylethylamine, diethylamine, dipropylamine, butylethylamine;
amino acids, including taurine, glutamic acid, glycine, alanine, n-leucine, phosphoserine, phosphoethanolamine, aspartic acid, threonine, serine, sarcosine, α-amino adipic acid, citrulline, valine, isoleucine, β-alanine, γ-amino butyric acid, hydroxylysine, ornithine, and lysine;
butylated hydroxy toluene (BHT); and
polyethylene glycol.

EXAMPLE 33

This example illustrates the saccharide components of the invention.

The monosaccharide composition of the samples was determined before and after hydrolysis. All reagents used to analyze the monosaccharides were of analytical grade. THF (trifluoroacetic acid) obtained from Aldrich after dilution with deionized water, was used for the hydrolysis of samples. A 50% (W/W) NaOH solution (low in carbonate) was purchased from Fisher Scientific. Sodium acetate was from Fluka-Gerantie, New York.

To release the monosaccharides, the samples were treated with 4 M trifluoroacetic acid for 4 hours at 100° C. The samples were lyophilized and analyzed by high performance liquid chromatography-anion exchange using a Dionex Bio-LC System for carbohydrates with Carbopack Pal separating column (250×4 mm i.d.) and HPLC-AG6 guard column (50×4 mm i.d.) equipped with a 25 ul sample loop. Detection of eluting monosaccharides was accomplished with PAD, i.e., pulsed amperometric detector. Conditions were as follows:

Before Hydrolysis

For detection of inositol, sialic acid and glucuronic acid, isocratic elution eluant (100 mM NaOH+150 mM NaOAc mixture) was used. The eluant was protected from the atmosphere with a helium module degasser. The flow rate was 1 ml/min through the column.

Detection of monosaccharides, including fucose, galactosamine, galactose, glucose and mannose, also was accomplished via isocratic elution, eluant (15 mM NaOH) with a post column 300 mM NaOH, at a flow rate 1 ml/min.

The detector settings E1=0.05V, E2=0.60V, E3=0.60V, t1=120 ms, t2=120 ms, t3=300 ms; gold working electrode; silver-silver chloride reference electrode; output range 1–3 K nAmp full scale; chart speed 0.5 cm/min.

Measurements were performed of the detector for uronic acid and monosaccharides. A linear response was obtained for concentrations varying from 0.5–2.5 ug/ml by a progressive dilution of a standard mixture.

After Hydrolysis

Monosaccharides were detected after hydrolysis of the sample after applying a gradient elution, eluant A (50 mM NaOH) and eluant B (50 mM NaOH/150 mM NaOAc mixture). The eluants were protected from the atmosphere with a helium module degasser. A Spectra-Physics (SP 4270) integrator was used to analyze the output. The standard gradient was injection in 100% eluant A, followed by a linear progression to 80% A:20% B over the next 10 minutes. This condition was maintained for 20 minutes and then the eluant returned to 100% A over 5 minutes followed by at least 10 minutes of equilibration before injection of the next sample.

The results of the monosaccharide analysis as described are presented in the following table:

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating a cancer comprising administering to a patient suffering from said cancer a therapeutically effective amount of a composition obtained from an original bile/solvent solution, said bile extracted from bile of bovines, said composition consisting of:
   small molecular weight components of less than 3000 daltons in a buffered salt solution having a pH of about 7.0 to about 8.56, not more than 10 ppm ethanol and not more than 5 ppm ether, and no measurable levels of IL-1a, IL-1b, TNF, IL-6, IL-8, IL-4, GM-CSF, IFN-gamma or ammonia; said small molecular weight components obtained from bile extracted from bile of bovine using a solvent;
   wherein said composition has been standardized for potency by demonstrating TNE-α release from human peripheral blood mononuclear cells of at least 100 pg/ml;
   wherein said composition is concentrated to about one tenth of the original bile/solvent solution volume; and
   wherein said composition is capable of stimulating monocytes and/or macrophages, shows no cytotoxicity to human peripheral blood mononuclear cells, and is not an endotoxin.

2. The method of claim 1, wherein said composition further consists of a pharmaceutically acceptable carrier.

| | Sample | | | | | | | |
|---|---|---|---|---|---|---|---|---|
| | MU100 (water layer from a Folch extraction) | | MU 148 A (dialyzed MU100B) | | MU 116 A (dialyzed premix A lot BC0241) | | MU100 GB (ethyl acetate extract from green bile) | |
| Sugar | before hydrolysis | after hydrolysis | before hydrolysis | after hydrolysis | before hydrolysis | after hydrolysis | before hydrolysis | after hydrolysis |
| inositol | | | | same rt of glycerol | | same rt of glycerol | | same rt of glycerol |
| siatic acid | | <279.3 ng/mg | | 0 | | 0 | 3.67 µg/mg | 0 |
| glucuronic acid | 0 | 284.4 ng/mg | 0 | 0 | 0 | 3.02 µg/mg | 4.04 µg/mg | 826.58 ng/mg |
| galacturonic acid | | | | | | | | |
| fucose | 0 | | 0 | | 0 | | 0 | |
| galactosamine | 0 | | 0 | | 0 | | 0 | |
| glucosamine | | <139.6 ng/mg | | 543.02 ng/mg | | 234.5 ng/mg | | |
| galactose | 0 | | 0 | | 0 | | 0 | |
| glucose | 0 | | 0 | | 0 | | 0 | |
| mannose | 0 | | 0 | | 0 | | 0 | |
| unknown (most likely glycerol phosphate | | yes | | | | strong peak of unknown compound | | |

As noted in the table, only the ethyl acetate extract of green bile (batch MU100 GB) was shown to include any monosaccharide prior to hydrolysis, those being sialic and glucuronic acids, in microgram per milliliter concentration. After hydrolysis, no sialic acid was detected and the glucuronic acid was present at approximately 20% the concentration. After hydrolysis, other preparatives of the inventive compositions were shown to contain sialic acid, glucuronic acid, glucosamine, and inositol.

3. The method of claim 1, wherein said composition is hyperosmolar.

4. The method of claim 1, wherein said composition is tyndallized over 3 cycles at 104° C.

5. The method of claim 1, wherein said composition is tyndallized for a single cycle at 121° C.

6. The method of claim 1, wherein said composition has a finished fill volume of about 3 mL and a biological activity of about 2.0 to 2.5× compared to a composition obtained from a manufacturing process resulting in about a 7.5 mL dosage fill volume.

7. The method of claim 1, wherein said cancer is selected from the group consisting of malignant melanoma, ovarian carcinoma, ENT carcinoma, endometrial carcinoma, lung carcinoma, and Kaposi's sarcoma.

8. A method of treating a cancer selected from the group consisting of malignant melanoma, ovarian carcinoma, ENT carcinoma, endometrial carcinoma, lung carcinoma, and Kaposi's sarcoma comprising administering to a patient suffering from said cancer a therapeutically effective amount of a composition obtained from an original bile/solvent solution, said bile extracted from bile of bovines, said composition consisting of:

small molecular weight components of less than 3000 daltons in a buffered salt solution having a pH of about 7.0 to about 8.56, not more than 10 ppm ethanol and not more than 5 ppm ether, and no measurable levels of IL-1a, IL-1b, TNF, IL-6, IL-8, IL-4, GM-CSF, IFN-gamma or ammonia; said small molecular weight components obtained from bile extracted from bile of bovine using a solvent;

wherein said composition has been standardized for potency by demonstrating TNF-α release from human peripheral blood mononuclear cells of at least 100 pg/ml;

wherein said composition is concentrated to about one tenth of the original bile/solvent solution volume; and wherein said composition is capable of stimulating monocytes and/or macrophages, shows no cytotoxicity to human peripheral blood mononuclear cells, and is not an endotoxin.

* * * * *

UNITED STATES PATENT AND TRADEMARK OFFICE
CERTIFICATE OF CORRECTION

PATENT NO.    : 6,596,319 B2
DATED         : July 22, 2003
INVENTOR(S)   : Rang et al.

It is certified that error appears in the above-identified patent and that said Letters Patent is hereby corrected as shown below:

<u>Column 74,</u>
Line 21, after "by demonstrating" and before "release from", please replace "TNE-α" with -- TNF-α --.

Signed and Sealed this

Seventh Day of October, 2003

JAMES E. ROGAN
*Director of the United States Patent and Trademark Office*